US012195419B2

(12) United States Patent
Slusher et al.

(10) Patent No.: US 12,195,419 B2
(45) Date of Patent: Jan. 14, 2025

(54) GLUTAMINE ANTAGONISTS AND USES THEREOF

(71) Applicants: The Johns Hopkins University, Baltimore, MD (US); Ústav organické chemie a biochemie AV ČR, v.v.i., Czechia (CZ)

(72) Inventors: Barbara Slusher, Kingsville, MD (US); Rana Rais, Owings Mills, MD (US); Pavel Majer, Sykesville, MD (US); Lukas Tenora, Czechia (CZ); Katerina Novotna, Czechia (CZ); Jesse Alt, Nottingham, MD (US)

(73) Assignees: The John Hopkins University, Baltimore, MD (US); Ustav organické chemie a biochemie AV CR, v.v.i. (CZ)

( * ) Notice: Subject to any disclaimer, the term of this patent is extended or adjusted under 35 U.S.C. 154(b) by 605 days.

(21) Appl. No.: 16/754,053

(22) PCT Filed: Oct. 5, 2018

(86) PCT No.: PCT/US2018/054581
§ 371 (c)(1),
(2) Date: Apr. 6, 2020

(87) PCT Pub. No.: WO2019/071110
PCT Pub. Date: Apr. 11, 2019

(65) Prior Publication Data
US 2023/0009398 A1    Jan. 12, 2023

Related U.S. Application Data

(60) Provisional application No. 62/728,214, filed on Sep. 7, 2018, provisional application No. 62/569,118, filed on Oct. 6, 2017.

(51) Int. Cl.
*C07C 271/22*   (2006.01)
*A61P 35/00*    (2006.01)
*C07C 245/18*   (2006.01)
*C07D 209/20*   (2006.01)

(52) U.S. Cl.
CPC .......... *C07C 271/22* (2013.01); *A61P 35/00* (2018.01); *C07C 245/18* (2013.01); *C07D 209/20* (2013.01); *C07C 2603/18* (2017.05)

(58) Field of Classification Search
None
See application file for complete search history.

(56) References Cited

U.S. PATENT DOCUMENTS

| | | | |
|---|---|---|---|
| 10,336,778 B2 | 7/2019 | Slusher et al. |
| 10,568,868 B2 | 2/2020 | Slusher et al. |
| 10,738,066 B2 | 8/2020 | Slsuher et al. |
| 10,842,763 B2 | 11/2020 | Slusher et al. |
| 10,954,247 B2 | 3/2021 | Slusher et al. |
| 11,110,104 B2 | 9/2021 | Slusher et al. |
| 11,185,534 B2 | 11/2021 | Slusher et al. |
| 2006/0276438 A1 | 12/2006 | Sethuraman et al. |
| 2008/0107624 A1 | 5/2008 | D'Andrea et al. |
| 2008/0146526 A1 | 6/2008 | Gallop et al. |
| 2009/0062223 A1 | 3/2009 | Keicher et al. |
| 2018/0221395 A1 | 8/2018 | Slusher et al. |
| 2021/0145779 A1 | 5/2021 | Slusher et al. |
| 2021/0206787 A1 | 7/2021 | Slusher et al. |

FOREIGN PATENT DOCUMENTS

| | | |
|---|---|---|
| WO | WO-9207562 A1 | 5/1992 |
| WO | WO-2017023774 A1 | 2/2017 |
| WO | WO-2017023787 A1 | 2/2017 |

OTHER PUBLICATIONS

Ahluwalia.,G.S., et.al., "Metabolism and Action of Amino Acid Analog Anti-cancer Agents.," Pharmacology & Therapeutics 46(2):243-271, Pergamon Press, England (1990).
Alt,J., et.al., "Bioanalysis of 6-diazo-5-oxo-1-norleucine in Plasma and Brain by Ultra-performance Liquid Chromatography Mass Spectrometry.," Analytical Biochemistry 474:28-34, Elsevier, United States (Jan. 2010).
Barclay, R.K., et.al., "Effects of 6-diazo-5-oxol-norleucine and Other Tumor Inhibitors on the Biosynthesis of Nicotinamide Adenine Dinucleotide in Mice.," Cancer research 26(2):282-286, American Association for Cancer Research, United States (Feb. 1966).
Carr, E.L., et al., "Glutamine Uptake and Metabolism Are Coordinately Regulated by ERK/MAPK during T Lymphocyte Activation," J Immunol 185(2):1037-1044, American Association of Immunologists, United States (Jul. 2010).

(Continued)

*Primary Examiner* — Sudhakar Katakam
*Assistant Examiner* — Jennifer C Sawyer
(74) *Attorney, Agent, or Firm* — Sterne, Kessler, Goldstein & Fox P.L.L.C

(57) ABSTRACT

Glutamine antagonists and their use for treating oncological, immunological, and neurological diseases are disclosed. Also disclosed are methods for treating an oncological, immunological, infectious or neurological disease or disorder, the method comprising administering to a subject in need of treatment thereof a therapeutically effective amount of a glutamine antagonist of the disclosure or the pharmaceutical composition thereof. Also disclosed are methods of enhancing the effects of an immune checkpoint inhibitor, enabling a subject to respond to an immune checkpoint inhibitor, or enabling the toxicity or the dose or number of treatments with an immune checkpoint inhibitor to be reduced, comprising administering to a subject in need of treatment thereof a therapeutically effective amount of a glutamine antagonist of the disclosure or the pharmaceutical composition thereof, and an immune checkpoint inhibitor. Also disclosed are methods for treating an oncological, immunological, infectious or neurological disease or disorder that is refractory to checkpoint inhibitor therapy, the method comprising administering to a subject in need thereof, and having the refractory disease or disorder, a therapeutically effective amount of a glutamine antagonist of the disclosure or the pharmaceutical composition thereof.

24 Claims, 9 Drawing Sheets

(56) References Cited

OTHER PUBLICATIONS

Cervantes-Madrid, D., et al., "Reviving Lonidamine and 6-Diazo-5-oxo-L-norleucine to be used in Combination for Metabolic Cancer Therapy," BioMed Research International 2015:690492, Hindawi Pub. Co, United States (2015).

Chung, S.H., et al., "Studies on sound-induced epilepsy in mice," Proc R Soc Lond B Biol Sci 221(1223):145-68, Royal Society Publishing, United Kingdom (Apr. 1984).

Cinatl, J., et al., "Antiviral effects of 6-diazo-5-oxo-L-norleucin on replication of herpes simplex virus type 1," Antiviral Res 33(3):165-75, Elsevier, Netherlands (Feb. 1997).

Coffey, G.L., et al., "6-diazo-5-oxo-L-norleucine, a New Tumor-inhibitory Substance. I. Biologic Studies," Antibiotics & Chemotherapy 6(8):487-497, Washington Institute of Medicine, United States (Aug. 1956).

Coggin, J.H., et al., "6-Diazo-5-Oxo-L-Norleucine Inhibition of *Escherichia coli*," J Bacteriol 89(5):1348-53, American Society for Microbiology, United States (May 1965).

Colombo, S., et al., "Anaphase-promoting complex/cyclosome-Cdh1 coordinates glycolysis and glutaminolysis with transition to S phase in human T lymphocytes," PNAS 107(44):18868-73, National Academy of Sciences, United States (Nov. 2010).

Cui, F., et al., "Overexpression of Cathepsin L is Associated with Gefitinib Resistance in Non-small Cell Lung Cancer," Clinical & Translational Oncology 18(7):722-727, Springer Italia, Italy (Jul. 2016).

Deberardinis, R.J. and Cheng, T., "Q's Next: the Diverse Functions of Glutamine in Metabolism, Cell Biology and Cancer," Oncogene 29(3):313-324, Nature Publishing Group, England (Jan. 2010).

Dion, H.W., et al., "6-Diazo-5-oxo-L-norleucine, a New Tumor-inhibitory Substance. II. Isolation and Characterization," Journal of the American Chemical Society 78(13):3075-3077, (Jul. 1956).

Dranoff, G., et al., "Combination Chemotherapy in Vitro Exploiting Glutamine Metabolism of Human Glioma and Medulloblastoma," Cancer Research 45(9):4082-4086, American Association for Cancer Research, United States (Sep. 1985).

Dranoff, G., et al., "Influence of Glutamine on the Growth of Human Glioma and Medulloblastoma in Culture," Cancer Research 45(9):4077-4081, American Association for Cancer Research, United States (Sep. 1985).

Eagan, R.T., et al., "Phase II Study on DON in Patients with Previously Treated Advanced Lung Cancer," Cancer Treatment Reports 66(8):1665-1666, National Cancer Institute, United States (Aug. 1982).

Earhart, R.H., et al., "Phase I Trial of 6-diazo-5-oxo-L-norleucine (DON) Administered by 5-day Courses," Cancer Treatment Reports 66(5):1215-1217, National Cancer Institute, United States (May 1982).

Earhart, R.H., et al., "Phase II Trial of 6-diazo-5-oxo-L-norleucine Versus Aclacinomycin-a in Advanced Sarcomas and Mesotheliomas," Investigational New Drugs 8(1):113-119, Springer, United States (Feb. 1990).

Erickson, J.W. and Cerione R.A., "Glutaminase: A Hot Spot for Regulation of Cancer Cell Metabolism?," Oncotarget 1(8):734-740, Impact Journals, United States (Dec. 2010).

Eshleman, J.S., et al., "Inhibition of the Mammalian Target of Rapamycin Sensitizes U87 Xenografts to Fractionated Radiation Therapy," Cancer Research 62(24):7291-7297, American Association for Cancer Research, United States (Dec. 2002).

Fogal, V., et al., "Mitochondrial p32 is Upregulated in Myc Expressing Brain Cancers and Mediates Glutamine Addiction," Oncotarget 6(2):1157-1170, Impact Journals, United States (Jan. 2015).

Grayzel, A.I., et al., "Suppression of Uric Acid Synthesis in the Gouty Human by the Use of 6-diazo-5-oxo-L-norleucine.," The Journal of Clinical Investigation 39:447-454, American Society for Clinical Investigation, United States (Mar. 1960).

Gross, M.I., et al., "Antitumor Activity of the Glutaminase Inhibitor CB-839 in Triple-Negative Breast Cancer," Molecular Cancer Therapeutics 13(4):890-901, American Association for Cancer Research, United States (Apr. 2014).

Harding, J.J., et al., "Safety and Tolerability of Increasing Doses of CB-839, a First-in-class, Orally Administered Small Molecule Inhibitor of Glutaminase, in Solid Tumors," Journal of Clinical Oncology 33(15_suppl ):2512, (May 2015).

Hausch, F., et al., "Design, synthesis, and evaluation of gluten peptide analogs as selective inhibitors of human tissue transglutaminase," Chemistry and Biology 10(3):225-231, American Chemical Society, United States (Mar. 2003).

Henderson, J.M., et al., "Hepatocellular Carcinoma: Mouse Models and the Potential Roles of Proteases," Cancer Letters 387:106-113, Elsevier Science Ireland, Ireland (Feb. 2017).

Hensley, C.T., et al., "Glutamine and Cancer: Cell Biology, Physiology, and Clinical Opportunities," The Journal of Clinical Investigation 123(9):3678-3684, American Society for Clinical Investigation, United States (Sep. 2013).

Hofer, A., et al., "Trypanosoma Brucei CTP Synthetase: a Target for the Treatment of African Sleeping Sickness," Proceedings of the National Academy of Sciences of the United States of America 98(11):6412-6416, National Academy of Sciences, United States (May 2001).

Hu, X., et al., "Genetic Alterations and Oncogenic Pathways Associated with Breast Cancer Subtypes," Molecular Cancer Research 7(4):511-522, American Association for Cancer Research, United States (Apr. 2009).

Huang, R.C., et al., "Inhibition of replication of human respiratory syncytial virus by 6-diazo-5-oxo-L-norleucine," Antiviral Res 25(3-4):269-79, Elsevier, Netherlands (Dec. 1994).

Huber, K.R., et al., "Uptake of Glutamine Antimetabolites 6-Diazo-5-oxo-L-norleucine (DON) and Acivicin in Sensitive and Resistant Tumor Cell Lines," In. J. Cancer 41:752-755, Union for International Cancer Control, Switzerland (1988).

Hutchinson, J.A., et al., "Peptide Hormones and Lipopeptides: from Self-assembly to Therapeutic Applications," Journal of Peptide Science 23(2):82-94, John Wiley & Sons, England (Feb. 2017).

International Search Report and Written Opinion for International Application No. PCT/US2018054581, Korean Intellectual Property Office, Republic of Korea, mailed Feb. 1, 2019, 12 pages.

Konopleva., et al., "Phase 1 study: Safety and tolerability of increasing doses of cb-839, an orally-administered small molecule inhibitor of glutaminase," in Acute Leukemia, Haematologica (2015).

Kovach, J.S., et al., "Phase I and Pharmacokinetic Studies of DON," Cancer Treatment Reports 65(11-12):1031-1036, National Cancer Institute, United States (Nov.-Dec. 1981).

Kulcsar, K.A., et al., "Interleukin 10 modulation of pathogenic Th17 cells during fatal alphavirus encephalomyelitis, " PNAS 111(45):16053-16058, National Academy of Sciences, United States (Nov. 2014).

Le, A., et al., "Glucose-independent Glutamine Metabolism via TCA Cycling for Proliferation and Survival in B Cells," Cell Metabolism 15(1):110-121, Cell Press, United States (Jan. 2012).

Lee, M.D., et al., "New antitumor antibiotic, LL-D05139 beta. Fermentation, isolation, structure determination and biological activities," Journal of Antibiotics 40(12):1657-63, Springer, Germany (Dec. 1987).

Lee, Y.Z., et al., "Discovery of Selective Inhibitors of Glutaminase-2, which Inhibit mTORC1, Activate Autophagy and Inhibit Proliferation in Cancer Cells," Oncotarget 5(15):6087-6101, Impact Journals, United States (Aug. 2014).

Liu, W., et al., "Reprogramming of Proline and Glutamine Metabolism Contributes to the Proliferative and Metabolic Responses Regulated by Oncogenic Transcription Factor c-MYC," Proceedings of the National Academy of Sciences of the United States of America 109(23):8983-8988, National Academy of Sciences, United States (Jun. 2012).

Lynch, G., et al., "Phase II Evaluation of DON (6-diazo-5-oxo-L-norleucine) in Patients with Advanced Colorectal Carcinoma," American Journal of Clinical Oncology 5(5):541-543, Lippincott Williams & Wilkins, United States (Oct. 1982).

Maciolek, J.A., et al., "Metabolism of activated T lymphocytes," Curr Opin Immunol 27:60-74, Elsevier, Netherlands (Apr. 2014).

(56) References Cited

OTHER PUBLICATIONS

Magill, G.B., et al., "Pharmacological and initial therapeutic observations on 6-diazo-5-oxo-1-norleucine (DON) in human neoplastic disease," Cancer 10(6):1138-50, American Cancer Society, United States (Nov. 1957).

Medina, M.A., et al., "Relevance of Glutamine Metabolism to Tumor Cell Growth," Molecular and Cellular Biochemistry 113(1):1-15, Springer, Netherlands (Jul. 1992).

McDermott, L.A., et al., "Design and Evaluation of Novel Glutaminase Inhibitors," Bioorganic & Medicinal Chemistry 24(8):1819-1839, Elsevier Science, England (Apr. 2016).

Nedelcovych, M.T., et al., "N-(Pivaloyloxy)alkoxy-carbonyl Prodrugs of the Glutamine Antagonist 6-Diazo-5-oxo-L-norleucine (DON) as a Potential Treatment for HIV Associated Neurocognitive Disorders," Journal of Medicinal Chemistry 60(16):7186-7198, American Chemical Society, United States (Aug. 2017).

Nishio, M., et al., "Antiviral Effect of 6-diazo-5-oxo-L-norleucine, Antagonist of Gamma-glutamyl Transpeptidase, on Replication of Human Parainfluenza Virus Type 2," The Journal of General Virology 71( Pt 1):61-67, Microbiology Society, England (Jan. 1990).

Ostrom, Q.T., et al., "CBTRUS Statistical Report: Primary Brain and Central Nervous System Tumors Diagnosed in the United States in 2008-2012," Neuro-oncology 17(Suppl 4):iv1-iv62, Oxford University Press, England (Oct. 2015).

Ovejera, A.A., et al., "Efficacy of 6-diazo-5-oxo-L-norleucine and N-[N-gamma-glutamyl-6-diazo-5-oxo-norleuciny1]-6-diazo-5-oxo-norleucine against Experimental Tumors in Conventional and Nude Mice," Cancer Research 39(8):3220-3224, American Association for Cancer Research, United States (Aug. 1979).

Potter, M., et al., "Neurological sequelae induced by alphavirus infection of the CNS are attenuated by treatment with the glutamine antagonist 6-diazo-5-oxo-1-norleucine," J Neurovirol 21(2):159-73, Springer, Germany (Apr. 2015).

Rahman, A., et al., "Phase I Study and Clinical Pharmacology of 6-diazo-5-oxo-L-norleucine (DON)," Investigational New Drugs 3(4):369-374, Springer, United States (1985).

Rais, R., et al., "Discovery of 6-diazo-5-oxo-L-norleucine (DON) Prodrugs with Enhanced CSF Delivery in Monkeys: a Potential Treatment for Glioblastoma," Journal of Medicinal Chemistry 59(18):8621-8633, American Chemical Society, United States (Sep. 2016).

Rautio, J., et al., "Prodrugs: Design and Clinical Applications," Nature Reviews. Drug Discovery 7(3):255-270, Nature Publishing Group, England (Mar. 2008).

Reitzer, L.J., et al., "Evidence that Glutamine, not Sugar, is the Major Energy Source for Cultured HeLa Cells," The Journal of Biological Chemistry 254(8):2669-2676, American Society for Biochemistry and Molecular Biology, United States (Apr. 1979).

Ru, P., et al., "Tumor Metabolism of Malignant Gliomas," Cancers 5(4):1469-1484, MDPI, Switzerland (Dec. 2013).

Rubin, J., et al., "A Phase II Study of 6-diazo-5-oxo-L-norleucine (DON, NSC-7365) in Advanced Large Bowel Carcinoma," American Journal of Clinical Oncology 6(3):325-326, Lippincott Williams & Wilkins, United States (Jun. 1983).

Schulze, A. and Harris, A.L., "How Cancer Metabolism is Tuned for Proliferation and Vulnerable to Disruption," Nature 491(7424):364-373, Nature Publishing Group, England (Nov. 2012).

Shelton, L.M., et al., "Glutamine Targeting Inhibits Systemic Metastasis in the VM-M3 Murine Tumor Model," International Journal of Cancer 127(10):2478-2485, International Union Against Cancer, United States (Nov. 2010).

Shijie, J., et al., "Blockade of Glutamate Release from Microglia Attenuates Experimental Autoimmune Encephalomyelitis in Mice," Tohoku J. Exp. Med. 217(2):87-92, Tohoku University Medical Press, Japan (Feb. 2009).

Shukla, K., et al., "Design, Synthesis, and Pharmacological Evaluation of Bis-2-(5-phenylacetamido-1,2,4-thiadiazol-2-yl)ethyl Sulfide 3 (BPTES) Analogs as Glutaminase Inhibitors," Journal of Medicinal Chemistry 55(23):10551-10563, American Chemical Society, United States (Dec. 2012).

Sklaroff, R.B., et al., "Phase I Study of 6-diazo-5-oxo-L-norleucine (DON)," Cancer Treatment Reports 64(12):1247-1251, National Cancer Institute, United States (1980).

Stupp, R., et al., "Radiotherapy Plus Concomitant and Adjuvant Temozolomide for Glioblastoma," The New England Journal of Medicine 352(10):987-996, Massachusetts Medical Society, United States (Mar. 2005).

Stupp, R., et al., "Effects of Radiotherapy with Concomitant and Adjuvant Temozolomide Versus Radiotherapy Alone on Survival in Glioblastoma in a Randomised Phase III Study: 5-year Analysis of the EORTC-NCIC Trial," The Lancet. Oncology 10(5):459-466, Lancet Pub. Group, England (May 2009).

Sullivan, M.P., et al., "A Comparison of the Effectiveness of Standard Dose 6-mercaptopurine, Combination 6-mercaptopurine and DON, and High-loading 6-mercaptopurine Therapies in Treatment of the Acute Leukemias of Childhood: Results of a Coperative Study," Cancer Chemotherapy Reports 18:83-95, National Cancer Institute, United States (May 1962).

Sullivan, M.P., et al., "Pharmacokinetic and Phase I Study of Intravenous DON (6-diazo-5-oxo-L-norleucine) in Children," Cancer Chemotherapy Reports 21(1):78-84, Springer Verlag, Germany (1988).

Tanaka, K., et al., "Compensatory Glutamine Metabolism Promotes Glioblastoma Resistance to mTOR Inhibitor Treatment," The Journal of Clinical Investigation 125(4):1591-1602, American Society for Clinical Investigation, United States (Apr. 2015).

Tarnowski, G.S., and Stock, C.C., "Effects of Combinations of Azaserine and of 6-diazo-5-oxo-L-norleucine with Purine Analogs and Other Antimetabolites on the Growth of Two Mouse Mammary Carcinomas," Cancer Research 17(10):1033-1039, American Association for Cancer Research, United States (Nov. 1957).

Thangavelu, K., et al., "Structural Basis for the Active Site Inhibition Mechanism of Human Kidney-type Glutaminase (KGA)," Scientific Reports 4:3827, Nature Publishing Group, England (Jan. 2014).

Tran, T.Q., et al., "Glutamine Deficiency Induces DNA Alkylation Damage and Sensitizes Cancer Cells to Alkylating Agents through Inhibition of ALKBH Enzymes," PLoS Biology 15(11):e2002810, Public Library of Science, United States (Nov. 2017).

Ueki, N., et al., "Synthesis and Preclinical Evaluation of a Highly Improved Anticancer Prodrug Activated by Histone Deacetylases and Cathepsin L," Theranostics 6(6):808-816, Ivyspring International Publisher, Australia (Mar. 2016).

Upadhyay, R.K., "Drug Delivery Systems, CNS Protection, and the Blood Brain Barrier," BioMed Research International 2014:869269, Hindawi Pub. Co, United States (2014).

Weller, M., et al., "EANO Guideline for the Diagnosis and Treatment of Anaplastic Gliomas and Glioblastoma.," The Lancet. Oncology 15(9):e395-403, Lancet Pub. Group, England (Aug. 2014).

Willis, R.C. and Seegmiller, J.E., "The Inhibition by 6-diazo-5-oxo-L-norleucine of Glutamine Catabolismof the Cultured Human Lymphoblast," Journal of Cellular Physiology 93(3):375-382, Wiley-Liss, United States (Dec. 1977).

Windmueller, H.G. and Spaeth, A.E., "Uptake and Metabolism of Plasma Glutamine by the Small Intestine," The Journal of Biological Chemistry 249(16):5070-5079, American Society for Biochemistry and Molecular Biology, United States (Aug. 1974).

Wise, D.R. and Thompson, C.B., "Glutamine Addiction: a New Therapeutic Target in Cancer," Trends in Biochemical Sciences 35(8):427-433, Elsevier Trends Journals, England (Aug. 2010).

Wise, D.R., et al., "Myc Regulates a Transcriptional Program that Stimulates Mitochondrial Glutaminolysis and Leads to Glutamine Addiction," Proceedings of the National Academy of Sciences of the United States of America 105(48):18782-18787, National Academy of Sciences, United States (Dec. 2008).

Yoshioka, K., et al., "Glutamine antagonist with diet deficient in glutamine and aspartate reduce tumor growth," Tokushima J Exp Med 39(1-2):69-76, Tokushima University, School of Medicine, Japan (Jun. 1992).

Zhang, W., et al., "Overexpression of Cysteine Cathepsin L Is a Marker of Invasion and Metastasis in Ovarian Cancer," Oncology Reports 31(3):1334-1342, D.A. Spandidos, Greece (Mar. 2014).

(56) References Cited

OTHER PUBLICATIONS

Zimmermann, S.C., et al., "N-substituted Prodrugs of Mebendazole Provide Improved Aqueous Solubility and Oral Bioavailability in Mice and Dogs," Journal of Medicinal Chemistry 61(9):3918-3929, American Chemical Society, United States (May 2018).

GLUTAMINE ANTAGONISTS AND USES THEREOF

FEDERALLY SPONSORED RESEARCH OR DEVELOPMENT

This invention was made with government support under CA193895 awarded by the National Institutes of Health (NIH). The government has certain rights in the invention.

BACKGROUND

Glutamine antagonists, such as 6-diazo-5-oxo-L-norleucine (DON), and aza-serine, have been shown to exhibit broad anti-viral (Antiviral Res. 1997; 33 (3): 165-75; Antiviral Res. 1994; 25 (3-4): 269-79), anti-infective (J. Bacteriol. 1965; 89:1348-53), anti-cancer (see, e.g., Yoshioka et al., 1992; Tokushima J. Exp. Med. 39 (1-2): 69-76), anti-inflammatory, and immunosuppressive activities (Kulcsar et al., 2014; 111:16053-58; Maciolek et al., 2014; Curr Opin Immunol. 27:60-74; Carr et al., 2010; J Immunol. 185:1037-1044; Colombo et al., 2010; Proc Natl Acad Sci USA. 107:18868-73), as well as inhibition of convulsions (Proc R Soc Lond B Biol Sci. 1984 Apr. 24; 221 (1223): 145-68), multiple sclerosis (Tohoku, J. Exp. Med. 2009; 217 (2): 87-92), epilepsy, and viral encephalitis (J. Neurovirol. 2015 April; 21 (2): 159-73. doi: 10.1007/s13365-015-0314-6), in many published preclinical and several clinical studies. However, the occurrence of severe toxicity (e.g., dose limiting GI toxicities, such as oral mucosistis, gastric bleeding, nausea and vomiting, and abdominal pain) when administering such glutamine antagonists at therapeutic dose levels has hampered their clinical development.

Prior attempts to mitigate the severe toxicity associated with glutamine antagonists, such as DON, have been unsuccessful. For example, dividing daily dosing and administering of DON every four to six hours apparently doubled DON's toxicity potential (MaGill, et al., 1957). In another example, development of a treatment involving DON dosed with PEGylated glutaminase to decrease plasma glutamine so that the DON dose could be reduced was halted after publication of a clinical trial.

SUMMARY

Provided are glutamine antagonists and their use in treating oncological, immunological, and neurological diseases.

In particular aspects, provided is a compound having a structure of formula (I):

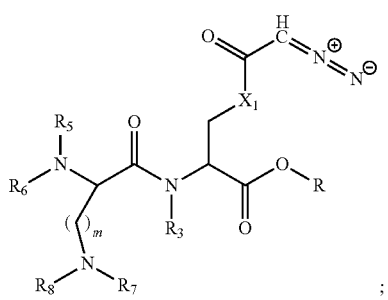

(I)

wherein:
m is an integer selected from the group consisting of 1, 2, 3, 4, 5, 6, 7, and 8;

$X_1$ is selected from the group consisting of —O— and —(CH$_2$)$_p$—, wherein p is an integer selected from the group consisting of 0, 1, 2, 3, 4, 5, 6, 7, and 8;

R is H, alkyl, substituted alkyl, cycloalkyl, substituted cycloalkyl, alkenyl, substituted alkenyl, alkynyl, substituted alkynyl, cycloalkenyl, substituted cycloalkenyl, tri(alkyl)ammonium, and tetra(alkyl)ammonium;

$R_3$, $R_5$, and $R_7$ are each independently H, $C_1$-$C_6$ alkyl, alkoxyl, cycloalkyl, heterocycloalkyl, aryl, and heteroaryl;

$R_6$ is selected from the group consisting of H, —(CH$_2$)$_t$—CH(NH—C(CH$_3$)(=O))—(CH$_2$)$_t$—R$_9$, —C(=O)—X$_2$—R$_{10}$, and one or more substituted or unsubstituted amino acids, wherein the one or more substituted or unsubstituted amino acids is bound to the nitrogen atom adjacent to $R_6$ through a carboxyl moiety of the one or more substituted or unsubstituted amino acids, wherein $X_2$ is present or absent and, when present, is selected from the group consisting of —O—, —O—(CH$_2$)$_q$—, —(CH$_2$)$_t$—, and —(CH$_2$)$_v$—CH=CH—(CH$_2$)$_v$—, wherein q and t are each independently selected from the group consisting of 1, 2, 3, 4, 5, 6, 7, and 8, each v is independently selected from the group consisting of 0, 1, 2, 3, 4, 5, 6, 7, and 8, and $R_9$ and $R_{10}$ are each independently selected from the group consisting of straight chain or branched alkyl, heteroalkyl, cycloalkyl, heterocycloalkyl, aryl, and heteroaryl; and $R_8$ is selected from the group consisting of H and —C(=O)—R$_{11}$, wherein $R_{11}$ is substituted or unsubstituted alkyl;

or an ester or pharmaceutically acceptable salt thereof.

In particular aspects, provided is a compound having a structure of formula (Ia):

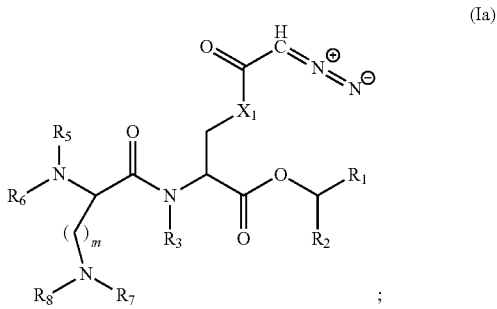

(Ia)

wherein:
m is an integer selected from the group consisting of 1, 2, 3, 4, 5, 6, 7, and 8;

$X_1$ is selected from the group consisting of —O— and —(CH$_2$)$_p$—, wherein p is an integer selected from the group consisting of 1, 2, 3, 4, 5, 6, 7, and 8;

$R_1$ and $R_2$ are each independently H, alkyl, substituted alkyl, cycloalkyl, substituted cycloalkyl, alkenyl, substituted alkenyl, alkynyl, substituted alkynyl, cycloalkenyl, substituted cycloalkenyl, tri(alkyl)ammonium, or tetra(alkyl)ammonium, wherein $R_1$ and $R_2$ can be the same or different, or $R_1$ and $R_2$ can together form a $C_3$-$C_6$ cycloalkyl ring;

$R_3$, $R_5$, and $R_7$ are each independently H, $C_1$-$C_6$ alkyl, alkoxy, cycloalkyl, heterocycloalkyl, aryl, or heteroaryl;

$R_6$ is selected from the group consisting of H, —(CH$_2$)$_t$—CH(NH—C(CH$_3$)(=O))—(CH$_2$)$_t$—R$_9$, —C(=O)—X₂—R₁₀, and one or more substituted or unsubstituted amino acids, wherein the one or more substituted or unsubstituted amino acids is bound to the nitrogen atom adjacent to R₆ through a carboxyl moiety of the one or more substituted or unsubstituted amino acids, wherein X₂ is present or absent and, when present, is selected from the group consisting of —O—, —O—(CH₂)$_q$—, —(CH₂)$_t$—, and —(CH₂)$_v$—CH=CH—(CH₂)$_v$—, wherein q and t are each independently selected from the group consisting of 1, 2, 3, 4, 5, 6, 7, and 8, each v is independently selected from the group consisting of 0, 1, 2, 3, 4, 5, 6, 7, and 8, and R₉ and R₁₀ are each independently selected from the group consisting of straight chain or branched alkyl, heteroalkyl, cycloalkyl, heterocycloalkyl, aryl, and heteroaryl; and R₈ is selected from the group consisting of H and —C(=O)—R₁₁, wherein R₁₁ is substituted or unsubstituted alkyl;

or an ester or pharmaceutically acceptable salt thereof.

In particular aspect, provided is a compound having a structure of formula (Ia):

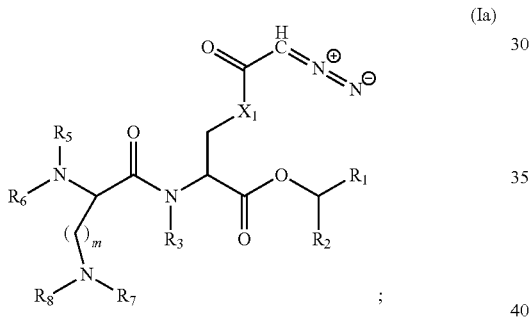

(Ia)

wherein:
m is an integer selected from the group consisting of 2, 3, 4, 5, and 6;
X₁ is selected from the group consisting of —O— and —(CH₂)—;
R₁ and R₂ are each independently the group consisting of H, C₁-C₆ alkyl, substituted C₁-C₆ alkyl, C₃-C₈ cycloalkyl, substituted C₃-C₈ cycloalkyl, C₂-C₆ alkenyl, substituted C₂-C₆ alkenyl, C₂-C₆ alkynyl, substituted C₂-C₆ alkynyl, C₄-C₈ cycloalkenyl, substituted C₄-C₈ cycloalkenyl, tri(C₁-C₆ alkyl) ammonium, and tetra(C₁-C₆ alkyl)ammonium, wherein R₁ and R₂ can be the same or different, or R₁ and R₂ can together with the carbon on which they are bound form a C₃-C₈ cycloalkyl;
R₃, R₅, and R₇ are each independently the group consisting of H, C₁-C₆ alkyl, C₃-C₈ cycloalkyl, C₃-C₆ heterocycloalkyl containing at least one heteroatom selected from the group consisting of O, S, N, C₆-C₁₀ aryl, and C₄-C₁₀ heteroaryl containing at least one heteroatom selected from the group consisting of O, S, and N;
R₆ is selected from the group consisting of H, —(CH₂)$_t$—CH(NH—C(CH₃)(=O))—(CH₂)$_t$—R₉, —C(=O)—X₂—R₁₀, and one or more substituted or unsubstituted amino acids, wherein the one or more substituted or unsubstituted amino acids is bound to the nitrogen atom adjacent to R₆ through a carboxyl moiety of the one or more substituted or unsubstituted amino acids, wherein X₂ is present or absent and, when present, is selected from the group consisting of —O—, —O—(CH₂)$_q$—, —(CH₂)$_t$—, and —(CH₂)$_v$—CH=CH—(CH₂)$_v$—, wherein q and t are each independently selected from the group consisting of 1, 2, 3, 4, 5, 6, 7, and 8, each v is independently selected from the group consisting of 0, 1, 2, 3, 4, 5, 6, 7, and 8, and R₉ and R₁₀ are each independently selected from the group consisting of straight chain or branched alkyl, heteroalkyl, cycloalkyl, heterocycloalkyl, aryl, and heteroaryl; and R₈ is selected from the group consisting of H and —C(=O)—R₁₁, wherein R₁₁ is substituted or unsubstituted C₁-C₆;

or an ester or pharmaceutically acceptable salt thereof.

In another aspect provided is a compound having any one of formulae (Ib)-(Ie):

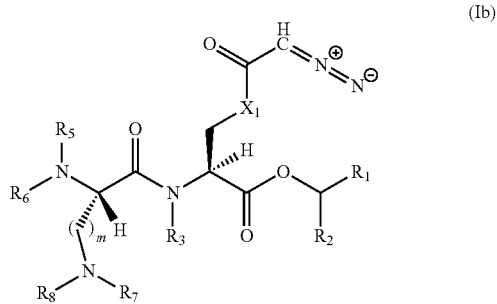

(Ib)

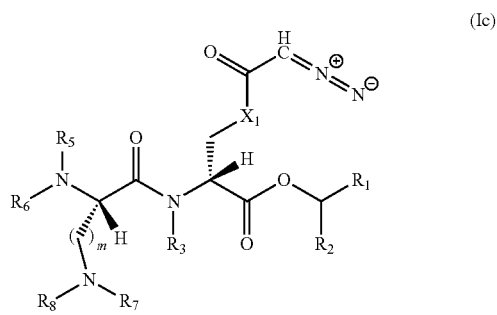

(Ic)

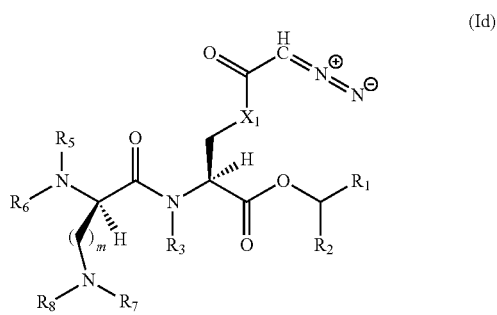

(Id)

-continued

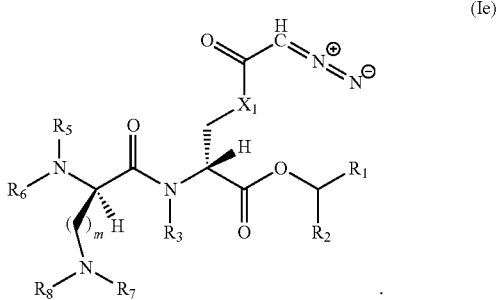

(Ie)

wherein $R_1$-$R_3$ and $R_5$-$R_8$ are as defined in connection with Formula (Ia).

Also provided is a pharmaceutical composition comprising the compound of the disclosure and a pharmaceutically acceptable carrier, diluent or excipient. In one embodiment, the pharmaceutical composition further comprises at least one oncological, immunological, anti-infectious, or neurological agent.

Also provided is a method for treating an oncological, immunological, infectious or neurological disease or disorder, the method comprising administering to a subject in need of treatment thereof a therapeutically effective amount of a compound of the disclosure or the pharmaceutical composition thereof.

In one embodiment, the oncological, immunological, infectious or neurological disease or disorder is cancer. In another embodiment, the oncological, immunological, infectious or neurological disease or disorder is a bacterial or viral infection. In another embodiment, the oncological, immunological, infectious or neurological disease or disorder is an autoimmune disease, immune disorder or inflammatory disorder. In another embodiment, the oncological, immunological, infectious or neurological disease or disorder is cancer a neurodegenerative disorder. In another embodiment, the method further comprises administering a therapeutically effective amount of at least one second agent that is useful for the treatment of the oncological, immunological, infectious or neurological disease or disorder.

In another embodiment, provided is a method of enhancing the effects of an immune checkpoint inhibitor, enabling a subject to respond to an immune checkpoint inhibitor, or enabling the toxicity or the dose or number of treatments with an immune checkpoint inhibitor to be reduced, comprising administering to a subject in need of treatment thereof a therapeutically effective amount of a compound of a compound of the disclosure or the pharmaceutical composition thereof, and an immune checkpoint inhibitor.

In another embodiment, provided is a method for treating an oncological, immunological, infectious or neurological disease or disorder that is refractory to an immune checkpoint inhibitor therapy, the method comprising administering to a subject in need thereof, and having the refractory disease or disorder, a therapeutically effective amount of a compound of the disclosure or the pharmaceutical composition thereof.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1A:
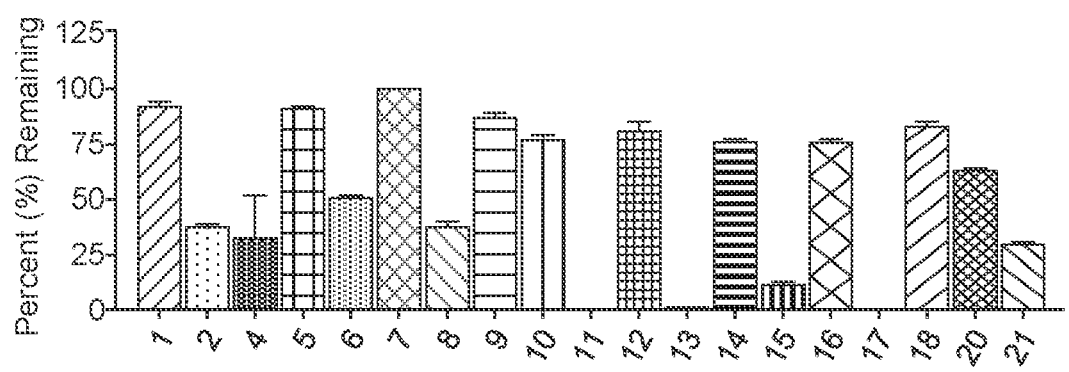

Having thus described the presently disclosed subject matter in general terms, reference will now be made to the accompanying Figures, which are not necessarily drawn to scale, and wherein:

FIG. 1A is a bar graph showing the stability of intact compounds 1-21 after incubation for 60 minutes in the presence of pig intestinal homogenate.

Figure 1B:
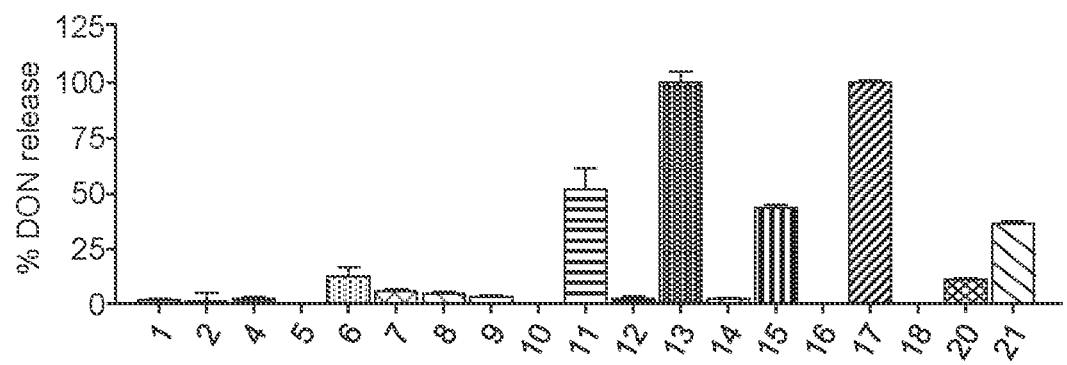

FIG. 1B is a bar graph showing the extent of DON release when compounds 1-21 are incubated for 60 minutes in the presence of pig intestinal homogenate.

Figure 2A:
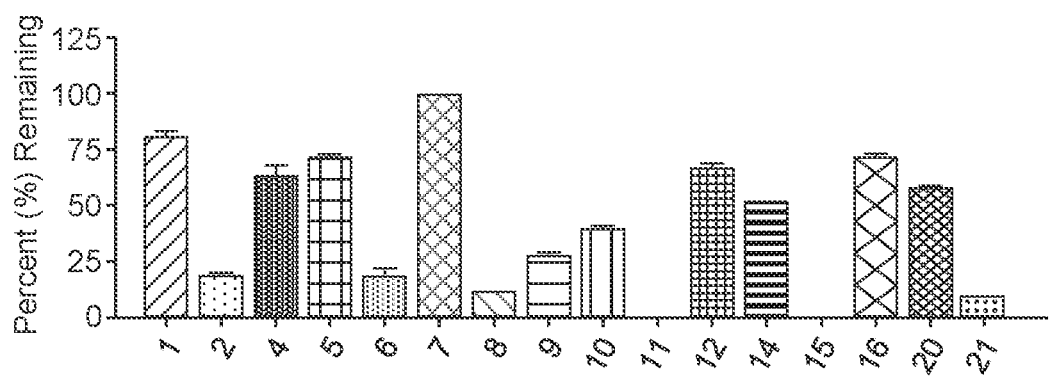

FIG. 2A is a bar graph showing the stability of intact compounds 1-21 after incubation for 60 minutes in the presence of pig liver homogenate.

Figure 2B:
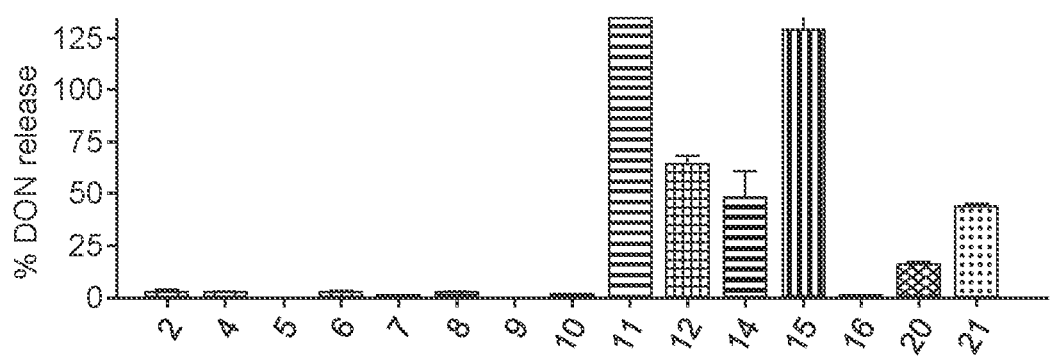

FIG. 2B is a bar graph showing the extent of DON release when compounds 1-21 are incubated for 60 minutes in the presence of pig liver homogenate.

Figure 3A:
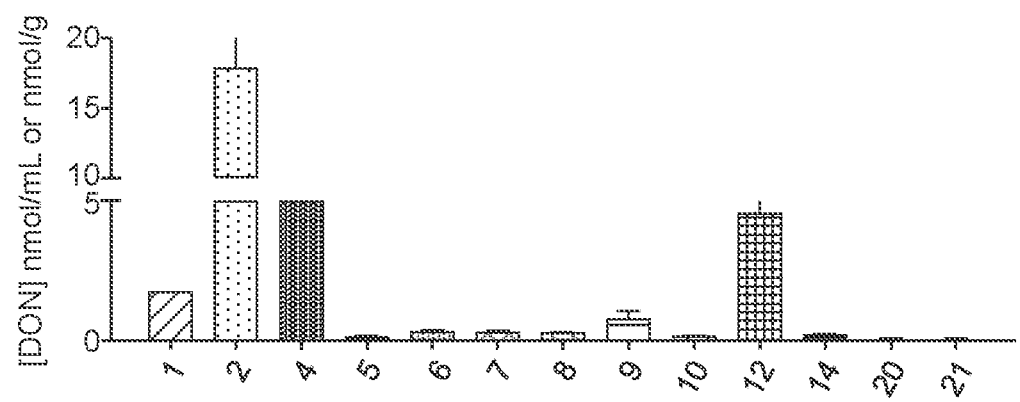

FIG. 3A is a bar graph showing concentrations of DON in P493 tumor cells after compounds 1-21 were incubated in human plasma containing P493 tumor cells.

Figure 3B:
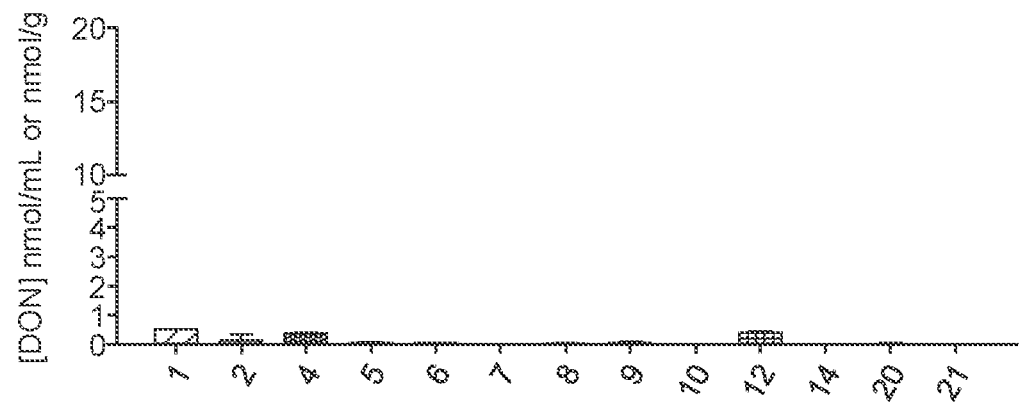

FIG. 3B is a bar graph showing concentrations of DON in plasma after compounds 1-21 were incubated in human plasma containing P493 tumor cells.

Figure 4A:
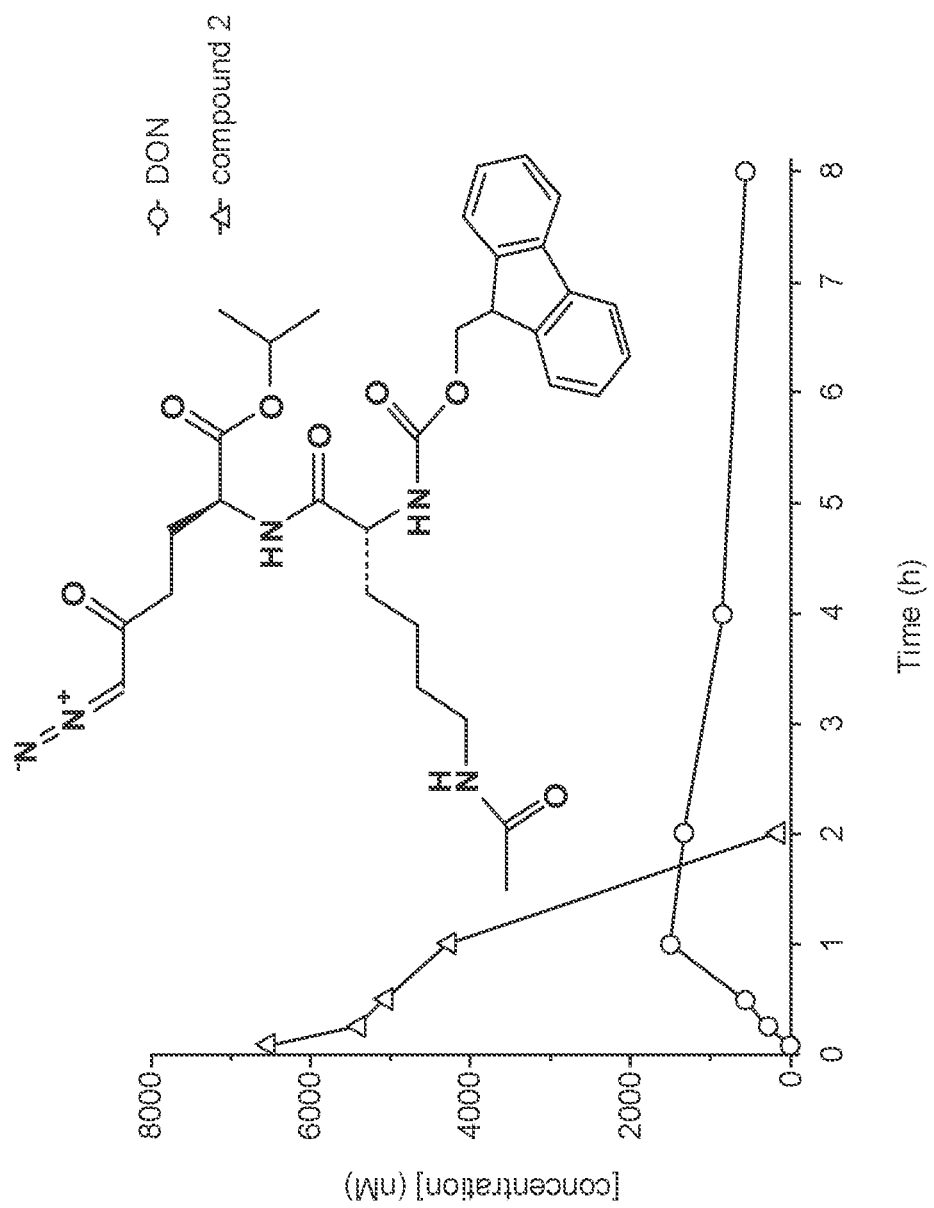

FIG. 4A is a graph showing the concentrations of DON and compound 2 over time after intravenous (IV) infusion.

Figure 4B:
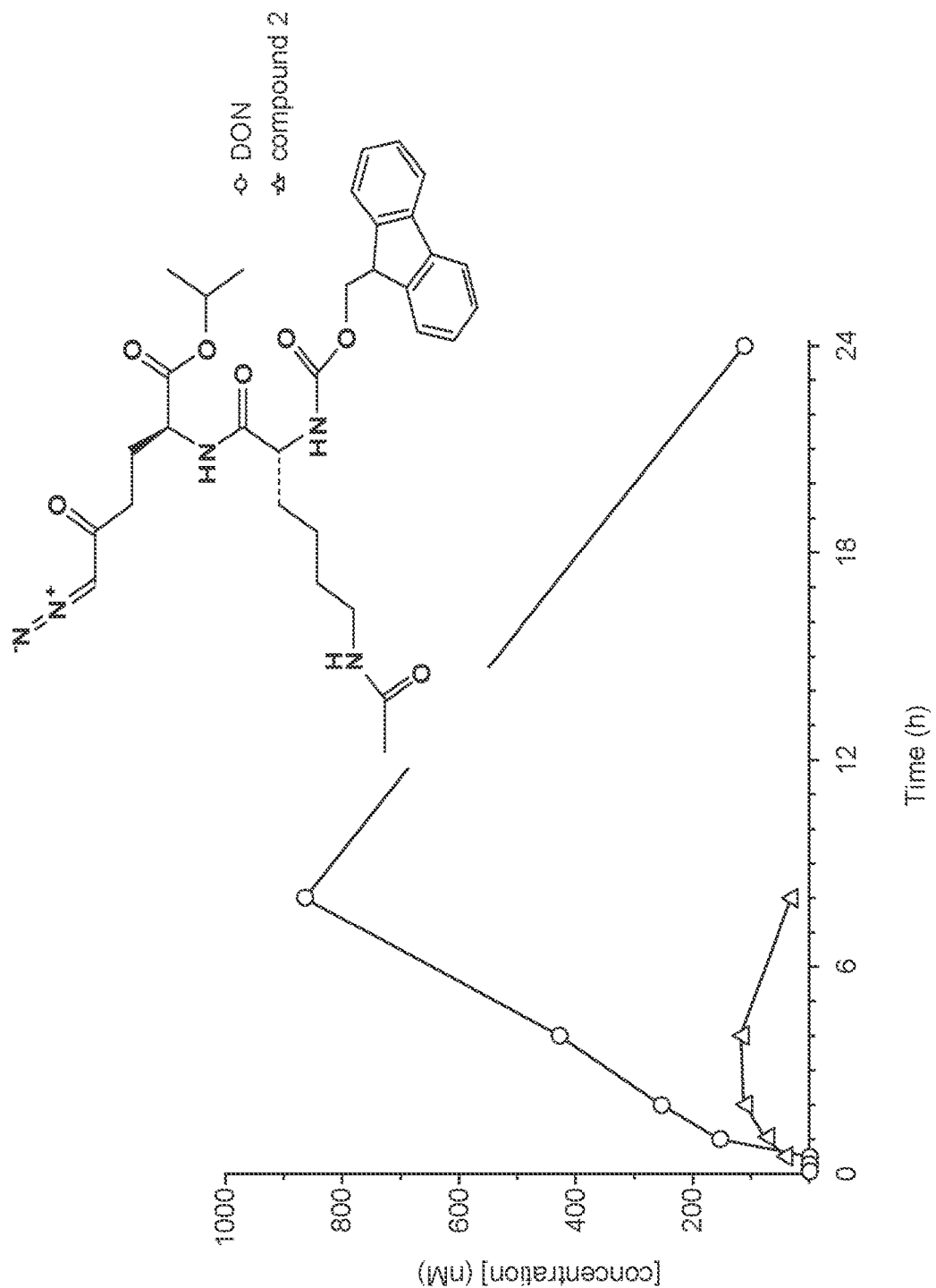

FIG. 4B is a graph showing the concentrations of DON and compound 2 over time after subcutaneous (SC) administration.

Figure 4C:
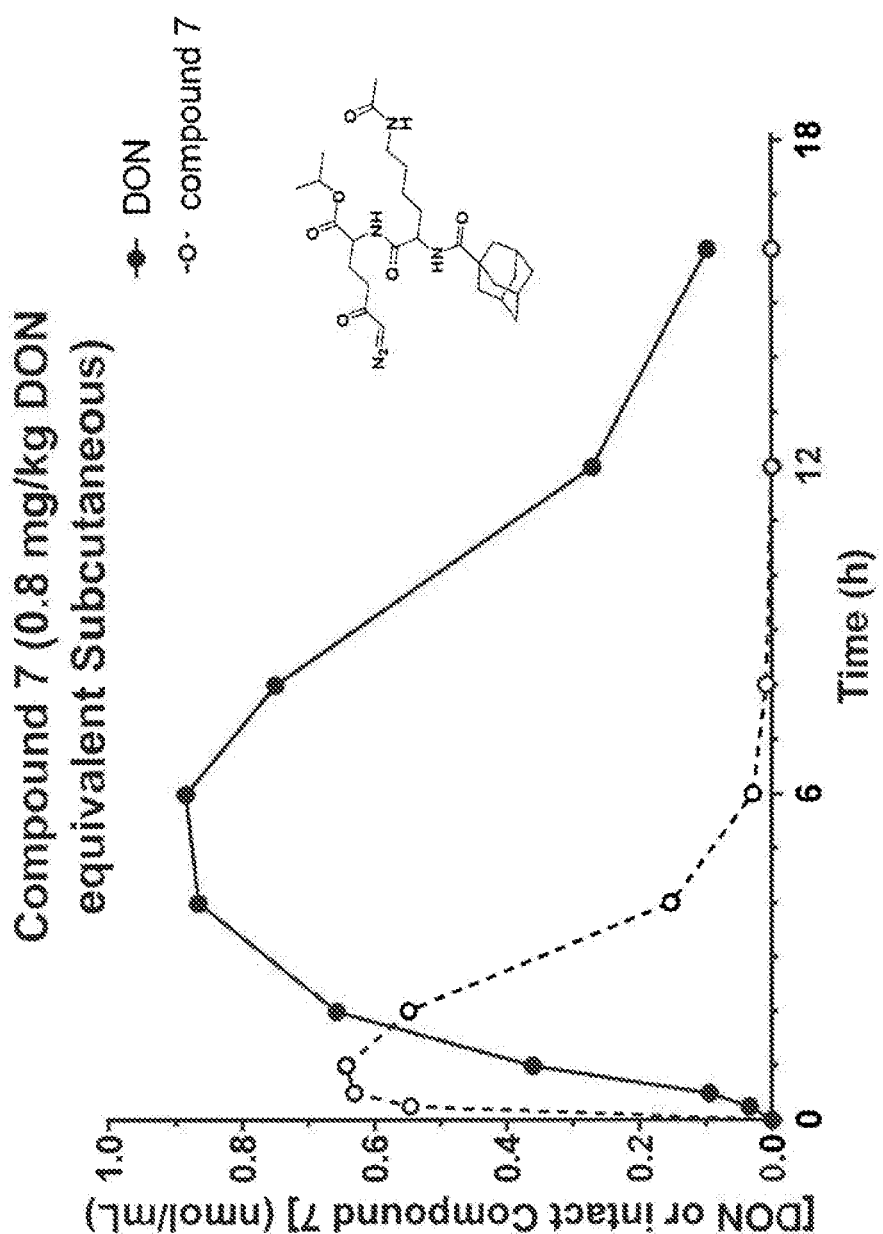

FIG. 4C is a line graph showing compound 7 plasma pharmacokinetics in beagle dog following SC administration.

Figure 5A:
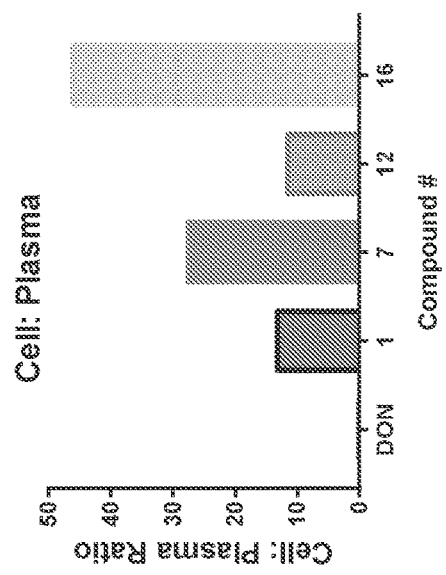

FIG. 5A is a bar graph showing tumor cell DON concentrations following incubation of compounds in a mix of human plasma with 10 million lymphoma (P493B) cells. Compounds 1, 7, and 12 showed DON release in tumor cells similar to DON. Compound 16 showed minimal release.

Figure 5B:
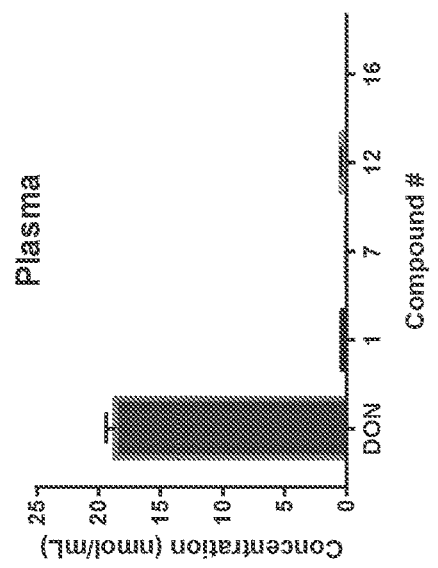

FIG. 5B is a bar graph showing that compounds 1, 7, 12, and 16 released minimal DON in plasma following a 1 h incubation.

Figure 5C:
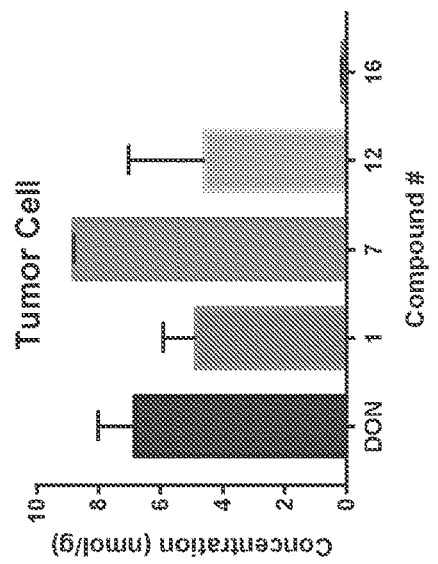

FIG. 5C is a bar graph showing that compound having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Tumor Targeted Glutamine Antagonists

The presently disclosed subject matter, in part, is directed toward glutamine antagonists for oncological, immunological, and neurological uses. The presently disclosed compounds were unexpectedly found to deliver the glutamine antagonist (e.g., DON) preferentially to human tumor cells versus plasma, with significantly less glutamine antagonist exposure in liver and gut (the presumed toxicity organ). Without wishing to be bound to any one particular theory, it is thought that the observed preferential tumor delivery is based on tumor enriched enzymes, including plasmin, Cathepsins, and histone deactylases (HDACs), which are responsible for cleaving the designed promoeities. This characteristic will permit the dosing of the presently disclosed compounds to patients with preferential glutamine antagonist delivery to the tumor, less systemic exposure, resulting in a greatly enhanced therapeutic window.

The glutamine antagonists were prepared by masking the amine and/or the carboxylate functionalities to alter the pharmacokinetics of DON providing slower release kinetics and cellular targeting to enhance tolerability. Further, the compounds, in some embodiments, selectively target the active glutamine antagonists to specific cells or provide a slower release of DON and thus decrease the toxicity of the drug molecule.

It has been discovered that that masking both the α-amino group and the carboxy-functionality enhances stability and oral bioavailability. The presently disclosed compounds also exhibit a stability that is comparable to that of free DON.

Structures of representative compounds of the disclosure are provided in Table 1.

| Compound | Structure |
| --- | --- |
| 1 | 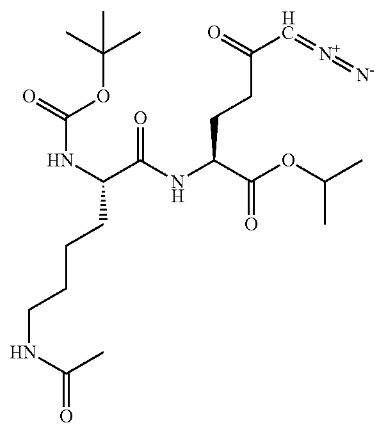 [SMILES: CC(=O)NCCCC[C@H](NC(=O)OC(C)(C)C)C(=O)N[C@@H](CCC(=O)C=[N+]=[N-])C(=O)OC(C)C] |
| 2 | 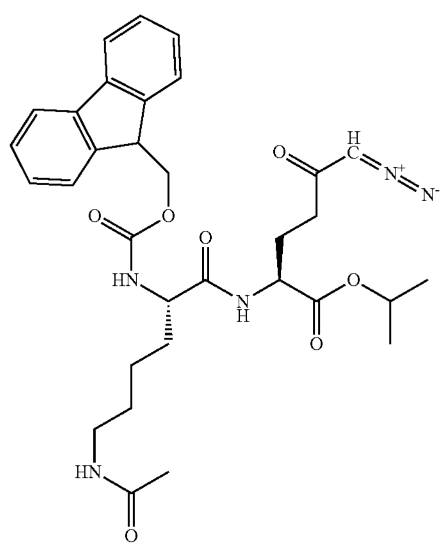 [SMILES: CC(=O)NCCCC[C@H](NC(=O)OCC1c2ccccc2-c2ccccc21)C(=O)N[C@@H](CCC(=O)C=[N+]=[N-])C(=O)OC(C)C] |

-continued
| Compound | Structure |
|---|---|
| 3 | 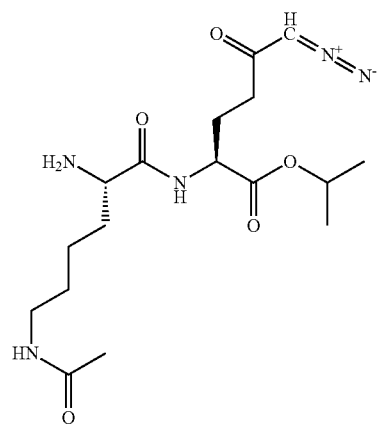 |
| 4 | 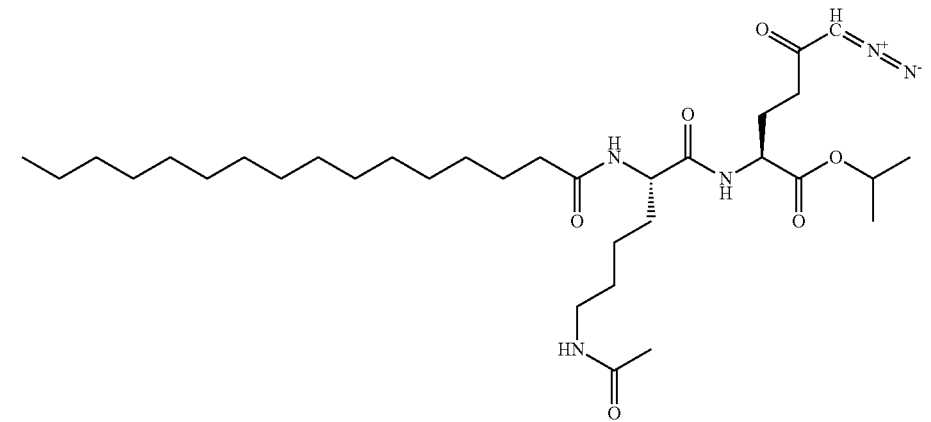 [SMILES: CCCCCCCCCCCCCCCC(=O)N[C@@H](CCCCNC(C)=O)C(=O)N[C@@H](CCC(=O)C=[N+]=[N-])C(=O)OC(C)C] |
| 5 | 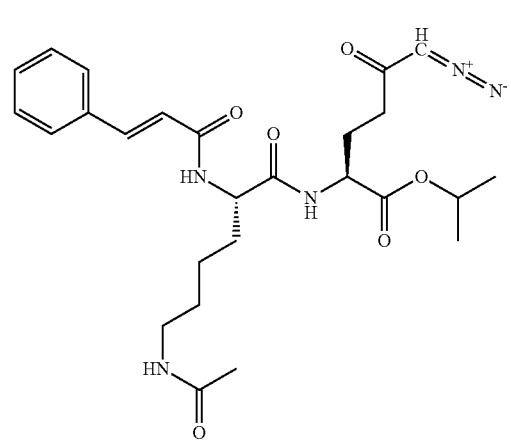 [SMILES: CC(=O)NCCCC[C@H](NC(=O)/C=C/c1ccccc1)C(=O)N[C@@H](CCC(=O)C=[N+]=[N-])C(=O)OC(C)C] |

| Compound | Structure |
|---|---|
| 6 | 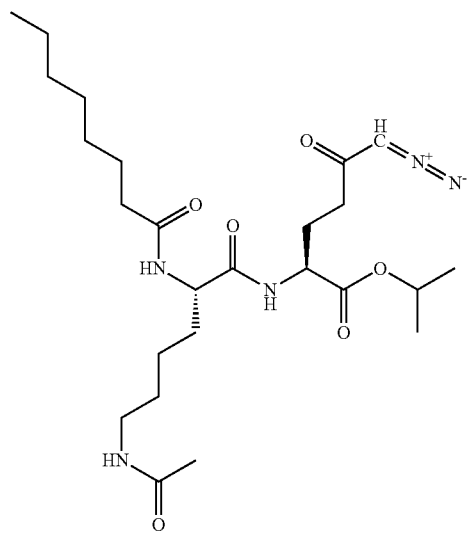 [SMILES: CCCCCCCC(=O)N[C@@H](CCCCNC(C)=O)C(=O)N[C@@H](CCC(=O)C=[N+]=[N-])C(=O)OC(C)C] |
| 7 | 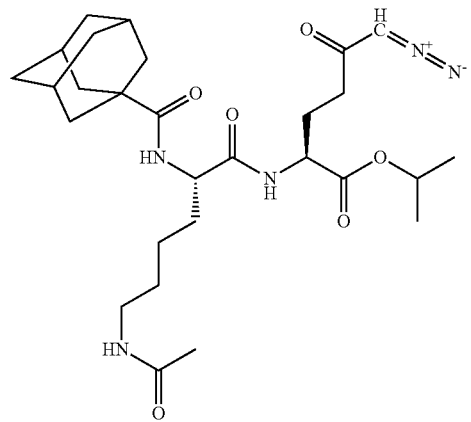 [SMILES: CC(=O)NCCCC[C@H](NC(=O)C12CC3CC(CC(C3)C1)C2)C(=O)N[C@@H](CCC(=O)C=[N+]=[N-])C(=O)OC(C)C] |
| 8 | 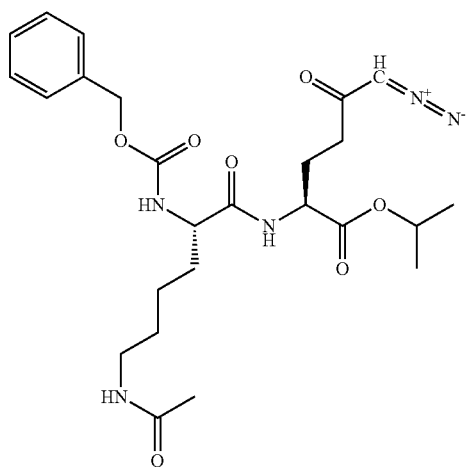 [SMILES: CC(=O)NCCCC[C@H](NC(=O)OCc1ccccc1)C(=O)N[C@@H](CCC(=O)C=[N+]=[N-])C(=O)OC(C)C] |

| Compound | Structure |
|---|---|
| 9 | *(structure shown)* |
| 10 | *(structure shown)* |
| 11 | *(structure shown)* |

-continued
| Compound | Structure |
|---|---|
| 12 | 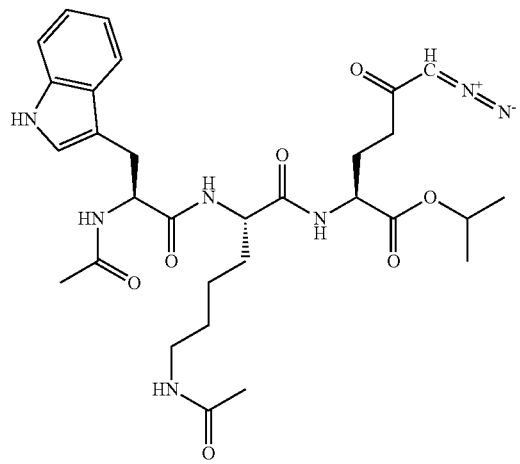 [SMILES: CC(=O)NCCCC[C@H](NC(=O)[C@H](Cc1c[nH]c2ccccc12)NC(C)=O)C(=O)N[C@@H](CCC(=O)C=[N+]=[N-])C(=O)OC(C)C] |
| 13 | 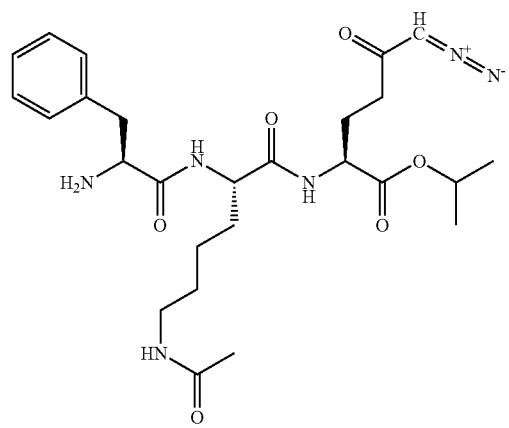 [SMILES: CC(=O)NCCCC[C@H](NC(=O)[C@@H](N)Cc1ccccc1)C(=O)N[C@@H](CCC(=O)C=[N+]=[N-])C(=O)OC(C)C] |
| 14 | 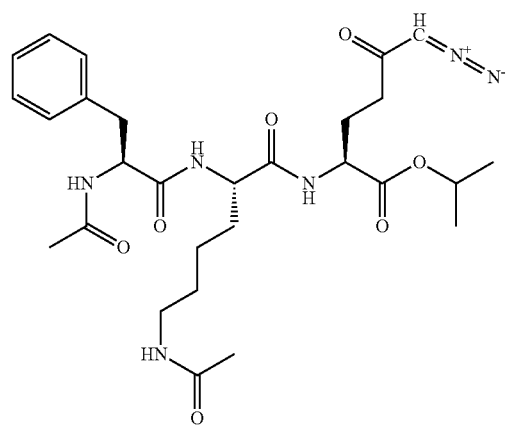 [SMILES: CC(=O)NCCCC[C@H](NC(=O)[C@H](Cc1ccccc1)NC(C)=O)C(=O)N[C@@H](CCC(=O)C=[N+]=[N-])C(=O)OC(C)C] |

-continued
| Compound | Structure |
|---|---|
| 15 | 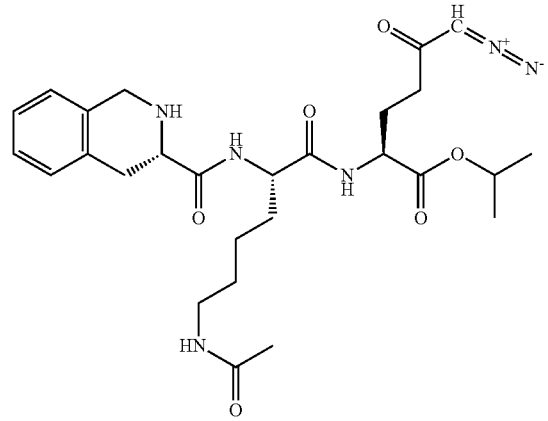 [SMILES: CC(=O)NCCCC[C@H](NC(=O)[C@@H]1Cc2ccccc2CN1)C(=O)N[C@@H](CCC(=O)C=[N+]=[N-])C(=O)OC(C)C] |
| 16 | 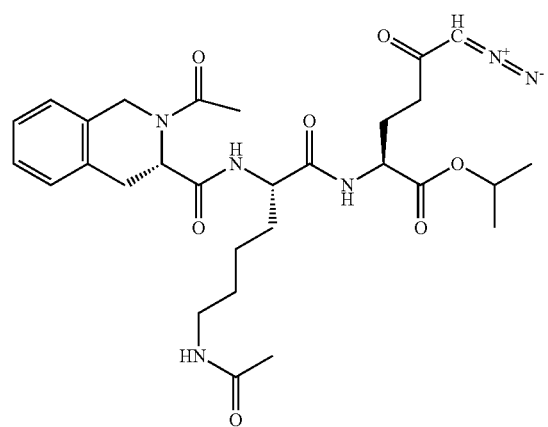 [SMILES: CC(=O)NCCCC[C@H](NC(=O)[C@@H]1Cc2ccccc2CN1C(C)=O)C(=O)N[C@@H](CCC(=O)C=[N+]=[N-])C(=O)OC(C)C] |
| 17 | 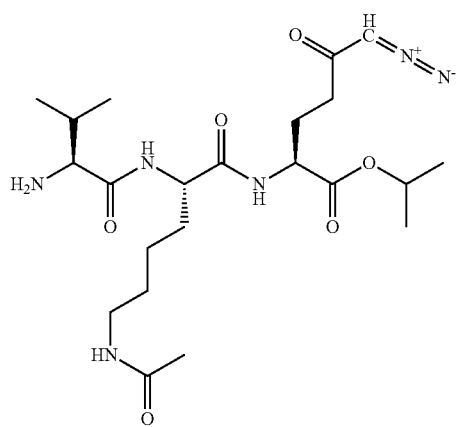 [SMILES: CC(=O)NCCCC[C@H](NC(=O)[C@@H](N)C(C)C)C(=O)N[C@@H](CCC(=O)C=[N+]=[N-])C(=O)OC(C)C] |

| Compound | Structure |
|---|---|
| 18 | 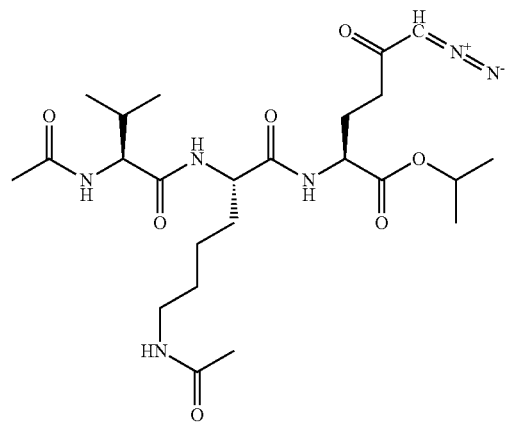 [SMILES: CC(=O)NCCCC[C@H](NC(=O)[C@@H](NC(C)=O)C(C)C)C(=O)N[C@@H](CCC(=O)C=[N+]=[N-])C(=O)OC(C)C] |
| 19 | 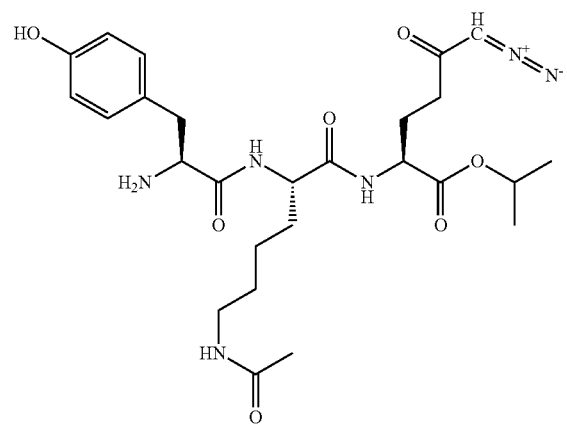 [SMILES: CC(=O)NCCCC[C@H](NC(=O)[C@@H](N)Cc1ccc(O)cc1)C(=O)N[C@@H](CCC(=O)C=[N+]=[N-])C(=O)OC(C)C] |
| 20 | 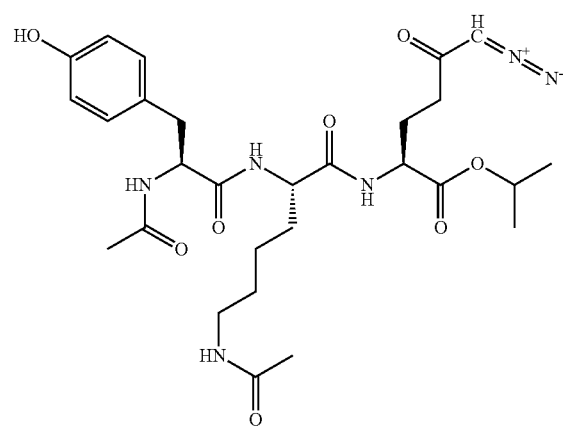 [SMILES: CC(=O)NCCCC[C@H](NC(=O)[C@H](Cc1ccc(O)cc1)NC(C)=O)C(=O)N[C@@H](CCC(=O)C=[N+]=[N-])C(=O)OC(C)C] |

| Compound | Structure |
|---|---|
| 21 | 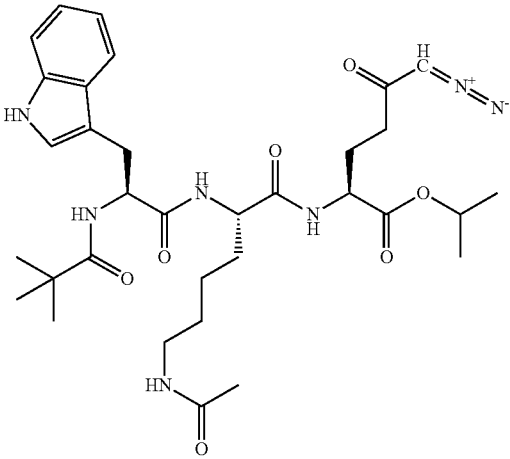 [SMILES: CC(=O)NCCCC[C@H](NC(=O)[C@H](Cc1c[nH]c2ccccc12)NC(=O)C(C)(C)C)C(=O)N[C@@H](CCC(=O)C=[N+]=[N-])C(=O)OC(C)C] |

Those skilled in the art will appreciate that the representative compounds shown in Table 1 combined with the guidance disclosed herein will enable those skilled in the art to synthesize compounds comprising other glutamine analogs, such as L-DONV, aza-serine, as are exemplified in the generic structures of formula (I). In other words, it should be understood that other glutamine antagonists, such as L-DONV, aza-serine, can be derivatized with the same substituents as the compounds shown in Table 1.

Accordingly, in some embodiments, provided is a compound having a structure of formula (I):

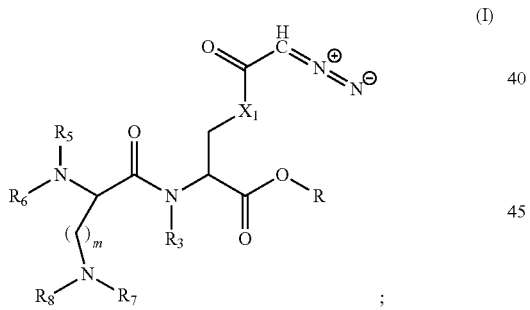

(I)

wherein:
m is an integer selected from the group consisting of 1, 2, 3, 4, 5, 6, 7, and 8;
$X_1$ is selected from the group consisting of —O— and —$(CH_2)_p$—, wherein p is an integer selected from the group consisting of 0, 1, 2, 3, 4, 5, 6, 7, and 8;
R is H, alkyl, substituted alkyl, cycloalkyl, substituted cycloalkyl, alkenyl, substituted alkenyl, alkynyl, substituted alkynyl, cycloalkenyl, substituted cycloalkenyl, tri(alkyl)ammonium, and tetra(alkyl)ammonium;
$R_3$, $R_5$, and $R_7$ are each independently H, $C_1$-$C_6$ alkyl, alkoxyl, cycloalkyl, heterocycloalkyl, aryl, and heteroaryl;
$R_6$ is selected from the group consisting of H, —$(CH_2)_t$CH(NH—C($CH_3$)(=O))—$(CH_2)_t$—$R_9$, —C(=O)—$X_2$—$R_{10}$, and one or more substituted or unsubstituted amino acids, wherein the one or more substituted or unsubstituted amino acids is bound to the nitrogen atom adjacent to $R_6$ through a carboxyl moiety of the one or more substituted or unsubstituted amino acids, wherein $X_2$ is present or absent and, when present, is selected from the group consisting of —O—, —O—$(CH_2)_q$—, —$(CH_2)_t$—, and —$(CH_2)_v$—CH=CH—$(CH_2)_v$—, wherein q and t are each independently selected from the group consisting of 1, 2, 3, 4, 5, 6, 7, and 8, each v is independently selected from the group consisting of 0, 1, 2, 3, 4, 5, 6, 7, and 8, and $R_9$ and $R_{10}$ are each independently selected from the group consisting of straight chain or branched alkyl, heteroalkyl, cycloalkyl, heterocycloalkyl, aryl, and heteroaryl; and
$R_8$ is selected from the group consisting of H and —C(=O)—$R_{11}$, wherein $R_{11}$ is substituted or unsubstituted alkyl;
or an ester or pharmaceutically acceptable salt thereof.

In some embodiments, provided is a compound having a structure of formula (Ia):

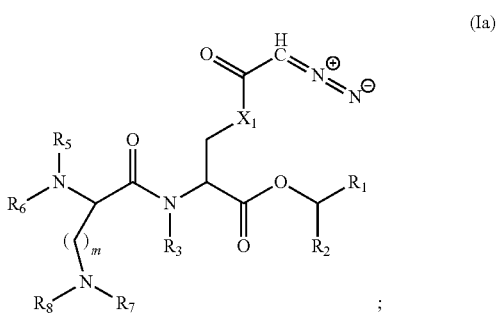

(Ia)

wherein:
m is an integer selected from the group consisting of 1, 2, 3, 4, 5, 6, 7, and 8;
$X_1$ is selected from the group consisting of —O— and —$(CH_2)_p$—, wherein p is an integer selected from the group consisting of 1, 2, 3, 4, 5, 6, 7, and 8;
$R_1$ and $R_2$ are each independently selected from the group consisting of H, alkyl, substituted alkyl, cycloalkyl, substituted cycloalkyl, alkenyl, substituted alkenyl, alkynyl, substituted alkynyl, cycloalkenyl, substituted cycloalkenyl, tri(alkyl)ammonium, and tetra(alkyl)ammonium, wherein $R_1$ and $R_2$ can be the same or different, or $R_1$ and $R_2$ can together form a $C_3$-$C_6$ cycloalkyl;

$R_3$, $R_5$, and $R_7$ are each independently selected from the group consisting of H, $C_1$-$C_6$ alkyl, alkoxyl, cycloalkyl, heterocycloalkyl, aryl, and heteroaryl;

$R_6$ is selected from the group consisting of H, —$(CH_2)_t$—CH(NH—C(CH_3)(=O))—$(CH_2)_t$—$R_9$, —C(=O)—$X_2$—$R_{10}$, and one or more substituted or unsubstituted amino acids, wherein the one or more substituted or unsubstituted amino acids is bound to the nitrogen atom adjacent to $R_6$ through a carboxyl moiety of the one or more substituted or unsubstituted amino acids, wherein $X_2$ is present or absent and, when present, is selected from the group consisting of —O—, —O—$(CH_2)_q$—, —$(CH_2)_t$—, and —$(CH_2)_v$—CH=CH—$(CH_2)_v$—, wherein q and t are each independently selected from 1, 2, 3, 4, 5, 6, 7, and 8, each v is independently selected from the group consisting of 0, 1, 2, 3, 4, 5, 6, 7, and 8, and $R_9$ and $R_{10}$ are each independently selected from the group consisting of straight chain or branched alkyl, heteroalkyl, cycloalkyl, heterocycloalkyl, aryl, or heteroaryl; and $R_8$ is selected from the group consisting of H and —C(=O)—$R_{11}$, wherein $R_{11}$ is substituted or unsubstituted;

or an ester or pharmaceutically acceptable salt thereof.

In some embodiments, the compound has a structure of any one of formulae (Ib)-(Ie):

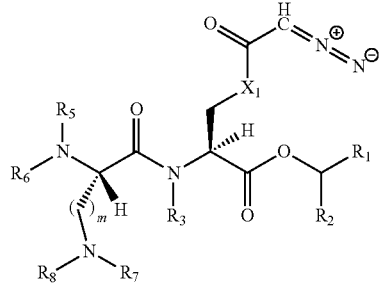
(Ib)

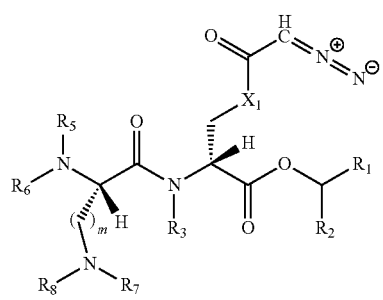
(Ic)

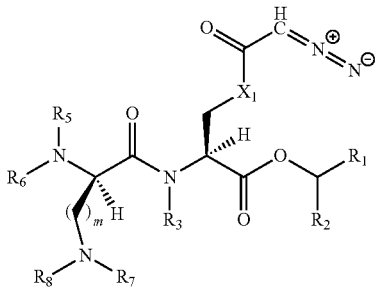
(Id)

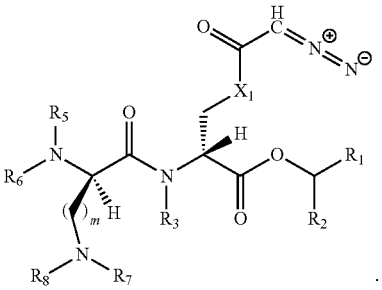
(Ie)

wherein $R_1$-$R_3$ and $R_5$-$R_8$ are as defined in connection with formula (Ia).

In other embodiments, the compound has a structure of formula (If):

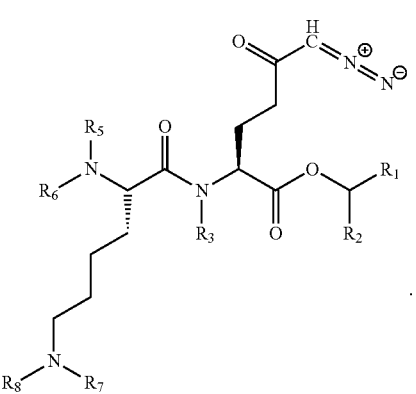
(If)

In particular embodiments, the compound has a structure of formula (Ig):

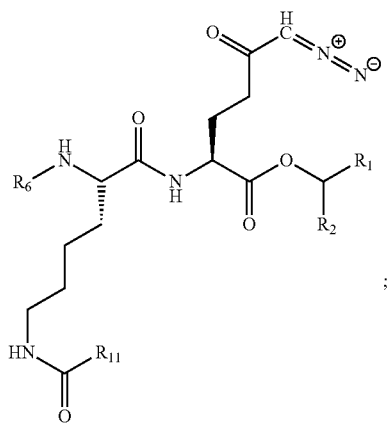

(Ig)

wherein $R_1$, $R_2$, and $R_{11}$ are each independently alkyl.

In even yet more particular embodiments, the compound has a structure of formula (Ih):

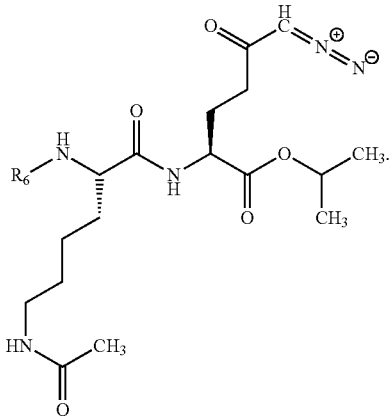

(Ih)

In some embodiments, $R_6$ is H and the compound is:

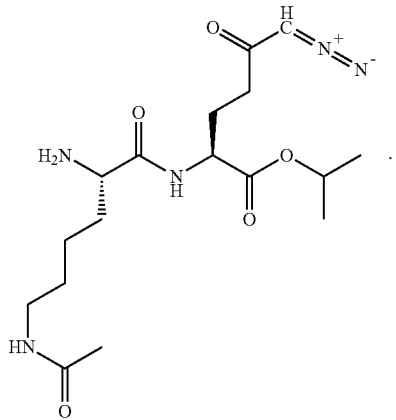

In some embodiments, $R_6$ is —(CH$_2$)$_t$CH(NH—C(CH$_3$)(=O))—(CH$_2$)$_t$—R$_9$. In certain embodiments, each t is 1 and $R_9$ is aryl. In particular embodiments, the compound is:

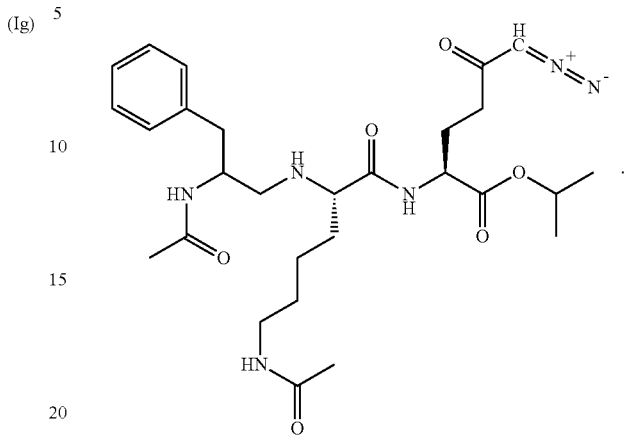

In other embodiments, $R_6$ is —C(=O)—X$_2$—R$_{10}$. In certain embodiments, X$_2$ is present and is —O—. In particular embodiments, $R_{10}$ is selected from the group consisting of t-butyl and adamantanyl. In more particular embodiments, the compound is:

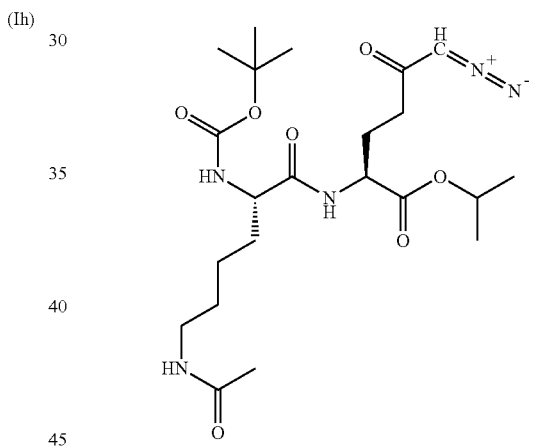

or

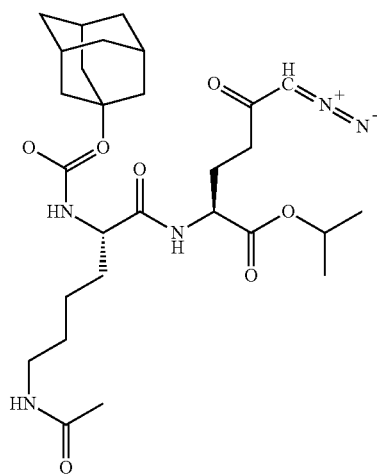

In other embodiments, $X_2$ is present and is —O—$(CH_2)_q$—. In certain embodiments, q is 1 and $R_{10}$ is selected from the group consisting of 1H-fluoren-9-yl and phenyl. In particular embodiments, the compound is:

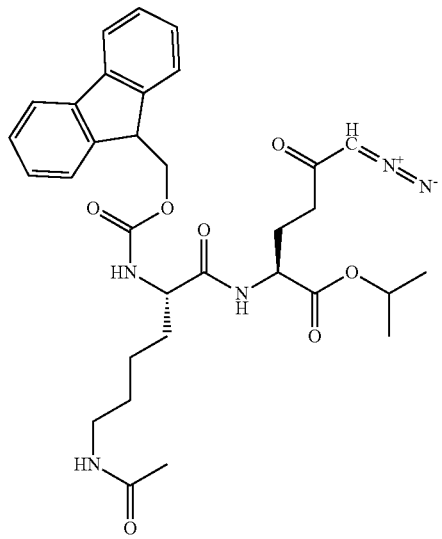

or

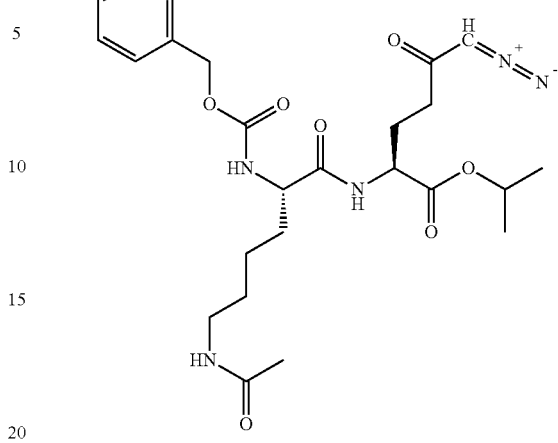

In other embodiments, $X_2$ is absent and $R_{10}$ is selected from the group consisting of $C_2$-$C_{20}$ alkyl and adamantanyl, 1,2,3,4-tetrahydroisoquinolinyl, pyridinyl, and substituted decahydrophenanthrene. In particular embodiments, the compound is:

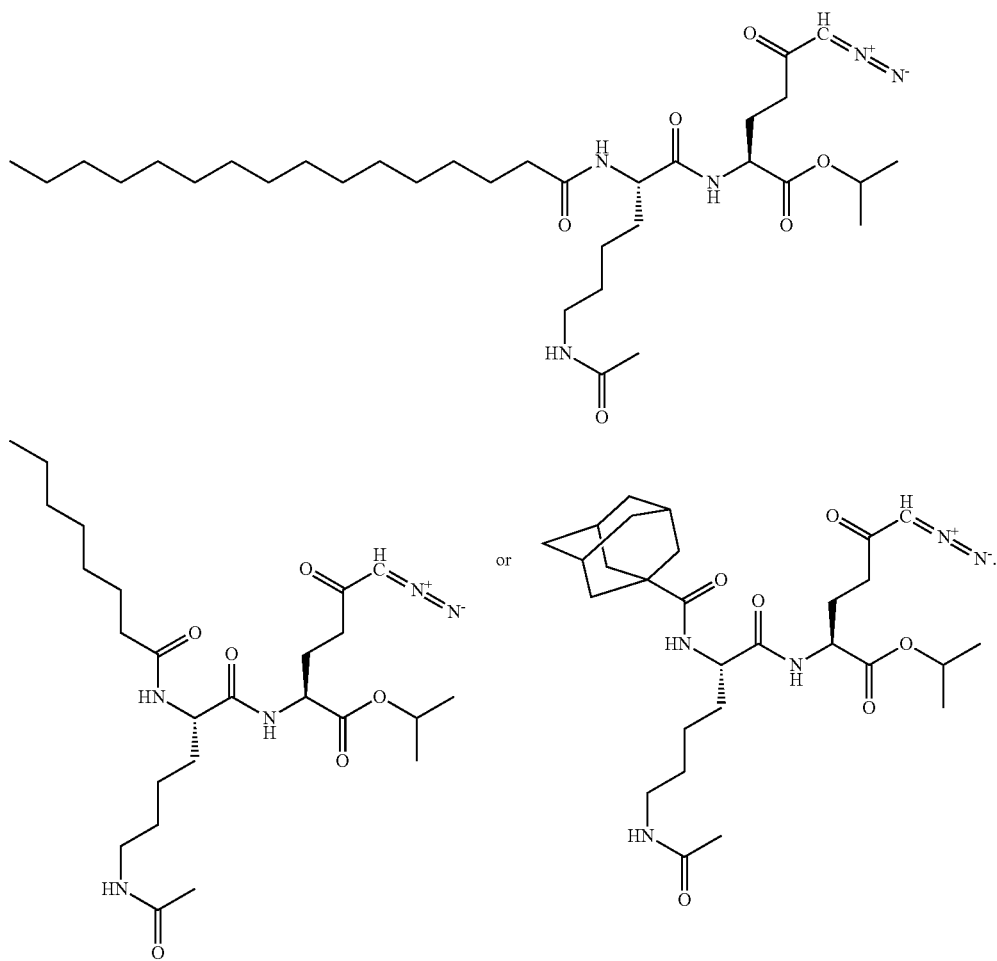

In some embodiments, $X_2$ is —$(CH_2)_t$— and $R_{10}$ is 1H-indol-3-yl. In particular embodiments, the compound is:
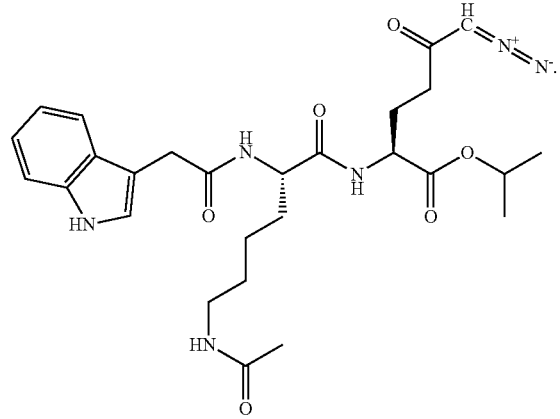
In some embodiments, $X_2$ is —$(CH_2)_s$ CH=CH—$(CH_2)_v$— and $R_{10}$ is aryl. In particular embodiments, the compound is:
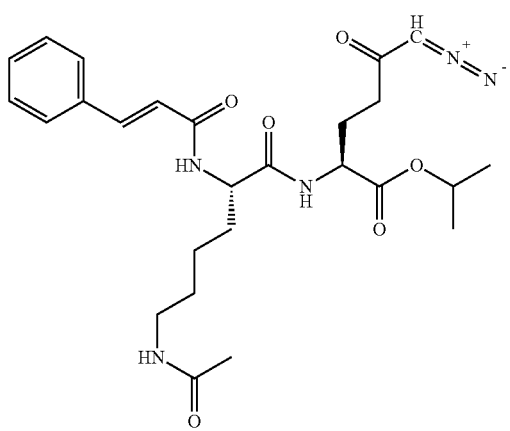
In some embodiments, $R_6$ is one or more substituted or unsubstituted amino acids. In particular embodiments, the compound is:
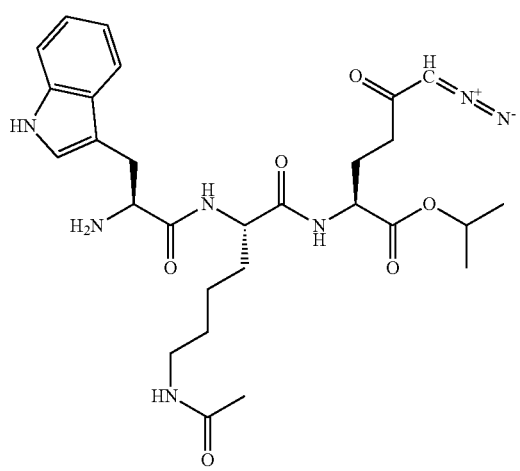
-continued
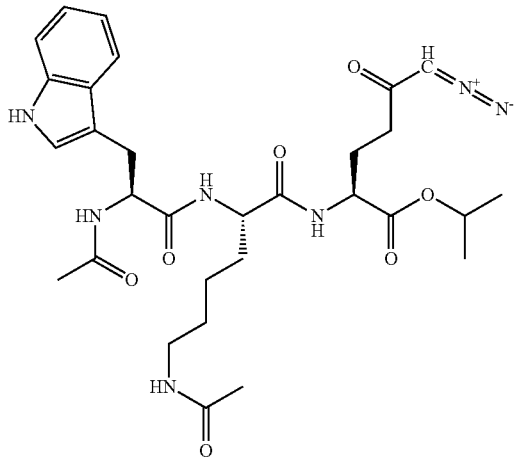
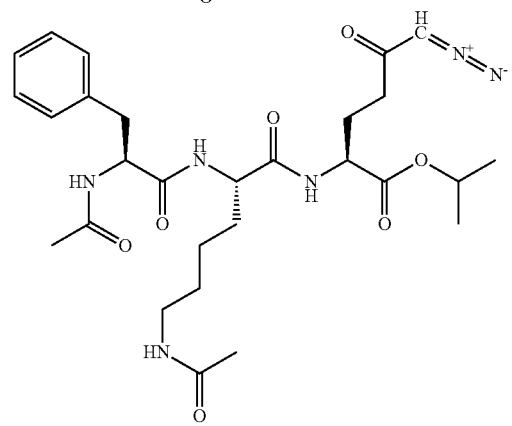
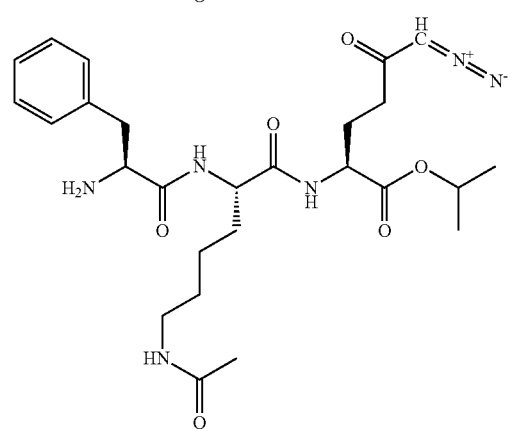
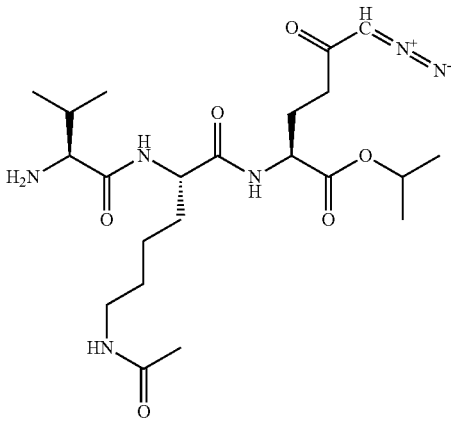

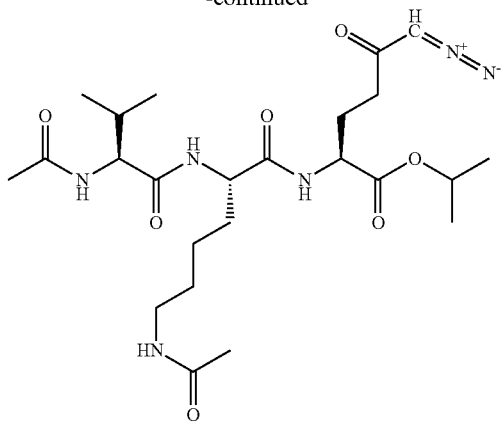

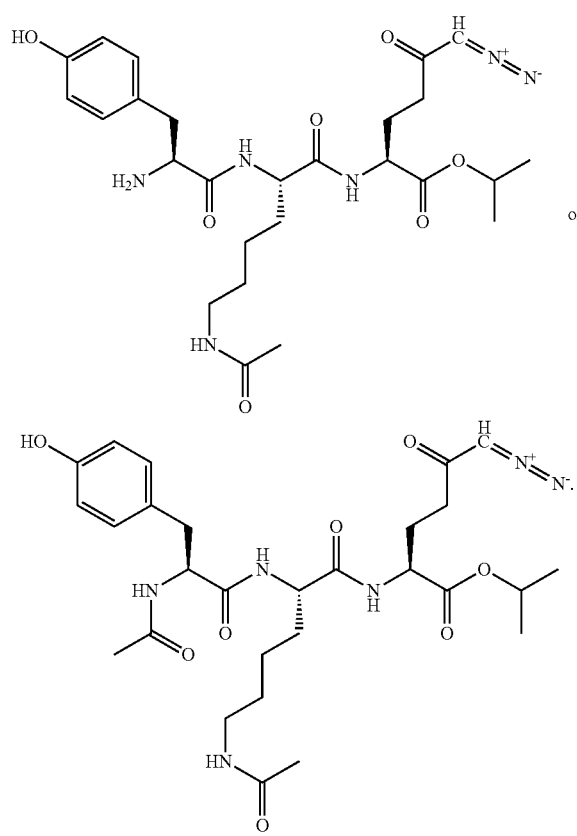

As used herein, the term "amino acid" includes moieties having a carboxylic acid group and an amino group. The term amino acid thus includes both natural amino acids (including proteinogenic amino acids) and non-natural amino acids. The term "natural amino acid" also includes other amino acids that can be incorporated into proteins during translation (including pyrrolysine and selenocysteine). Additionally, the term "natural amino acid" also includes other amino acids, which are formed during intermediary metabolism, e.g., ornithine generated from arginine in the urea cycle. The natural amino acids are summarized in Table 2:

TABLE 2

| Natural Amino Acids (Used For Protein Biosynthesis) | | |
|---|---|---|
| Amino acid | 3 letter code | 1-letter code |
| Alanine | ALA | A |
| Cysteine | CYS | C |
| Aspartic Acid | ASP | D |
| Glutamic Acid | GLU | E |
| Phenylalanine | PHE | F |
| Glycine | GLY | G |
| Histidine | HIS | H |
| Isoleucine | ILE | I |
| Lysine | LYS | K |
| Leucine | LEU | L |
| Methionine | MET | M |
| Asparagine | ASN | N |
| Proline | PRO | P |
| Glutamine | GLN | Q |
| Arginine | ARG | R |
| Serine | SER | S |
| Threonine | THR | T |
| Valine | VAL | V |
| Tryptophan | TRP | W |
| Tyrosine | TYR | Y |

The natural or non-natural amino acid may be optionally substituted. In one embodiment, the amino acid is selected from the group consisting of proteinogenic amino acids. Proteinogenic amino acids include glycine, alanine, valine, leucine, isoleucine, aspartic acid, glutamic acid, serine, threonine, glutamine, asparagine, arginine, lysine, proline, phenylalanine, tyrosine, tryptophan, cysteine, methionine and histidine. The term amino acid includes alpha amino acids and beta amino acids, such as, but not limited to, beta alanine and 2-methyl beta alanine. The term amino acid also includes certain lactam analogues of natural amino acids, such as, but not limited to, pyroglutamine. The term amino acid also includes amino acids homologues including homocitrulline, homoarginine, homoserine, homotyrosine, homoproline and homophenylalanine.

The terminal portion of the amino acid residue or peptide may be in the form of the free acid i.e., terminating in a —COOH group or may be in a masked (protected) form, such as in the form of a carboxylate ester or carboxamide. In certain embodiments, the amino acid or peptide residue terminates with an amino group. In an embodiment, the residue terminates with a carboxylic acid group —COOH or an amino group —NH$_2$. In another embodiment, the residue terminates with a carboxamide group. In yet another embodiment, the residue terminates with a carboxylate ester.

As disclosed hereinabove, the term "amino acid" includes compounds having a —COOH group and an —NH$_2$ group. A substituted amino acid includes an amino acid which has an amino group which is mono- or di-substituted. In particular embodiments, the amino group may be mono-substituted. (A proteinogenic amino acid may be substituted at another site from its amino group to form an amino acid which is a substituted proteinogenic amino acid). The term substituted amino acid thus includes N-substituted metabolites of the natural amino acids including, but not limited to, N-acetyl amino acids such as N-acetyl cysteine, N-acetyl serine, and N-acetyl threonine.

For example, the term "N-substituted amino acid" includes N-alkyl amino acids (e.g., $C_{1-6}$ N-alkyl amino acids, such as sarcosine, N-methyl-alanine, N-methyl-glutamic acid and N-tert-butylglycine), which can include $C_{1-6}$ N-substituted alkyl amino acids (e.g., N-(carboxy alkyl) amino acids (e.g., N-(carboxymethyl) amino acids) and N-methylcycloalkyl amino acids (e.g., N-methylcyclopropyl amino acids)); N,N-di-alkyl amino acids (e.g., N,N-di-$C_{1-6}$ alkyl amino acids (e.g., N,N-dimethyl amino acid)); N,N,N-tri-alkyl amino acids (e.g., N,N,N-tri-$C_{1-6}$ alkyl amino acids (e.g., N,N,N-trimethyl amino acid)); N-acyl amino acids (e.g., $C_{1-6}$ N-acyl amino acid); N-aryl amino acids (e.g., N-phenyl amino acids, such as N-phenylglycine); N-amidinyl amino acids (e.g., an N-amidine amino acid, i.e., an amino acid in which an amine group is replaced by a guanidino group).

The term "amino acid" also includes amino acid alkyl esters (e.g., amino acid $C_{1-6}$ alkyl esters); and amino acid aryl esters (e.g., amino acid phenyl esters).

For amino acids having a hydroxy group present on the side chain, the term "amino acid" also includes O-alkyl amino acids (e.g., $C_{1-6}$ O-alkyl amino acid ethers); O-aryl amino acids (e.g., O-phenyl amino acid ethers); O-acyl amino acid esters; and O-carbamoyl amino acids.

For amino acids having a thiol group present on the side chain, the term "amino acid" also includes S-alkyl amino acids (e.g., $C_{1-6}$ S-alkyl amino acids, such as S-methyl methionine, which can include $C_{1-6}$ S-substituted alkyl amino acids and S-methylcycloalkyl amino acids (e.g., S-methylcyclopropyl amino acids)); S-acyl amino acids (e.g., a $C_{1-6}$ S-acyl amino acid); S-aryl amino acid (e.g., a S-phenyl amino acid); a sulfoxide analogue of a sulfur-containing amino acid (e.g., methionine sulfoxide) or a sulfoxide analogue of an S-alkyl amino acid (e.g., S-methyl cystein sulfoxide) or an S-aryl amino acid.

Examples of non-proteinogenic amino acids include, but are not limited to: citrulline, hydroxyproline, 4-hydroxyproline, β-hydroxyvaline, ornithine, β-amino alanine, albizziin, 4-amino-phenylalanine, biphenylalanine, 4-nitro-phenylalanine, 4-fluoro-phenylalanine, 2,3,4,5,6-pentafluoro-phenylalanine, norleucine, cyclohexylalanine, α-aminoisobutyric acid, α-aminobutyric acid, α-aminoisobutyric acid, 2-aminoisobutyric acid, 2-aminoindane-2-carboxylic acid, selenomethionine, lanthionine, dehydroalanine, γ-amino butyric acid, naphthylalanine, aminohexanoic acid, pipecolic acid, 2,3-diaminoproprionic acid, tetrahydroisoquinoline-3-carboxylic acid, tert-leucine, tert-butylalanine, cyclopropylglycine, cyclohexylglycine, 4-aminopiperidine-4-carboxylic acid, diethylglycine, dipropylglycine and derivatives thereof wherein the amine nitrogen has been mono- or di-alkylated.

II. Methods of Synthesis

The compounds described herein may be synthesized according to the methods set out in the Examples as well as according to Scheme I.

Scheme 1

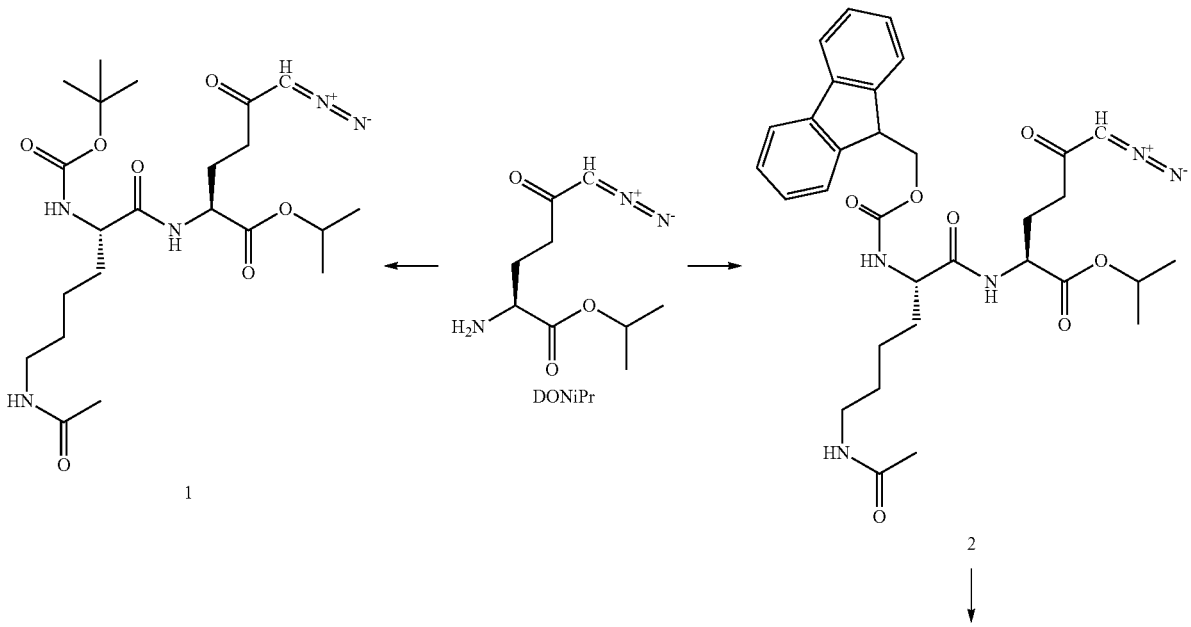

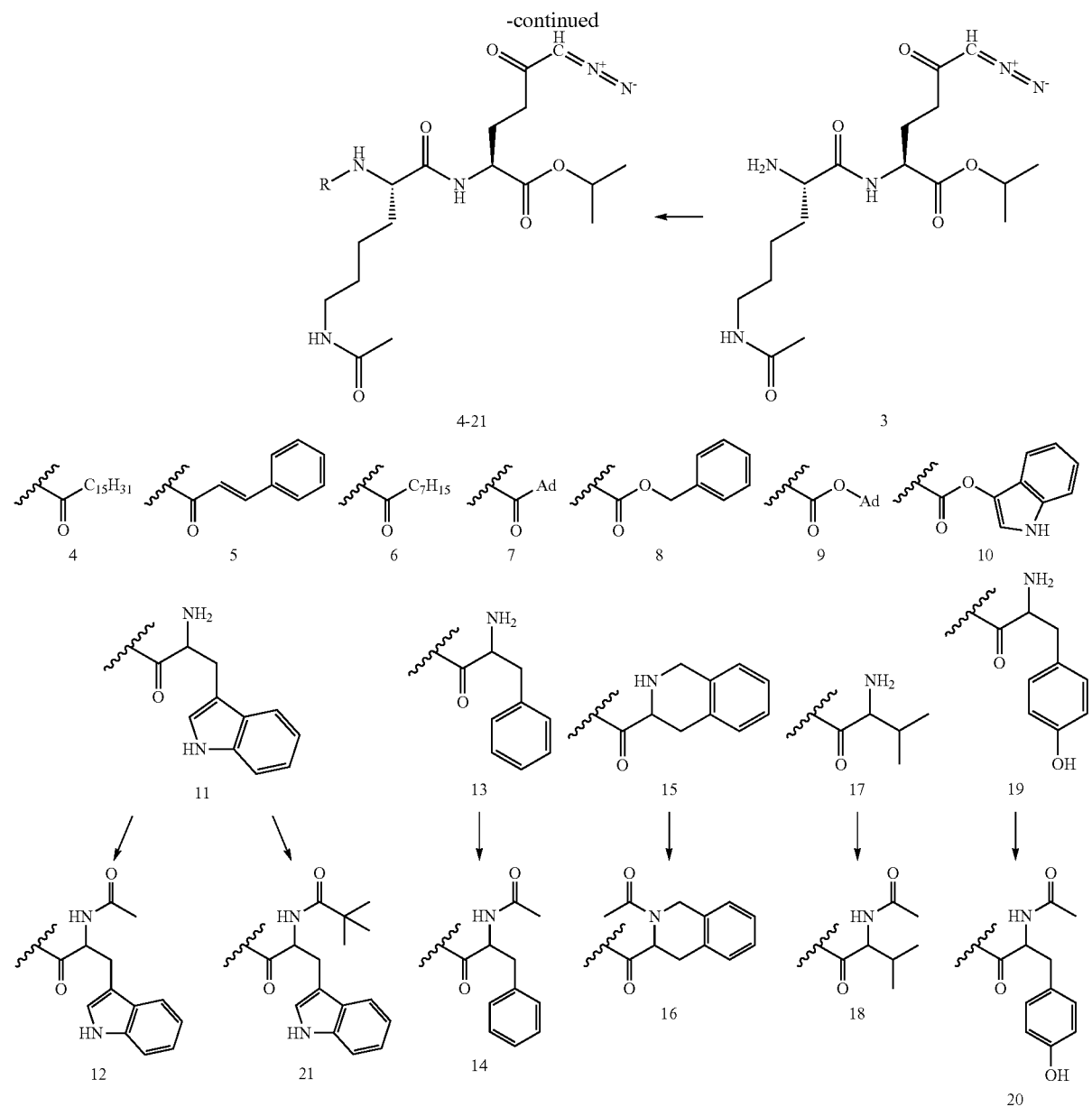

The moities of compounds 11-21 shown in the scheme above can have either an R-configuration or an S-configuration.

III. Pharmaceutical Compositions and Administration

In another aspect, provided is a pharmaceutical composition including one compound of formula (I), alone or in combination with one or more additional therapeutic agents in admixture with a pharmaceutically acceptable excipient. Accordingly, in some embodiments, the presently disclosed subject matter provides a pharmaceutical composition comprising a compound of formula (I), and a pharmaceutically acceptable carrier, diluent, or excipient. One of skill in the art will recognize that the pharmaceutical compositions include the pharmaceutically acceptable salts of the compounds described above.

Pharmaceutically acceptable salts are generally well known to those of ordinary skill in the art, and include salts of active compounds which are prepared with relatively nontoxic acids or bases, depending on the particular substituent moieties found on the compounds described herein. When compounds of the present disclosure contain relatively acidic functionalities, base addition salts can be obtained by contacting the neutral form of such compounds with a sufficient amount of the desired base, either neat or in a suitable inert solvent or by ion exchange, whereby one basic counterion (base) in an ionic complex is substituted for another. Examples of pharmaceutically acceptable base addition salts include sodium, potassium, calcium, ammonium, organic amino, or magnesium salt, or a similar salt.

When compounds of the present disclosure contain relatively basic functionalities, acid addition salts can be obtained by contacting the neutral form of such compounds with a sufficient amount of the desired acid, either neat or in a suitable inert solvent or by ion exchange, whereby one acidic counterion (acid) in an ionic complex is substituted for another. Examples of pharmaceutically acceptable acid addition salts include those derived from inorganic acids like hydrochloric, hydrobromic. nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-toluenesulfonic, citric, tartaric, methanesulfonic, and the like. Also included are salts of amino acids, such as arginate and the like, and salts of organic acids like glucuronic or galactunoric acids and the like (see, for example, Berge et al (1977)). Certain specific compounds of the present disclosure contain both basic and acidic functionalities that allow the compounds to be converted into either base or acid addition salts.

Accordingly, pharmaceutically acceptable salts suitable for use with the presently disclosed subject matter include, by way of example but not limitation, acetate, benzenesulfonate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide. isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy ($20^{th}$ ed.) Lippincott, Williams & Wilkins (2000).

In particular embodiments, the salt is a tri(alkyl)ammonium or tetra(alkyl)ammonium salt. In yet more particular embodiments, the salt is selected from the group consisting of a tri($C_1$-$C_8$-alkyl)ammonium. tetra($C_1$-$C_8$-alkyl)ammonium, triphenylammonium, tri(hydroxy-$C_1$-$C_8$-alkyl)ammonium, and tetra(hydroxy-$C_1$-$C_8$-alkyl)ammonium salt. In even more particular embodiments, the salt is selected from the group consisting of a trimethylammonium, triethylammonium, tri(hydroxyethyl)ammonium, tripropylammonium, and tri(hydroxypropyl)ammonium salt.

In therapeutic and/or diagnostic applications, the compounds of the disclosure can be formulated for a variety of modes of administration, including oral (sublingual, buccal), peroral, sublingual, systemic and topical or localized administration. Techniques and formulations generally may be found in Remington: The Science and Practice of Pharmacy ($20^{th}$ ed.) Lippincott, Williams & Wilkins (2000).

Depending on the specific conditions being treated, the compounds may be formulated into liquid (e.g., solutions, suspensions, or emulsions) or solid dosage forms (capsules or tablets) and administered systemically or locally. The compounds may be delivered, for example, in a timed-, controlled, or sustained-slow release form as is known to those skilled in the art. Techniques for formulation and administration may be found in Remington: The Science and Practice of Pharmacy ($20^{th}$ ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intra-sternal, intra-synovial, intra-hepatic, intralesional, intracranial, intraperitoneal, intranasal, or intraocular injections or other modes of delivery. In some embodiments, the pharmaceutical composition is administered orally. In some embodiments, the pharmaceutical composition is administered intravenously. In some embodiments, the pharmaceutical composition is administered intramuscularly. In some embodiments, the pharmaceutical composition is administered intrathecally. In some embodiments, the pharmaceutical composition is administered subcutaneously.

For injection, the compounds of the disclosure may be formulated and diluted in aqueous solutions, such as in physiologically compatible buffers, such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the compounds of the disclosure also may be formulated by methods known to those of skill in the art, and may include, for example, but not limited to, examples of solubilizing, diluting, or dispersing substances, such as saline; preservatives, such as benzyl alcohol; absorption promoters; and fluorocarbons.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein. Generally, the compounds according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A non-limiting dosage is 10 to 30 mg per day. The exact dosage will depend upon the route of administration, the form in which the compound is administered, the subject to be treated, the body weight of the subject to be treated, the bioavailability of the compound(s), the adsorption, distribution, metabolism, and excretion (ADME) toxicity of the compound(s), and the preference and experience of the attending physician. Examples of dosage include about 0.01 to about 100 mg per kg patient body weight per day (mg kg per day), about 0.01 to about 50 mg/kg per day, about 0.01 to about 25 mg kg per day, or about 0.05 to about 10 mg kg per day, which may be administered in single or multiple doses, particularly about 0.1, about 1, about 5, about 10, about 15, about 20, about 25, about 30, about 35, about 40, about 45, about 50, about 55, about 60, about 65, about 70, about 75, about 80, about 85, about 90, about 95, and about 100 mg/kg per day.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the compounds with solid excipients, optionally grinding a resulting mixture, and processing the mixture of granules, after adding suitable auxiliaries, if desired, to obtain tablets or dragee cores. Suitable excipients are, in particular, fillers, such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof, such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler, such as lactose, binders, such as starches, and/or lubricants such, as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

IV. Methods for Treating a Disease or Disorder

The compounds are orally bioavailable, less toxic, and allow a clinically acceptable dosing paradigm for diseases or conditions wherein excess and/or aberrant glutamine activity is implicated. As used herein, the term "glutamine antagonist" refers to a glutamine analog that interferes with a glutamine metabolic pathway, e.g., the inhibition or blocking of a metabolic pathway downstream of glutamine in which glutamine acts as a precursor of one or more non-glutamine compounds. Examples of such metabolic pathways are well known (see, e.g., Hensley et al., 2013; DeBerardinis et al., 2009; and Medina et al., 1992). In some contexts, the term glutamine antagonist also includes glutamine analogs that inhibit glutamine uptake by cells, thereby reducing its biological activity. Diseases or conditions wherein excess and/or aberrant glutamine activity is implicated include, but are not limited to, infection, cancer, autoimmune diseases, and neurodegenerative or neurological diseases and other central nervous system disorders.

In general, the methods result in a decrease in the severity of a disease or condition in a subject. The term "decrease" is meant to inhibit, suppress, attenuate, diminish, arrest, or stabilize a symptom of a disease or condition.

As used herein, the terms "treat," "treating," "treatment," and the like refer to reducing or ameliorating a disease or condition, and/or symptoms associated therewith. It will be appreciated that, although not precluded, treating a disease or condition does not require that the disorder, condition or symptoms associated therewith be completely eliminated.

Accordingly, in some embodiments, the provided is a method for treating a disease or a condition, the method comprising administering to a subject in need of treatment thereof, a compound of formula (I), or a pharmaceutical composition of any thereof, in an amount effective for treating the disease or condition.

Also provided is a method of treating a disease or condition with a compound of formula (I), or a pharmaceutical composition comprising the compound of formula (I), optionally together with at least one antimicrobial agent (e.g., antibiotic, antiviral, and the like), to treat an infection.

As used herein, "infection" refers to the invasion of a host organism's bodily tissues by disease-causing organisms, their multiplication, and the reaction of host tissues to these organisms and the toxins they produce. Infectious disease, such as infection by any bacteria or virus, is contemplated for treatment using a compound of formula (I), or a pharmaceutical composition of any thereof.

In some embodiments, the infection comprises a bacterial infection. Antibacterial effects of DON have been demonstrated in *E. coli* (see Coggin et al., 1965). In some embodiments, the compound of formula (I), or pharmaceutical composition of any thereof, inhibits bacterial growth and/or survival.

In some embodiments, the infection comprises a viral infection. The antiviral effects of glutamine analogs, such as DON, have been demonstrated (see, e.g., Cinatl et al., 1997; Nishio et al., 1990). Examples of viral infections contemplated for treatment using a compound of formula (I), or a pharmaceutical composition of any thereof include, without limitation, herpes simplex virus type 1 (HSV-1), herpes simplex virus type 2 (HSV-2), human cytomegalovirus (HCMV), human parainfluenza virus type 2 (HPIV-2), Maloney leukemia virus (MLV), mumps, paramyxovirus, poliovirus, reovirus type 3, respiratory syncytial virus (RSV), Sendai virus, and vesicular stomatitis virus (VSV).

In some embodiments, the compound of formula (I), or pharmaceutical composition of any thereof, inhibits viral replication. In some embodiments, the compound of formula (I), or pharmaceutical composition of any thereof, inhibits replication of herpes simplex virus type 1 (HSV-1). In some embodiments, the compound of formula (I), or pharmaceutical composition of any thereof, inhibits replication of herpes simplex virus type 2 (HSV-2). In some embodiments, the compound of formula (I), or pharmaceutical composition of any thereof, inhibits replication of human cytomegalovirus (HCMV). In some embodiments, the compound of formula (I), or pharmaceutical composition of any thereof, inhibits replication of human parainfluenza virus type 2 (HPIV-2). In some embodiments, the compound of formula (I), or pharmaceutical composition of any thereof, inhibits replication of Maloney leukemia virus (MLV). In some embodiments, the compound of formula (I), or pharmaceutical composition of any thereof, inhibits replication of human Rubulavirus. In some embodiments, the compound of formula (I), or pharmaceutical composition of any thereof, inhibits replication of paramyxovirus. In some embodiments, the compound of formula (I), or pharmaceutical composition of any thereof, inhibits replication of poliovirus. In some embodiments, the compound of formula (I), or pharmaceutical composition of any thereof, inhibits replication of reovirus type 3. In some embodiments, the compound of formula (I), or pharmaceutical composition of any thereof, inhibits replication of respiratory syncytial virus (RSV). In some embodiments, the compound of formula (I), or pharmaceutical composition of any thereof, inhibits replication of Sendai virus. In some embodiments, the compound of formula (I), or pharmaceutical composition of any thereof, inhibits replication of vesicular stomatitis virus (VSV).

In some embodiments, the viral infection is influenza. As used herein, "influenza" refers to influenza A, B, or C, parainfluenza viruses, and any other influenza-like virus (see, e.g., U.S. Publication No. 2006/0276438, which discloses using DON, and azaserine for treatment of influenza).

In an aspect, the presently disclosed subject matter provides the use of a compound of formula (I), or a pharmaceutical composition thereof, optionally together with an antiviral agent, for the manufacture of a medicament for treating a viral infection and/or inhibiting replication.

As used herein, "antiviral agent" includes a compound that inhibits the replication of viruses in cells, tissues, or organisms. Examples of antiviral agents contemplated for use in combination with a compound of formula (I), or a pharmaceutical composition comprising a compound of formula (I) include, but are not limited to, Acyclovir (2-amino-1,9-dihydro-9-[(2-hydroxyethoxy)methyl]-6H-purin-6-one), Valacyclovir (L-valine, 2-[(2-amino-1,6-dihydro-6-oxo-9H-purin-9-yl)methoxy]ethyl ester, Pencyclovir (9-[4-hydroxy-3-(hydroxymethylbutyl)]guanine), Famcyclovir (2-[2-(amino-9H-purin-9-yl)]ethyl-1,3-propanediol diacetate), Ribavirin (1-beta-D-ribofuanosyl-1-H-1,2,4-triazol-3-carboxamide), Lamivudine ((2R,cis)-4-amino-1-(2-hydroxymethyl-1,3-oxathiolan-5-yl)-(1H)-pyrimidine-2-one), Amantadine (1-amantanamine hydrochloride), and Rimantadine (α-methyltricyclo (3.3.1.1/3.7 decane-1-methylamine hydrochloride).

Also provided is a compound of formula (I), or a pharmaceutical composition comprising the compound of formula (I), optionally together with at least one chemotherapeutic agent, at least one radiotherapeutic agent, and/or at least one immunotherapeutic agent for use to treat cancer. In some embodiments, such treatment includes treatment with any combination of radiotherapy, immunotherapy, photodynamic therapy, proton therapy, and/or surgery.

A "chemotherapeutic agent" is used to connote a compound or composition that is administered in the treatment of cancer. Chemotherapeutic agents contemplated for use in combination with a compound of formula (I), or a pharmaceutical composition comprising a compound of formula (I) include, but are not limited to, alkylating agents, such as thiotepa and cyclophosphamide; alkyl sulfonates, such as busulfan, improsulfan and piposulfan; aziridines, such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard: nitrosureas, such as carmustine, chlorozotocin, fotemustine, lomustine, nimustine, ranimustine; antibiotics, such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites, such as methotrexate and 5-fluorouracil (5-FU); folic acid analogues, such as denopterin, methotrexate, pteropterin, trimetrexate; purine analogs, such as fludarabine, 6-mercaptopurine, thiamiprine, thioguanine; pyrimidine analogs, such as ancitabine, azacitidine, 6-azauridine, carmofur, cytosine arabinoside, dideoxyuridine, doxifluridine, enocitabine, floxuridine, 5-FU; androgens, such as calusterone, dromostanolone propionate, epitiostanol, mepitiostane, testolactone; anti-adrenals, such as aminoglutethimide, mitotane, trilostane; folic acid replenishers, such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); taxoids, e.g., paclitaxel and docetaxel; chlorambucil; gemcitabine; 6-thioguanine; mercaptopurine; platinum analogs, such as cisplatin and carboplatin; vinblastine; platinum; etoposide; ifosfamide; mitomycin C; mitoxantrone; vincristine; vinorelbine; navelbine; novantrone; teniposide; daunomycin; aminopterin; xeloda; ibandronate; CPT11; topoisomerase inhibitor RFS 2000; difluoromethylornithine; retinoic acid; esperamicins; capecitabine; and pharmaceutically acceptable salts, acids or derivatives of any of the above. Chemotherapeutic agents also include anti-hormonal agents that act to regulate or inhibit hormone action on tumors, such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens, such as flutamide, nilutamide, bicalutamide, leuprolide, and goserelin; and pharmaceutically acceptable salts, acids or derivatives of any of the above.

In some embodiments, the chemotherapeutic agent is a topoisomerase inhibitor. Topoisomerase inhibitors are chemotherapy agents that interfere with the action of a topoisomerase enzyme (e.g., topoisomerase I or II). Topoisomerase inhibitors include, but are not limited to, doxorubicin HCl, daunorubicin citrate, mitoxantrone HCl, actinomycin D, etoposide, topotecan HCl, teniposide, and irinotecan, as well as pharmaceutically acceptable salts, acids, or derivatives of any of these.

In some embodiments, the chemotherapeutic agent is an anti-metabolite. An anti-metabolite is a chemical with a structure that is similar to a metabolite required for normal biochemical reactions, yet different enough to interfere with one or more normal functions of cells, such as cell division. Anti-metabolites include, but are not limited to, gemcitabine, fluorouracil, capecitabine, methotrexate sodium, raltitrexed, pemetrexed, tegafur, cytosine arabinoside, thioguanine, 5-azacytidine, 6-mercaptopurine, azathioprine, 6-thioguanine, pentostatin, fludarabine phosphate, and cladribine, as well as pharmaceutically acceptable salts, acids, or derivatives of any of these.

In certain embodiments, the chemotherapeutic agent is an antimitotic agent, including, but not limited to, agents that bind tubulin. In some embodiments, the agent is a taxane. In certain embodiments, the agent is paclitaxel or docetaxel, or a pharmaceutically acceptable salt, acid, or derivative of paclitaxel or docetaxel. In certain alternative embodiments, the antimitotic agent comprises a *vinca* alkaloid, such as vincristine, binblastine, vinorelbine, or vindesine, or pharmaceutically acceptable salts, acids, or derivatives thereof.

As used herein, the term "immunotherapeutic agent" refers to a molecule that can aid in the treatment of a disease by inducing, enhancing, or suppressing an immune response in a cell, tissue, organ or subject. Examples of immunotherapeutic agents contemplated for use in combination with a compound of formula (I), or a pharmaceutical composition comprising a compound of formula (I) include, but are not limited to, immune checkpoint molecules (e.g., antibodies to immune checkpoint proteins), interleukins (e.g., IL-2, IL-7, IL-12, IL-15), cytokines (e.g., interferons. G-CSF, imiquimod), chemokines (e.g., CCL3, CCL26, CXCL7), vaccines (e.g., peptide vaccines, dendritic cell (DC) vaccines, EGFRvIII vaccines, mesothilin vaccine, G-VAX, listeria vaccines), and adoptive T cell therapy including chimeric antigen receptor T cells (CAR T cells).

Examples of immune checkpoint modulators of use herein include, but are not limited to, small organic molecules (e.g., haptens) or small inorganic molecules; saccharides; oligosaccharides; polysaccharides; a biological macromolecule selected from the group consisting of peptides (e.g., aptides), proteins, peptide analogs and derivatives; peptidomimetics; nucleic acids selected from the group consisting of miRNAs, siRNAs, shRNAs, antisense nucleic acids, such as antisense RNAs, ribozymes, and aptamers; an extract made from biological materials selected from the group consisting of bacteria, plants, fungi, animal cells, and animal tissues; naturally occurring or synthetic compositions; and any combination thereof. Other examples of immune checkpoint modulators include orthosteric inhibitors, allosteric regulators, interfacial binders, and molecular analogues of substrates that act as competitive inhibitors.

Examples of immune checkpoint modulators include, without limitation, PD-1 antagonists, PD-L1 antagonists, CTLA-4 antagonists, Lag-3 antagonists, CD 137 antagonists, KIR antagonists, Tim3 antagonists, Ox40 agonists, B7-H3 antagonists, and combinations thereof.

Exemplary CTLA-4 antagonists include, without limitation, ipilimumab, tremelimumab and combinations thereof.

Exemplary Lag-3 antagonists include, without limitation, BMS-986016 and IMP321.

Exemplary CD 137 antagonists include, without limitation, CD137-specific antibody, peptide, organic small molecule, antisense oligonucleotide, siRNA, antisense expression vector or recombinant virus. In some embodiments, the CD137-specific antibody is clone BBK-2 or clone 4B4-1, as described in WIPO International Application Publication No. WO200405513A2.

T-cell immunoglobulin and mucin domain 3 (TIM3) antagonists include, without limitation, anti-TIM3 monoclonal antibodies.

Ox40 agonists are described by Linch et al, "OX40 Agonists and Combination Immunotherapy: Putting the Pedal to the Metal" Front Oncol 5:34; 2015. Exemplary Ox40 agonists include, without limitation, anti-Ox40 agonists antibodies. Other exemplary Ox40 agonists include, without limitation, 0X86 and Fc-OX40L.

Exemplary B7-H3 antagonists include, without limitation, MGA271.

Exemplary PD-L1 antagonists include, without limitation, BMS-936559/MDX-1 105, MEDI4736, MPDL3280A, MPDL3280A, MSB0010718C, and combinations thereof.

PD-1 antagonists of use herein include, without limitation, AMP-224, AMP-554, nivolumab, pembrolizumab, pidilizumab, and combinations thereof.

Particular examples of immune checkpoint inhibitors include ipilimumab (Yervoy®), pembrolizumab (Keytruda®) nivolumab (Opdivo®), atezolizumab (Tecentriq®), avelumab (Bravencio®), and durvalumab (Imfinzi®).

The immune checkpoint inhibitor and the compound of the disclosure are administered simultaneously or sequentially, in either order. In an additional aspect, the therapeutic is administered prior to the immune checkpoint inhibitor.

As used herein, "radiotherapeutic agent" means an agent which may be used in radiotherapy that acts through damaging cells (e.g., malignant cells) as a target through radiation irradiation. An exemplary radiotherapeutic agent contemplated for use in combination with a compound of formula (I), or a pharmaceutical composition comprising a compound of formula (I) is the titanium peroxide contained in the substrate particle which generates a hydroxyl radial through radiation irradiation, and the hydroxyl radial exerts an action of attacking a target, as described in U.S. Pat. No. 8,580,312.

As used herein, a "cancer" in a patient refers to the presence of cells possessing characteristics typical of cancer-causing cells, for example, uncontrolled proliferation, loss of specialized functions, immortality, significant metastatic potential, significant increase in anti-apoptotic activity, rapid growth and proliferation rate, and certain characteristic morphology and cellular markers. In some circumstances, cancer cells will be in the form of a tumor; such cells may exist locally within an animal, or circulate in the blood stream as independent cells, for example, leukemic cells. A "tumor," as used herein, refers to all neoplastic cell growth and proliferation, whether malignant or benign, and all precancerous and cancerous cells and tissues. A "solid tumor," as used herein, is an abnormal mass of tissue that generally does not contain cysts or liquid areas. A solid tumor may be in the brain, colon, breasts, prostate, liver, kidneys, lungs, esophagus, head and neck, ovaries, cervix, stomach, colon, rectum, bladder, uterus, testes, and pancreas, as non-limiting examples. In some embodiments, the solid tumor regresses or its growth is slowed or arrested after the solid tumor is treated with the presently disclosed methods. In other embodiments, the solid tumor is malignant. In some embodiments, the cancer comprises Stage 0 cancer. In some embodiments, the cancer comprises Stage I cancer. In some embodiments, the cancer comprises Stage II cancer. In some embodiments, the cancer comprises Stage III cancer. In some embodiments, the cancer comprises Stage IV cancer. In some embodiments, the cancer is refractory and/or metastatic. For example, the cancer may be refractory to treatment with radiotherapy, chemotherapy or monotreatment with immunotherapy. Cancer as used herein includes newly diagnosed or recurrent cancers, including without limitation, acute lymphoblastic leukemia, acute myelogenous leukemia, advanced soft tissue sarcoma, brain cancer, metastatic or aggressive breast cancer, breast carcinoma, bronchogenic carcinoma, choriocarcinoma, chronic myelocytic leukemia, colon carcinoma, colorectal carcinoma, Ewing's sarcoma, gastrointestinal tract carcinoma, glioma, glioblastoma multiforme, head and neck squamous cell carcinoma, hepatocellular carcinoma, Hodgkin's disease, intracranial ependymoblastoma, large bowel cancer, leukemia, liver cancer, lung carcinoma, Lewis lung carcinoma, lymphoma, malignant fibrous histiocytoma, a mammary tumor, melanoma, mesothelioma, neuroblastoma, osteosarcoma, ovarian cancer, pancreatic cancer, a pontine tumor, premenopausal breast cancer, prostate cancer, rhabdomyosarcoma, reticulum cell sarcoma, sarcoma, small cell lung cancer, a solid tumor, stomach cancer, testicular cancer, and uterine carcinoma.

In some embodiments, the cancer is acute leukemia. In some embodiments, the cancer is acute lymphoblastic leukemia. In some embodiments, the cancer is acute myelogenous leukemia. In some embodiments, the cancer is advanced soft tissue sarcoma. In some embodiments, the cancer is a brain cancer. In some embodiments, the cancer is breast cancer (e.g., metastatic or aggressive breast cancer). In some embodiments, the cancer is breast carcinoma. In some embodiments, the cancer is bronchogenic carcinoma. In some embodiments, the cancer is choriocarcinoma. In some embodiments, the cancer is chronic myelocytic leukemia. In some embodiments, the cancer is a colon carcinoma (e.g., adenocarcinoma). In some embodiments, the cancer is colorectal cancer (e.g., colorectal carcinoma). In some embodiments, the cancer is Ewing's sarcoma. In some embodiments, the cancer is gastrointestinal tract carcinoma. In some embodiments, the cancer is a glioma. In some embodiments, the cancer is glioblastoma multiforme. In some embodiments, the cancer is head and neck squamous cell carcinoma. In some embodiments, the cancer is hepatocellular carcinoma. In some embodiments, the cancer is Hodgkin's disease. In some embodiments, the cancer is intracranial ependymoblastoma. In some embodiments, the cancer is large bowel cancer. In some embodiments, the cancer is leukemia. In some embodiments, the cancer is liver cancer. In some embodiments, the cancer is lung cancer (e.g., lung carcinoma). In some embodiments, the cancer is Lewis lung carcinoma. In some embodiments, the cancer is lymphoma. In some embodiments, the cancer is malignant fibrous histiocytoma. In some embodiments, the cancer comprises a mammary tumor. In some embodiments, the cancer is melanoma. In some embodiments, the cancer is mesothelioma. In some embodiments, the cancer is neuroblastoma. In some embodiments, the cancer is osteosarcoma. In some embodiments, the cancer is ovarian cancer. In some embodiments, the cancer is pancreatic cancer. In some embodiments, the cancer comprises a pontine tumor. In some embodiments, the cancer is premenopausal breast cancer. In some embodiments, the cancer is prostate cancer. In some embodiments, the cancer is rhabdomyosarcoma. In some embodiments, the cancer is reticulum cell sarcoma. In some embodiments, the cancer is sarcoma. In some embodiments, the cancer is small cell lung cancer. In some embodiments, the cancer comprises a solid tumor. In some embodiments, the cancer is stomach cancer. In some embodiments, the cancer is testicular cancer. In some embodiments, the cancer is uterine carcinoma.

In some embodiments, the cancer comprises a glutamine-dependent cancer in which glutamine is an important fuel source for cellular energy in the cancer (e.g., hematopoietic tumors, hepatomas, Ehrilich carcinoma (see Huber et al., "Uptake of glutamine antimetabolites 6-diazo-5-oxo-L-norleucine (DON) in sensitive and resistant tumor cell lines," Int. J. Cancer. 1988; 41:752-755)).

In some embodiments, the cancer is a Myc-dependent cancer. As used herein, "Myc-dependent cancer" refers to a cancer exhibiting activation, overexpression and/or amplification of c-Myc. In some contexts, a "Myc-dependent cancer" is a cancer in which c-Myc plays a role in increased glutamine metabolism in the cancer cells. Examples of Myc-dependent cancers include, without limitation, lymphoma, neuroblastoma, and small cell lung cancer.

In some embodiments, the cancer is an mTORC1-dependent cancer. As used herein, "mTORC1-dependent cancer" refers to a cancer in which mTORC1 is activated in a glutamine-dependent manner, i.e., that is mTORC1 plays a role in increased glutamine metabolism in the cancer cells.

Disclosed is a method of using a compound of formula (I), or a pharmaceutical composition comprising the compound of formula (I), optionally together with at least one immunosuppressant and/or anti-inflammatory agent, to treat an autoimmune disease, immune disorder, or inflammatory disorder.

As used herein, "immunosuppressant agent" means an agent which may be used in immunotherapy to reduce or prevent an immune response in a cell, organ, tissue, or subject. Examples of immunosuppressant agents contemplated for use in combination with a compound of formula (I), or a pharmaceutical composition comprising a compound of formula (I) include corticosteroids, calcineurin inhibitors, antiproliferative agents, SIP receptor agonists, kinase inhibitors, monoclonal antilymphocyte antibodies and polyclonal antilymphocyte antibodies. Non-limiting examples of corticosteroids include Prednisone (Deltasone® and Orasone®) and Methylprednisolone (SoluMedrol®). Non-limiting examples of calcineurin inhibitors include Cyclosporine (Cyclosporin A, SangCya, Sandimmune®, Neoral®, Gengraf®), ISA, Tx247, ABT-281, ASM 981 and Tacrolimus (Prograf®, FK506). Non-limiting examples of antiproliferative agents include Mycophenolate Mofetil (CellCept®), Azathioprene (Imuran®), and Sirolimus (Rapamune®). Non-limiting examples of SIP receptor agonists include FTY 720 or analogues thereof. Non-limiting examples of kinase inhibitors include mTOR kinase inhibitors, which are compounds, proteins or antibodies that target, decrease or inhibit the activity and/or function of members of the serine/threonine mTOR family. These include, without limitation, CCI-779, ABT578, SAR543, rapamycin and derivatives or analogs thereof, including 40-O-(2-hydroxyethyl)-rapamycin, rapalogs, including AP23573, AP23464, AP23675 and AP23841 from Ariad, Everolimus (CERTICAN, RAD001), biolimus 7, biolimus 9 and sirolimus (RAPAMUNE). Kinase inhibitors also include protein kinase C inhibitors, which include the compounds described the PCT publications WO 2005/097108 and WO 2005/068455. Non-limiting examples of monoclonal anti-lymphocyte antibodies include Muromonab-CD3 (Orthoclone OKT3®), Interleukin-2 Receptor Antagonist (Basiliximab, Simulect®), and Daclizumab (Zenapax®). Non-limiting examples of polyclonal antilymphocyte antibodies include Antithymocyte globulin-equine (Atgam®) and Antithymocyte globulin-rabbit (RATG, Thymoglobulin®). Other immunosuppressants include, without limitation, SERP-1, a serine protease inhibitor produced by malignant rabbit fibroma virus (MRV) and myxoma virus (MYX), described in US Patent Publication No. 2004/0029801.

As used herein, "anti-inflammatory agent" refers to an agent that may be used to prevent or reduce an inflammatory response or inflammation in a cell, tissue, organ, or subject. Exemplary anti-inflammatory agents contemplated for use in combination with a compound of formula (I), or a pharmaceutical composition comprising a compound of formula (I) include, without limitation, steroidal anti-inflammatory agents, a nonsteroidal anti-inflammatory agent, or a combination thereof. In some embodiments, anti-inflammatory agents include clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone, dexamethasone acetate, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof. The anti-inflammatory agent may also be a biological inhibitor of proinflammatory signaling molecules including antibodies to such biological inflammatory signaling molecules.

Autoimmunity is the failure of an organism to recognize its own constituent parts (down to the sub-molecular levels) as "self," which results in an immune response against its own cells and tissues. Any disease that results from such an aberrant immune response is termed an autoimmune disease. An unwanted immune response may be, for example, immune responses associated with an autoimmune disorder, allergies, or inflammatory disorders. The term "immune disorders" are diseases involving the immune system that can include but not be limited to allergies, autoimmune diseases, immune complex diseases, immunodeficiency diseases and cancers of the immune system. In some embodiments, the autoimmune disease, immune disorder, or inflammatory disorder is multiple sclerosis.

The presently disclosed subject matter contemplates using a compound of formula (I), or a pharmaceutical composition comprising the compound of formula (I), optionally together with at least one neuroprotective agent and/or at least one neurotrophic factor, and/or at least one neuroregenerative agent, to treat a neurodegenerative or neurological disorder or disease.

A "neurodegenerative disorder" is a disease, disorder, or condition that is characterized by the progressive loss of the structure or function of neurons (e.g., degeneration or dysfunction of neurons or other neural cells). Glutaminase-catalyzed hydrolysis of glutamine to glutamate is a predominant source of brain glutamate. Normal central nervous system (CNS) synaptic transmission uses glutamate as the major excitatory amino acid neurotransmitter. Excessive glutamatergic signaling, known as excitotoxicity, is believed to cause CNS damage in various neurodegenerative diseases, such as stroke, amyotrophic lateral sclerosis (ALS), Huntington's disease, Alzheimer's disease, and HIV-associated dementia. Accordingly, without wishing to be bound by theory, it is believed that the presently disclosed compounds can be used to treat such neurodegenerative diseases, for example, by inhibiting glutaminase to ameliorate the CNS damage resulting from excitotoxicity due to excessive glutamatergic signaling.

In particular embodiments, the neurodegenerative disorder is multiple sclerosis (MS). DON has been shown to be effective in ameliorating experimental autoimmune enchaphalomyelitis (EAE), an animal model of multiple sclerosis (MS)(see, e.g., Shijie, et al., 2009). In particular embodiments, the neurodegenerative disorder is HIV-associated dementia (HAD). In particular embodiments, the neurodegenerative disorder is ischemia (e.g., transient ischemic brain injury). In particular embodiments, the neurodegenerative disorder is stroke. In particular embodiments, the neurodegenerative disorder is amyotrophic lateral sclerosis (ALS). In particular embodiments, the neurodegenerative disorder is Huntington's disease. In particular embodiments, the neurodegenerative disorder is Alzheimer's disease.

In some embodiments, the presently disclosed subject matter provides methods for inhibiting the excess and/or aberrant glutamine activity found in a subject with a disease or condition. As used herein, the term "inhibit" means to decrease or diminish the excess and/or aberrant glutamine activity found in a subject. The term "inhibit" also may mean to decrease, suppress, attenuate, diminish, arrest, or stabilize the development or progression of a disease or condition. Inhibition may occur, for e.g., by at least 10%, 20%, 30%, 40%, 50%, 60%, 70%, 80%, 90%, 95%, 98%, 99%, or even 100% compared to an untreated control subject or a subject without the disease or disorder. As used herein, the term "excess glutamine activity" means an increase in glutamine activity in a subject with a disease or condition as compared to the glutamine activity in a subject without a similar disease or condition, such as an increase of approximately 100%, 100%, 200%, 300%, 400%, 500%, 600%, 700%, 800%, 900%, 1000%, or more. As used herein, the term "aberrant glutamine activity" means a change in the biological activity of glutamine in a subject with a disease or condition as compared to the glutamine activity in a subject without a similar disease or condition, such utilization of glutamine in the growth and/or proliferation of malignant, neoplastic, or other pathologic cellular processes.

In some embodiments, the disease or condition involves excess and/or aberrant glutamine activity. In such aspects, the method further comprises inhibiting the excess and/or aberrant glutamine activity when the compound of formula (I), or the pharmaceutical composition of any thereof, is administered.

In another aspect, the presently discloses subject matter involves the use of a compound of formula (I), or a pharmaceutical composition of any thereof, for treating a disease or condition. In some embodiments, the compound of formula (I), or the pharmaceutical composition of any thereof is used to treat a disease or condition selected from the group consisting of an infection, cancer, an autoimmune disease, an inflammatory disease, and a neurodegenerative or neurological disease. In some embodiments, the compound of formula (I), or the pharmaceutical composition of any thereof is used to treat a disease or condition selected from the group consisting of multiple sclerosis, convulsions, epilepsy, and viral encephalitis. In some embodiments, the compound of formula (I), or the pharmaceutical composition of any thereof is used to treat a disease or condition that involves excess and/or aberrant glutamine activity. In such aspects, the use involves inhibiting the excess and/or aberrant glutamine activity when the compound of formula (I), or the pharmaceutical composition of any thereof, is used to treat the disease or condition.

In another aspect, provided is a method of enhancing the effects of an immune checkpoint inhibitor, enabling a subject to respond to an immune checkpoint inhibitor, or enabling the toxicity or the dose or number of treatments with an immune checkpoint inhibitor to be reduced, comprising administering to a subject in need of treatment thereof a therapeutically effective amount of a compound of the disclosure, or the pharmaceutical composition thereof, and an immune checkpoint inhibitor. In one embodiment, the coadministration of the compound of the disclosure, or the pharmaceutical composition thereof, reverses resistance or refractoriness to the immune checkpoint inhibitor. In another embodiment, the disease or disorder is a cancer.

In another embodiment, the disease or disorder is immune checkpoint-resistant colon cancer, glioblastoma, or head and neck cancer. In another embodiment, the immune checkpoint inhibitor is ipilimumab (Yervoy®), pembrolizumab (Keytruda®), nivolumab (Opdivo®), atezolizumab (Tecentriq®), avelumab (Bravencio®), or durvalumab (Imfinzi®).

In another aspect, provided is a method for treating an oncological, immunological, infectious or neurological disease or disorder that is refractory to immune checkpoint inhibitor therapy, the method comprising administering to a subject in need thereof, and having the refractory disease or disorder, a therapeutically effective amount of a compound of the disclosure or the pharmaceutical composition thereof. The compound of the disclosure may be administered alone or together with an immune checkpoint inhibitor therapy. The administration may be before, simultaneous with or after the immune checkpoint inhibitor. In another embodiment, the immune checkpoint inhibitor is ipilimumab (Yervoy®), pembrolizumab (Keytruda®), nivolumab (Opdivo®), atezolizumab (Tecentriq®), avelumab (Bravencio®), or durvalumab (Imfinzi®).

In another aspect is provided a method for treating an oncological, immunological, infectious or neurological disease or disorder that is refractory to checkpoint inhibitor therapy, the method comprising administering to a subject in need thereof, and having the refractory disease or disorder, a therapeutically effective amount of a compound of the disclosure or the pharmaceutical composition thereof. In one embodiment, the compound or pharmaceutical composition thereof is administered together with an immune checkpoint inhibitor therapy. In another embodiment, the compound or pharmaceutical composition is administered to the subject before, simultaneous with or after the checkpoint inhibitor. In another embodiment, the immune checkpoint inhibitor is ipilimumab (Yervoy®), pembrolizumab (Keytruda®), nivolumab (Opdivo®), atezolizumab (Tecentriq®), avelumab (Bravencio®), or durvalumab (Imfinzi®).

V. Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to compounds of formula (I) are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group on a molecule, provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted at one or more positions).

Where substituent groups or linking groups are specified by their conventional chemical formulae, written from left to right, they equally encompass the chemically identical substituents that would result from writing the structure from right to left, e.g., —$CH_2O$— is equivalent to —$OCH_2$—; —C(=O)O— is equivalent to —OC(=O)—; —OC(=O) NR— is equivalent to —NRC(=O)O—, and the like.

When the term "independently selected" is used, the substituents being referred to (e.g., R groups, such as groups $R_1$, $R_2$, and the like, or variables, such as "m" and "n"), can be identical or different. For example, both $R_1$ and $R_2$ can be substituted alkyls, or $R_1$ can be hydrogen and $R_2$ can be a substituted alkyl, and the like.

The terms "a," "an," or "a (n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

For the purpose of the present disclosure, the term "alkyl" as used by itself or as part of another group refers to a straight- or branched-chain aliphatic hydrocarbon containing one to twelve carbon atoms (i.e., $C_{1-12}$ alkyl) or the number of carbon atoms designated (i.e., a $C_1$ alkyl such as methyl, a $C_2$ alkyl such as ethyl, a $C_3$ alkyl such as propyl or isopropyl, etc.). In one embodiment, the alkyl group is chosen from a straight chain $C_{1-10}$ alkyl group. In another embodiment, the alkyl group is chosen from a branched chain $C_{3-10}$ alkyl group. In another embodiment, the alkyl group is chosen from a straight chain $C_{1-6}$ alkyl group. In another embodiment, the alkyl group is chosen from a branched chain $C_{3-6}$ alkyl group. In another embodiment, the alkyl group is chosen from a straight chain $C_{1-4}$ alkyl group. In another embodiment, the alkyl group is chosen from a branched chain $C_{3-4}$ alkyl group. In another embodiment, the alkyl group is chosen from a straight or branched chain $C_{3-4}$ alkyl group. Non-limiting exemplary $C_{1-10}$ alkyl groups include methyl, ethyl, propyl, isopropyl, butyl, sec-butyl, tert-butyl, iso-butyl, 3-pentyl, hexyl, heptyl, octyl, nonyl, decyl, and the like. Non-limiting exemplary $C_{1-4}$ alkyl groups include methyl, ethyl, propyl, isopropyl, butyl, sec-butyl, tert-butyl, and iso-butyl.

For the purpose of the present disclosure, the term "substituted alkyl" as used by itself or as part of another group means that the alkyl as defined above substituted with one, two, or three substituents independently chosen from nitro, haloalkoxy, aryloxy, aralkyloxy, alkylthio, sulfonamido, alkylcarbonyl, arylcarbonyl, alkylsulfonyl, arylsulfonyl, carboxy, carboxyalkyl, cycloalkyl, and the like. In one embodiment, the optionally substituted alkyl is substituted with two substituents. In another embodiment, the optionally substituted alkyl is substituted with one substituent. Non-limiting exemplary optionally substituted alkyl groups include —$CH_2CH_2NO_2$, —$CH_2SO_2CH_3$, —$CH_2CH_2CO_2H$, —$CH_2CH_2SO_2CH_3$, —$CH_2CH_2COPh$, and —$CH_2C_6H_{11}$.

For the purpose of the present disclosure, the term "cycloalkyl" as used by itself or as part of another group refers to saturated and partially unsaturated (containing one or two double bonds) cyclic aliphatic hydrocarbons containing one to three rings having from three to fourteen carbon atoms (i.e., $C_{3-14}$ cycloalkyl) or the number of carbons designated. In one embodiment, the cycloalkyl group has two rings. In one embodiment, the cycloalkyl group has one ring. In another embodiment, the cycloalkyl group is chosen from a $C_{3-8}$ cycloalkyl group. In another embodiment, the cycloalkyl group is chosen from a $C_{3-6}$ cycloalkyl group. Non-limiting exemplary cycloalkyl groups include cyclopropyl, cyclobutyl, cyclopentyl, cyclohexyl, cycloheptyl, cyclooctyl, norbornyl, decalin, adamantyl, cyclohexenyl, and cyclopentenyl, cyclohexenyl. One example of a cycloakyl group includes:

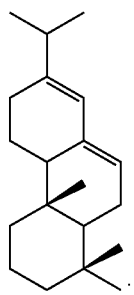

For the purpose of the present disclosure, the term "substituted cycloalkyl" as used by itself or as part of another group means that the cycloalkyl as defined above substituted with one, two, or three substituents independently chosen from halo, nitro, cyano, hydroxy, amino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, mercaptoalkyl, and (heterocyclo)alkyl. In one embodiment, the optionally substituted cycloalkyl is substituted with two substituents. In another embodiment, the optionally substituted cycloalkyl is substituted with one substituent.

For the purpose of the present disclosure, the term "alkenyl" as used by itself or as part of another group refers to an alkyl group as defined above containing one, two or three carbon-to-carbon double bonds. In one embodiment, the alkenyl group is chosen from a $C_{2-6}$ alkenyl group. In another embodiment, the alkenyl group is chosen from a $C_{2-4}$ alkenyl group. Non-limiting exemplary alkenyl groups include ethenyl, propenyl, isopropenyl, butenyl, sec-butenyl, pentenyl, and hexenyl.

For the purpose of the present disclosure, the term "substituted alkenyl" as used herein by itself or as part of another group means the alkenyl as defined above substituted with one, two or three substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, alkyl, cycloalkyl, alkenyl, alkynyl, aryl, heteroaryl, or heterocyclo.

For the purpose of the present disclosure, the term "alkynyl" as used by itself or as part of another group refers to an alkyl group as defined above containing one to three carbon-to-carbon triple bonds. In one embodiment, the alkynyl has one carbon-to-carbon triple bond. In one embodiment, the alkynyl group is chosen from a $C_{2-6}$ alkynyl group. In another embodiment, the alkynyl group is chosen from a $C_{2-4}$ alkynyl group. Non-limiting exemplary alkynyl groups include ethynyl, propynyl, butynyl, 2-butynyl, pentynyl, and hexynyl groups.

For the purpose of the present disclosure, the term "substituted alkynyl" as used herein by itself or as part of another group means the alkynyl as defined above is substituted with one, two or three substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, alkyl, cycloalkyl, alkenyl, alkynyl, aryl, heteroaryl, or heterocyclo.

For the purpose of the present disclosure, the term "haloalkyl" as used by itself or as part of another group refers to an alkyl group substituted by one or more fluorine, chlorine, bromine and/or iodine atoms. In one embodiment, the alkyl group is substituted by one, two, or three fluorine and/or chlorine atoms. In another embodiment, the haloalkyl group is chosen from a $C_{1-4}$ haloalkyl group. Non-limiting exemplary haloalkyl groups include fluoromethyl, 2-fluoroethyl, difluoromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, and trichloromethyl groups.

For the purpose of the present disclosure, the term "hydroxyalkyl" as used by itself or as part of another group refers to an alkyl group substituted with one or more, e.g., one, two, or three, hydroxy groups. In one embodiment, the hydroxyalkyl group is a monohydroxyalkyl group, i.e., substituted with one hydroxy group. In another embodiment, the hydroxyalkyl group is a dihydroxyalkyl group, i.e., substituted with two hydroxy groups, e.g.,

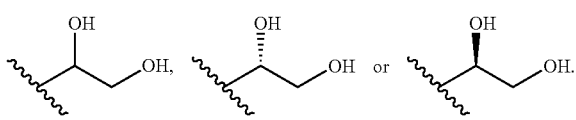 [SMILES: *C(O)CO ; *[C@H](O)CO ; *[C@@H](O)CO]

In another embodiment, the hydroxyalkyl group is chosen from a $C_{1-4}$ hydroxyalkyl group. Non-limiting exemplary hydroxyalkyl groups include hydroxymethyl, hydroxyethyl, hydroxypropyl and hydroxybutyl groups, such as 1-hydroxyethyl, 2-hydroxyethyl, 1,2-dihydroxyethyl, 2-hydroxypropyl, 3-hydroxypropyl, 3-hydroxybutyl, 4-hydroxybutyl, 2-hydroxy-1-methylpropyl, and 1,3-dihydroxyprop-2-yl.

For the purpose of the present disclosure, the term "alkoxy" as used by itself or as part of another group refers to an optionally substituted alkyl, optionally substituted cycloalkyl, optionally substituted alkenyl or optionally substituted alkynyl attached to a terminal oxygen atom. In one embodiment, the alkoxy group is chosen from a $C_{1-4}$ alkoxy group. In another embodiment, the alkoxy group is chosen from a $C_{1-4}$ alkyl attached to a terminal oxygen atom, e.g., methoxy, ethoxy, and tert-butoxy.

For the purpose of the present disclosure, the term "alkylthio" as used by itself or as part of another group refers to a sulfur atom substituted by an optionally substituted alkyl group. In one embodiment, the alkylthio group is chosen from a $C_{1-4}$ alkylthio group. Non-limiting exemplary alkylthio groups include —$SCH_3$, and —$SCH_2CH_3$.

For the purpose of the present disclosure, the term "alkoxyalkyl" as used by itself or as part of another group refers to an alkyl group substituted with an alkoxy group. Non-limiting exemplary alkoxyalkyl groups include methoxymethyl, methoxyethyl, methoxypropyl, methoxybutyl, ethoxymethyl, ethoxyethyl, ethoxypropyl, ethoxybutyl, propoxymethyl, iso-propoxymethyl, propoxyethyl, propoxypropyl, butoxymethyl, tert-butoxymethyl, isobutoxymethyl, sec-butoxymethyl, and pentyloxymethyl.

For the purpose of the present disclosure, the term "haloalkoxy" as used by itself or as part of another group refers to a haloalkyl attached to a terminal oxygen atom. Non-limiting exemplary haloalkoxy groups include fluoromethoxy, difluoromethoxy, trifluoromethoxy, and 2,2,2-trifluoroethoxy.

For the purpose of the present disclosure, the term "aryl" as used by itself or as part of another group refers to a monocyclic or bicyclic aromatic ring system having from six to fourteen carbon atoms (i.e., $C_6$-$C_{14}$ aryl). Non-limiting exemplary aryl groups include phenyl (abbreviated as "Ph"), naphthyl, phenanthryl, anthracyl, indenyl, azulenyl, biphenyl, biphenylenyl, and fluorenyl groups. In one embodiment, the aryl group is chosen from phenyl or naphthyl.

For the purpose of the present disclosure, the term "optionally substituted aryl" as used herein by itself or as part of another group means that the aryl as defined above is either unsubstituted or substituted with one to five substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, mercaptoalkyl, or (heterocyclo)alkyl.

In one embodiment, the optionally substituted aryl is an optionally substituted phenyl. In one embodiment, the optionally substituted phenyl has four substituents. In another embodiment, the optionally substituted phenyl has three substituents. In another embodiment, the optionally substituted phenyl has two substituents. In another embodiment, the optionally substituted phenyl has one substituent. Non-limiting exemplary substituted aryl groups include 2-methylphenyl, 2-methoxyphenyl, 2-fluorophenyl, 2-chlorophenyl, 2-bromophenyl, 3-methylphenyl, 3-methoxyphenyl, 3-fluorophenyl, 3-chlorophenyl, 4-methylphenyl, 4-ethylphenyl, 4-methoxyphenyl, 4-fluorophenyl, 4-chlorophenyl, 2,6-di-fluorophenyl, 2,6-di-chlorophenyl, 2-methyl, 3-methoxyphenyl, 2-ethyl, 3-methoxyphenyl, 3,4-di-methoxyphenyl, 3,5-di-fluorophenyl 3,5-di-methylphenyl, 3,5-dimethoxy, 4-methylphenyl, 2-fluoro-3-chlorophenyl, and 3-chloro-4-fluorophenyl. The term optionally substituted aryl is meant to include groups having fused optionally substituted cycloalkyl and fused optionally substituted heterocyclo rings. Non-limiting examples include:

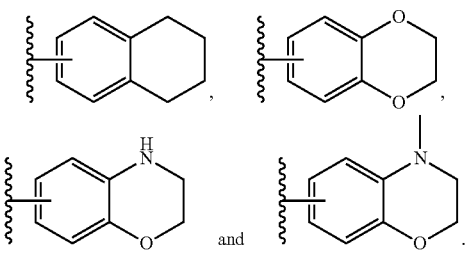

For the purpose of the present disclosure, the term "aryloxy" as used by itself or as part of another group refers to an optionally substituted aryl attached to a terminal oxygen atom. A non-limiting exemplary aryloxy group is PhO—.

For the purpose of the present disclosure, the term "aralkyloxy" as used by itself or as part of another group refers to an aralkyl group attached to a terminal oxygen atom. A non-limiting exemplary aralkyloxy group is $PhCH_2O$—.

For the purpose of the present disclosure, the term "heteroalkyl" as used by itself or part of another group refers to a stable straight or branched chain hydrocarbon radical containing 1 to 10 carbon atoms and at least two heteroatoms, which can be the same or different, selected from the group consisting of O, N, or S, wherein: 1) the nitrogen atom(s) and sulfur atom(s) can optionally be oxidized; and/or 2) the nitrogen atom(s) can optionally be quaternized. The heteroatoms can be placed at any interior position of the heteroalkyl group or at a position at which the heteroalkyl group is attached to the remainder of the molecule. In one embodiment, the heteroalkyl group contains two oxygen atoms. In one embodiment, the heteroalkyl contains one oxygen and one nitrogen atom. In one embodiment, the heteroalkyl contains two nitrogen atoms. Non-limiting exemplary heteroalkyl groups include —$CH_2OCH_2$$CH_2OCH_3$, —$OCH_2CH_2OCH_2CH_2OCH_3$, —$CH_2NHCH_2CH_2OCH_2$, —$OCH_2CH_2NH_2$, —$NHCH_2CH_2N(H)CH_3$, —$NHCH_2CH_2OCH_3$ and —$OCH_2CH_2OCH_3$.

For the purpose of the present disclosure, the term "heteroaryl" or "heteroaromatic" refers to monocyclic and bicyclic aromatic ring systems having 5 to 14 ring atoms (i.e., $C_5$-$C_{14}$ heteroaryl), wherein at least one carbon atom of one of the rings is replaced with a heteroatom independently selected from the group consisting of oxygen, nitrogen and sulfur. In one embodiment, the heteroaryl contains 1, 2, 3, or 4 heteroatoms independently selected from the group consisting of oxygen, nitrogen and sulfur. In one embodiment, the heteroaryl has three heteroatoms. In another embodiment, the heteroaryl has two heteroatoms. In another embodiment, the heteroaryl has one heteroatom. Non-limiting exemplary heteroaryl groups include thienyl, benzo[b]thienyl, naphtho[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, β-carbolinyl, phenanthridinyl, acridinyl, pyrimidinyl, phenanthrolinyl, phenazinyl, thiazolyl, isothiazolyl, phenothiazolyl, isoxazolyl, furazanyl, and phenoxazinyl. In one embodiment, the heteroaryl is chosen from thienyl (e.g., thien-2-yl and thien-3-yl), furyl (e.g., 2-furyl and 3-furyl), pyrrolyl (e.g., 1H-pyrrol-2-yl and 1H-pyrrol-3-yl), imidazolyl (e.g., 2H-imidazol-2-yl and 2H-imidazol-4-yl), pyrazolyl (e.g., 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrimidinyl (e.g., pyrimidin-2-yl, pyrimidin-4-yl, and pyrimidin-5-yl), thiazolyl (e.g., thiazol-2-yl, thiazol-4-yl, and thiazol-5-yl), isothiazolyl (e.g., isothiazol-3-yl, isothiazol-4-yl, and isothiazol-5-yl), oxazolyl (e.g., oxazol-2-yl, oxazol-4-yl, and oxazol-5-yl), isoxazolyl (e.g., isoxazol-3-yl, isoxazol-4-yl, and isoxazol-5-yl), and indazolyl (e.g., 1H-indazol-3-yl). The term "heteroaryl" is also meant to include possible N-oxides. A non-limiting exemplary N-oxide is pyridyl N-oxide.

In one embodiment, the heteroaryl is a 5- or 6-membered heteroaryl. In one embodiment, the heteroaryl is a 5-membered heteroaryl, i.e., the heteroaryl is a monocyclic aromatic ring system having 5 ring atoms wherein at least one carbon atom of the ring is replaced with a heteroatom independently selected from the group consisting of nitrogen, oxygen, and sulfur. Non-limiting exemplary 5-membered heteroaryl groups include thienyl, furyl, pyrrolyl, oxazolyl, pyrazolyl, imidazolyl, thiazolyl, isothiazolyl, and isoxazolyl.

In another embodiment, the heteroaryl is a 6-membered heteroaryl, e.g., the heteroaryl is a monocyclic aromatic ring system having 6 ring atoms wherein at least one carbon atom of the ring is replaced with a nitrogen atom. Non-limiting exemplary 6-membered heteroaryl groups include pyridyl, pyrazinyl, pyrimidinyl, and pyridazinyl.

For the purpose of the present disclosure, the term "optionally substituted heteroaryl" as used by itself or as part of another group means that the heteroaryl as defined above is either unsubstituted or substituted with one to four substituents, e.g., one or two substituents, independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, mercaptoalkyl, or (heterocyclo)alkyl. In one embodiment, the optionally substituted heteroaryl has one substituent. Any available carbon or nitrogen atom can be substituted.

The term optionally substituted heteroaryl is also meant to include groups having fused optionally substituted cycloalkyl and fused optionally substituted heterocyclo rings. Non-limiting examples include:

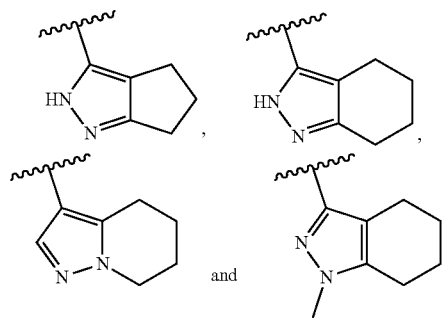

For the purpose of the present disclosure, the term "heterocycle" or "heterocyclo" as used by itself or as part of another group refers to saturated and partially unsaturated (e.g., containing one or two double bonds) cyclic groups containing one, two, or three rings having from three to fourteen ring members (i.e., a 3- to 14-membered heterocyclo) wherein at least one carbon atom of one of the rings is replaced with a heteroatom. Each heteroatom is independently selected from the group consisting of oxygen, sulfur, including sulfoxide and sulfone, and/or nitrogen atoms, which can be oxidized or quaternized. The term "heterocyclo" is meant to include groups wherein a ring —CH$_2$— is replaced with a —C(=O)—, for example, cyclic ureido groups such as 2-imidazolidinone and cyclic amide groups such as β-lactam, γ-lactam, δ-lactam, ε-lactam, and piperazin-2-one. The term "heterocyclo" is also meant to include groups having fused optionally substituted aryl groups, e.g., indolinyl, chroman-4-yl. In one embodiment, the heterocyclo group is chosen from a 5- or 6-membered cyclic group containing one ring and one or two oxygen and/or nitrogen atoms. The heterocyclo can be optionally linked to the rest of the molecule through any available carbon or nitrogen atom. Non-limiting exemplary heterocyclo groups include dioxanyl, tetrahydropyranyl, 2-oxopyrrolidin-3-yl, piperazin-2-one, piperazine-2,6-dione, 2-imidazolidinone, piperidinyl, morpholinyl, piperazinyl, pyrrolidinyl, and indolinyl.

For the purpose of the present disclosure, the term "optionally substituted heterocyclo" as used herein by itself or part of another group means the heterocyclo as defined above is either unsubstituted or substituted with one to four substituents independently selected from the group consisting of halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, alkoxycarbonyl, CF$_3$C(=O)—, arylcarbonyl, alkylsulfonyl, arylsulfonyl, carboxy, carboxyalkyl, alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, mercaptoalkyl, and (heterocyclo)alkyl. Substitution may occur on any available carbon or nitrogen atom, or both. Non-limiting exemplary optionally substituted heterocyclo groups include:

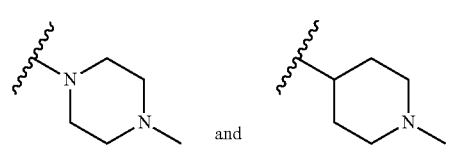

For the purpose of the present disclosure, the term "amino" as used by itself or as part of another group refers to —NR$^{12}$R$^{13}$, wherein R$^{12}$ and R$^{13}$ are each independently hydrogen, alkyl, hydroxyalkyl, optionally substituted cycloalkyl, optionally substituted aryl, optionally substituted heterocyclo, or optionally substituted heteroaryl, or R$^{11}$ and R$^{12}$ are taken together to form a 3- to 8-membered optionally substituted heterocyclo. Non-limiting exemplary amino groups include —NH$_2$ and —N(H)(CH$_3$).

For the purpose of the present disclosure, the term "(amino)alkyl" as used by itself or as part of another group refers to an alkyl group substituted with an amino group. Non-limiting exemplary amino alkyl groups include —CH$_2$CH$_2$NH$_2$, and —CH$_2$CH$_2$N(H)CH$_3$, —CH$_2$CH$_2$N(CH$_3$)$_2$, and —CH$_2$N(H)cyclopropyl.

For the purpose of the present disclosure, the term "carboxamido" as used by itself or as part of another group refers to a radical of formula —C(=O)NR$^{14}$R$^{15}$, wherein R$^{14}$ and R$^{15}$ are each independently hydrogen, optionally substituted alkyl, hydroxyalkyl, optionally substituted cycloalkyl, optionally substituted aryl, optionally substituted heterocyclo, or optionally substituted heteroaryl, or R$^{14}$ and R$^{15}$ taken together with the nitrogen to which they are attached form a 3- to 8-membered optionally substituted heterocyclo group. In one embodiment, R$^{14}$ and R$^{15}$ are each independently hydrogen or optionally substituted alkyl. In one embodiment, R$^{14}$ and R$^{15}$ are taken together to taken together with the nitrogen to which they are attached form a 3- to 8-membered optionally substituted heterocyclo group. Non-limiting exemplary carboxamido groups include, but are not limited to, —CONH$_2$, —CON(H)CH$_3$, —CON(CH$_3$)$_2$, —CON(H)Ph,

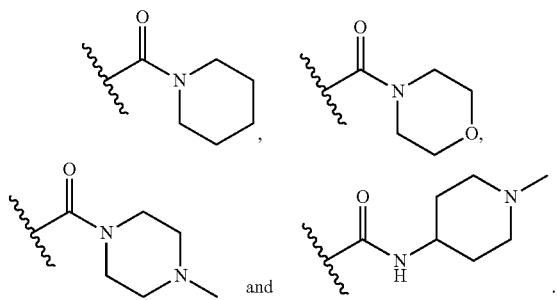

For the purpose of the present disclosure, the term "sulfonamido" as used by itself or as part of another group refers to a radical of the formula-SO$_2$NR$^{16}$R$^{17}$, wherein R$^{16}$ and R$^{17}$ are each independently hydrogen, optionally substituted alkyl, or optionally substituted aryl, or R$^{16}$ and R$^{17}$ taken together with the nitrogen to which they are attached from a 3- to 8-membered heterocyclo group. Non-limiting exemplary sulfonamido groups include —SO$_2$NH$_2$, —SO$_2$N(H)CH$_3$, and —SO$_2$N(H)Ph.

For the purpose of the present disclosure, the term "alkylcarbonyl" as used by itself or as part of another group refers to a carbonyl group, i.e., —C(=O)—, substituted by an alkyl group. A non-limiting exemplary alkylcarbonyl group is —COCH$_3$.

For the purpose of the present disclosure, the term "arylcarbonyl" as used by itself or as part of another group refers to a carbonyl group, i.e., —C(=O)—, substituted by an optionally substituted aryl group. A non-limiting exemplary arylcarbonyl group is —COPh.

For the purpose of the present disclosure, the term "alkoxycarbonyl" as used by itself or as part of another group refers to a carbonyl group, i.e., —C(=O)—, substituted by an alkoxy group. Non-limiting exemplary alkoxycarbonyl groups include —C(=O)OMe, —C(=O)OEt, and —C(=O)OtBu.

For the purpose of the present disclosure, the term "alkylsulfonyl" as used by itself or as part of another group refers to a sulfonyl group, i.e., —SO$_2$—, substituted by any of the above-mentioned optionally substituted alkyl groups. A non-limiting exemplary alkylsulfonyl group is —SO$_2$CH$_3$.

For the purpose of the present disclosure, the term "arylsulfonyl" as used by itself or as part of another group refers to a sulfonyl group, i.e., —SO$_2$—, substituted by any of the above-mentioned optionally substituted aryl groups. A non-limiting exemplary arylsulfonyl group is —SO$_2$Ph.

For the purpose of the present disclosure, the term "mercaptoalkyl" as used by itself or as part of another group refers to any of the above-mentioned alkyl groups substituted by a —SH group.

For the purpose of the present disclosure, the term "carboxy" as used by itself or as part of another group refers to a radical of the formula-COOH.

For the purpose of the present disclosure, the term "carboxyalkyl" as used by itself or as part of another group refers to any of the above-mentioned alkyl groups substituted with a —COOH. A non-limiting exemplary carboxyalkyl group is —CH$_2$CO$_2$H.

For the purpose of the present disclosure, the terms "aralkyl" or "arylalkyl" as used by themselves or as part of another group refers to an alkyl group substituted with one, two, or three optionally substituted aryl groups. In one embodiment, the optionally substituted aralkyl group is a C$_{1-4}$ alkyl substituted with one optionally substituted aryl group. In one embodiment, the optionally substituted aralkyl group is a C$_1$ or C$_2$ alkyl substituted with one optionally substituted aryl group. In one embodiment, the optionally substituted aralkyl group is a C$_1$ or C$_2$ alkyl substituted with one optionally substituted phenyl group. Non-limiting exemplary optionally substituted aralkyl groups include benzyl, phenethyl, —CHPh$_2$, —CH$_2$(4-F-Ph), —CH$_2$(4-Me-Ph), —CH$_2$(4-CF$_3$-Ph), and —CH(4-F-Ph)$_2$.

For the purpose of the present disclosure, the terms "(heterocyclo)alkyl" as used by itself or part of another group refers to an alkyl group substituted with an optionally substituted heterocyclo group. In one embodiment, the (heterocyclo)alkyl is a C$_{1-4}$ alkyl substituted with one optionally substituted heterocyclo group. Non-limiting exemplary (heterocyclo)alkyl groups include:

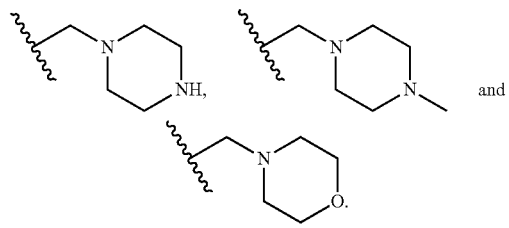

For the purpose of the present disclosure, the term "(carboxamido)alkyl" as used by itself or as part of another group refers to an alkyl group substituted with one or two carboxamido groups. In one embodiment, the (carboxamido)alkyl is a C$_{1-4}$ alkyl substituted with one carboxamido group. In another embodiment, the (carboxamido)alkyl is a $C_{1-4}$ alkyl substituted with two carboxamido groups. Non-limiting exemplary (carboxamido)alkyl groups include —$CH_2CONH_2$, —$C(H)CH_3$—$CONH_2$, —$CH_2CON(H)CH_3$, and —$CH(CO_2NH_2)CH_2CH_2CO$—$_2NH_2$ Throughout the specification and claims, a given chemical formula or name shall encompass all tautomers, congeners, and optical- and stereoisomers, as well as racemic mixtures where such isomers and mixtures exist.

Certain compounds of the present disclosure may possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as D- or L- for amino acids, and individual isomers are encompassed within the scope of the present disclosure. The compounds of the present disclosure do not include those which are known in art to be too unstable to synthesize and/or isolate. The present disclosure is meant to include compounds in racemic, scalemic, and optically pure forms. Optically active (R)- and (S)-, or D- and L-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Unless otherwise stated, structures depicted herein are also meant to include compounds which differ only in the presence of one or more isotopically enriched atoms. For example, compounds having the present structures with the replacement of a hydrogen by a deuterium or tritium, or the replacement of a carbon by $^{13}C$- or $^{14}C$-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present disclosure, whether radioactive or not, are encompassed within the scope of the present disclosure.

The compounds of the present disclosure may exist as salts. The present disclosure includes such salts. Examples of applicable salt forms include hydrochlorides, hydrobromides, sulfates, methanesulfonates, nitrates, maleates, acetates, citrates, fumarates, tartrates (e.g., (+)-tartrates, (−)-tartrates or mixtures thereof including racemic mixtures, succinates, benzoates and salts with amino acids, such as glutamic acid. These salts may be prepared by methods known to those skilled in art. Also included are base addition salts, such as sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent or by ion exchange. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids, such as arginate and the like, and salts of organic acids like glucuronic or galactunoric acids and the like. Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

The terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of +10%. In some embodiments, "about encompasses ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

Examples

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

EXAMPLES

Example 1 Isopropyl 2-(6-acetamido-2-((tert-butoxycarbonyl)amino)-hexanamido)-6-diazo-5-oxo-hexanoate (Compound 1)

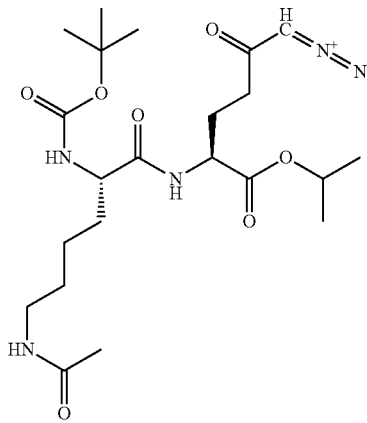 [SMILES: CC(=O)NCCCC[C@H](NC(=O)OC(C)(C)C)C(=O)N[C@@H](CCC(=O)C=[N+]=[N-])C(=O)OC(C)C]

Boc-L-Lys(Ac)—OH (446 mg, 1.55 mmol, 1.1 equiv.) and HBTU (641 mg, 1.69 mmol, 1.2 equiv.) were suspended in dry DCM (8 mL) and the suspension was cooled to 0° C. DIEA (546 mg, 735 µL, 4.22 mmol, 3 equiv.) was added. The reaction mixture was stirred for 5 min and then the solution of DONiPr (300 mg, 1.41 mmol, 1 equiv.) in dry DCM (2 mL) was added by syringe over 5 min. The reaction mixture was stirred for 0.5 h at 0° C. and for 1 h at rt under an inert atmosphere. Further DCM (30 mL) was added and the solution was washed with H$_2$O (2×50 mL), brine (50 mL) and dried over MgSO$_4$. The organic solvent was evaporated in vacuo. The residue was chromatographed on silica gel (DCM/MeOH, 25:1) to afford the desired product 1 (535 mg, 79%) as a light yellow amorphous solid.

$^1$H NMR (400 MHZ, CDCl$_3$): 1.22 (3H, d, J=6.3), 1.24 (3H, d, J=6.3), 1.36-1.44 (2H, m), 1.42 (9H, s), 1.46-1.56 (2H, m), 1.59-1.71 (1H, m), 1.73-1.87 (1H, m), 1.95 (3H, s), 1.97-2.04 (1H, m), 2.12-2.24 (1H, m), 2.34-2.47 (2H, m), 3.22 (2H, dq, J=6.5, 3.4), 4.09 (1H, q, J=7.0), 4.36-4.55 (1H, m), 5.00 (1H, hept, J=6.3), 5.26 (1H, d, J=7.3), 5.34 (1H, s), 6.05 (1H, bs), 7.12 (1H, d, J=7.0).

$^{13}$C NMR (101 MHz, CDCl$_3$): 21.82, 21.82, 22.41, 23.32, 26.90, 28.43 (3C), 28.87, 32.22, 36.56, 38.94, 52.18, 54.24, 55.11, 69.53, 80.00, 155.79, 170.42, 171.26, 172.29, 194.08.

IR (CHCl$_3$): 3431, 3325, 3116, 2984, 2937, 2867, 2110, 1728, 1708, 1668, 1635, 1518, 1499, 1468, 1387, 1394, 1376, 1369, 1241, 1147, 1166, 1105 cm$^{-1}$.

Optical rotation: $[\alpha]^{22}_D$ –22.6° (c 0.212, CH$_3$OH).

ESI MS: 506 ([M+Na]$^+$).

HR ESI MS: calcd for C$_{22}$H$_{37}$O$_7$N$_5$Na 506.25852; found 506.25866.

Example 2 Isopropyl 2-(2-((((9H-fluoren-9-yl)methoxy)carbonyl)amino)-6-acet-amidohexanamido)-6-diazo-5-oxohexanoate (Compound 2)

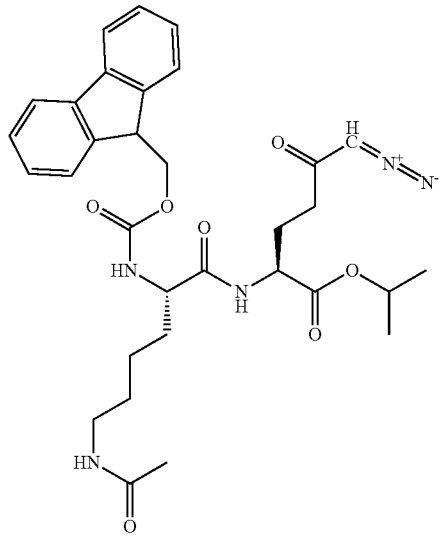 [SMILES: CC(=O)NCCCC[C@H](NC(=O)OCC1c2ccccc2-c2ccccc21)C(=O)N[C@@H](CCC(=O)C=[N+]=[N-])C(=O)OC(C)C]

Fmoc-L-Lys(Ac)—OH (6.35 g, 15.5 mmol, 1.1 equiv.) and HBTU (6.41 g, 16.9 mmol, 1.2 equiv.) were suspended in dry DCM (80 mL) and the suspension was cooled to 0° C. DIEA (5.46 g, 7.35 mL, 42.2 mmol, 3 equiv.) was added. The reaction mixture was stirred for 5 minutes and then the solution of DONiPr (3.00 g, 14.1 mmol, 1 equiv.) in dry DCM (20 mL) was added by syringe over 10 minutes. The reaction mixture was stirred for 0.5 h at 0° C. and for 1 h at rt under an inert atmosphere. DCM (30 mL) was added and the solution was washed with H$_2$O (2×50 mL), brine (50 mL) and dried over MgSO$_4$. The organic solvent was evaporated in vacuo. The residue was chromatographed on silica gel (CHCl$_3$/MeOH, 30:1) to afford the desired product 2 (5.72 g, 67%) as a light yellow amorphous solid.

$^1$H NMR (400 MHz, d$_6$-DMSO): 1.15 (3H, d, J=4.2), 1.17 (3H, d, J=4.2), 1.21-1.44 (4H, m), 1.47-1.67 (2H, m), 1.77 (3H, s), 1.77-1.85 (1H, m), 1.89-2.03 (1H, m), 2.31-2.43 (2H, m), 2.94-3.06 (2H, m), 3.90-4.09 (1H, m), 4.10-4.35 (4H, m), 4.87 (1H, hept, J=6.3), 6.01 (1H, bs), 7.32 (2H, t, J=7.4), 7.42 (2H, t, J=7.1), 7.47 (1H, d, J=8.1), 7.73 (2H, dd, J=8.8, 1.6), 7.79 (1H, t, J=5.4), 7.89 (2H, d, J=7.5), 8.26 (1H, d, J=7.5).

$^{13}$C NMR (101 MHz, do-DMSO): 21.46, 21.50, 22.64, 22.99, 25.87, 28.93, 31.60, 36.20, 38.41, 46.67, 51.48, 54.32, 54.92, 65.62, 67.98, 120.12, 125.34, 127.06, 127.65, 140.71, 140.72, 143.80, 143.91, 155.95, 168.93, 171.07, 172.34, 194.06.

IR (CHCl$_3$): 3450, 3420, 3318, 3270, 3117, 3069, 2986, 2939, 2865, 2110, 1727, 1668, 1638, 1579, 1504, 1479, 1465, 1451, 1386, 1377, 1233, 1184, 1146, 1105, 1033, 622, 426 cm$^{-1}$.

Optical rotation: $[\alpha]^{22}_D$ −18.9° (c 0.111, CH$_3$OH).

ESI MS: 628 ([M+Na]$^+$).

HR ESI MS: calcd for C$_{32}$H$_{39}$O$_7$N$_5$Na 628.27417; found 628.27430.

Example 3 Isopropyl 2-(6-acetamido-2-aminohexanamido)-6-diazo-5-oxohexanoate (Compound 3)

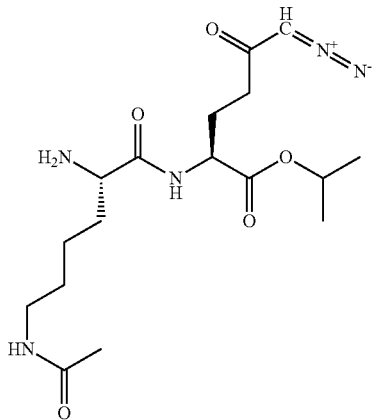 [SMILES: CC(=O)NCCCC[C@H](N)C(=O)N[C@@H](CCC(=O)C=[N+]=[N-])C(=O)OC(C)C]

Compound 2 (5.00 g, 8.26 mmol, 1 equiv.) was dissolved in dry DCM (150 ml) and diethylamine (3.51 g, 4.97 mL, 41.3 mmol, 5 equiv.) was added. The reaction mixture was stirred overnight at room temperature (20 h). The solvent was evaporated and crude product was purified on silica gel to afford 2.91 g (92%) of yellow solid compound 3.

$^1$H NMR (400 MHZ, CDCl$_3$): 1.20 (3H, d, J=6.0), 1.21 (3H, d, J=6.0), 1.33-1.53 (4H, m), 1.56-1.68 (1H, m), 1.72-1.84 (1H, m), 1.92 (3H, s), 1.91-2.02 (1H, m), 2.09-2.21 (1H, m), 2.28-2.48 (2H, m), 3.10-3.25 (2H, m), 3.43-3.73 (3H, m), 4.43 (1H, td, J=8.1, 4.7), 4.97 (1H, hept, J=6.0)), 5.46 (1H, bs), 6.51 (1H, bs), 8.05 (1H, d, J=7.7).

$^{13}$C NMR (101 MHz, CDCl$_3$): 21.76, 22.57, 23.22, 27.29, 29.06, 29.71, 33.92, 36.70, 39.06, 51.84, 54.53, 55.13, 69.40, 170.66, 171.24, 174.15, 194.15.

IR (KBr): 3432, 2110, 1731, 1635, 1615, 1547, 1453, 1377, 1217, 1106 cm$^{-1}$.

Optical rotation: $[\alpha]^{22}_D$ −8.8° (c 0.283, DMF).

ESI MS: 406 ([M+Na]$^+$).

HR ESI MS: calcd for C$_{17}$H$_{29}$O$_5$N$_5$Na 406.20609; found 406.20612.

Example 4 Isopropyl 2-(6-acetamido-2-palmitamidohexanamido)-6-diazo-5-oxohexanoate (Compound 4)

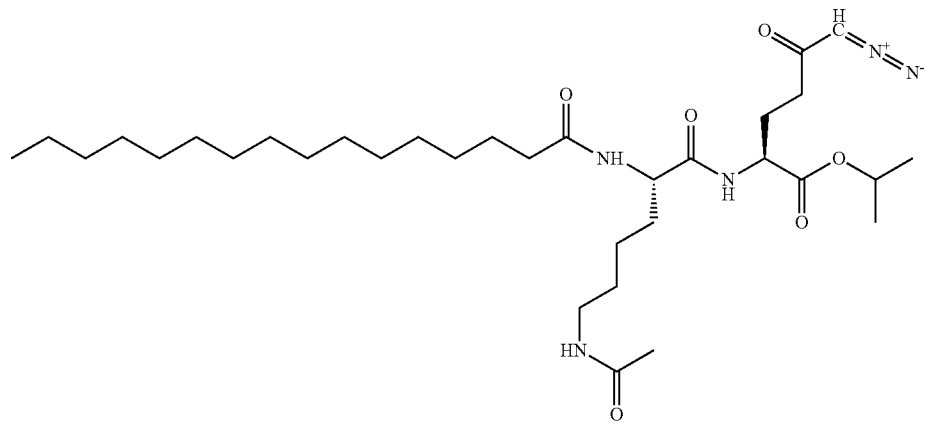 [SMILES: CCCCCCCCCCCCCCCC(=O)N[C@@H](CCCCNC(C)=O)C(=O)N[C@@H](CCC(=O)C=[N+]=[N-])C(=O)OC(C)C]

Palmitic acid (184 mg, 0.717 mmol, 1.1 equiv.) and HATU (298 mg, 0.782 mmol, 1.2 equiv.) were suspended in dry DCM (10 mL) and the suspension was cooled to 0° C. DIEA (253 mg, 341 μL, 1.96 mmol, 3 equiv.) was added. The reaction mixture was stirred for 5 min and then the solution of 3 (250 mg, 0.652 mmol, 1 equiv.) in dry DCM (5 mL) was added by syringe over 2 min. The reaction mixture was stirred for 15 min at 0° C. and 45 min at rt under an inert atmosphere. DCM (30 mL) was added and the solution was washed with $H_2O$ (2×50 mL), brine (50 mL) and dried over $MgSO_4$. The organic solvent was evaporated in vacuo. The residue was chromatographed on silica gel ($CHCl_3$/MeOH, 20:1) to afford the desired product 4 (255 mg, 63%) as an yellow solid.

$^1$H NMR (400 MHZ, $CDCl_3$): 0.86 (3H, d, J=6.8), 1.18-1.32 (30H, m), 1.34-1.44 (2H, m), 1.47-1.64 (4H, m), 1.65-1.74 (1H, m), 1.77-1.88 (1H, m), 1.96 (3H, s), 1.97-2.05 (1H, m), 2.13-2.24 (3H, m), 2.33-2.48 (2H, m), 3.23 (2H, q, J=6.3), 4.48 (2H, m), 5.00 (1H, hept, J=6.3), 5.35 (1H, bs), 6.14 (1H, t, J=5.8), 6.45 (1H, d, J=7.5), 7.35 (1H, d, J=6.4).

$^{13}$C NMR (101 MHZ, $CDCl_3$): 14.24, 21.83, 21.85, 22.11, 22.80, 23.31, 25.86, 26.59, 28.76, 29.47 (2C), 29.49, 29.64, 29.77 (2C), 29.78, 29.81 (3C), 32.03, 32.07, 36.53, 36.71, 38.75, 52.35, 52.70, 55.18, 69.52, 170.58, 171.23, 172.08, 173.58, 194.13.

IR ($CHCl_3$): 3447, 3417, 3314, 2928, 2871, 2855, 2110, 1731, 1659, 1525, 1507, 1467, 1456, 1385, 1377, 1367, 1236, 1105 $cm^{-1}$.

Optical rotation: $[\alpha]^{20}_D$-6.0° (c 0.380, $CHCl_3$).

ESI MS: 644 ($[M+Na]^+$).

HR ESI MS: calcd for $C_{33}H_{59}O_6N_5Na$ 644.43576; found 644.43572.

Example 5 Isopropyl 2-(6-acetamido-2-(4-phenyl-but-3-enamido)hexanamido)-6-diazo-5-oxohexanoate (Compound 5)

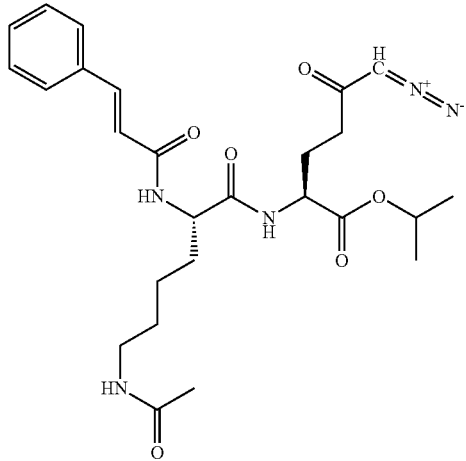 [SMILES: CC(=O)NCCCC[C@H](NC(=O)/C=C/c1ccccc1)C(=O)N[C@@H](CCC(=O)C=[N+]=[N-])C(=O)OC(C)C]

trans-Cinnamic acid (106 mg, 0.717 mmol, 1.1 equiv.) and HATU (298 mg, 0.782 mmol, 1.2 equiv.) were suspended in dry DCM (10 mL) and the suspension was cooled to 0° C. DIEA (253 mg, 341 μL, 1.96 mmol, 3 equiv.) was added. The reaction mixture was stirred for 5 min and then the solution of 3 (250 mg, 0.652 mmol) in dry DCM (5 mL) was added by syringe over 2 min. The reaction mixture was stirred for 15 min at 0° C. and 45 min at rt under an inert atmosphere. DCM (30 mL) was added and the solution was washed with $H_2O$ (2×50 mL), brine (50 mL) and dried over $MgSO_4$. DCM was evaporated and the residue was chromatographed on silica gel ($CHCl_3$/MeOH, 20:1) to afford compound 5 (271 mg, 81%) as an light yellow solid.

$^1$H NMR (400 MHZ, $CDCl_3$): 1.21 (3H, d, J=6.4), 1.23 (3H, d, J=6.4), 1.38-1.59 (4H, m), 1.72-1.83 (1H, m), 1.84-1.93 (1H, m), 1.94 (3H, s), 1.94-2.05 (1H, m), 2.15-2.25 (1H, m), 2.32-2.46 (2H, m), 3.14-3.29 (2H, m), 4.45 (1H, dq, J=8.3, 4.7), 4.68 (1H, q, J=7.5), 5.00 (1H, hept, J=6.4), 5.33 (1H, bs), 6.40 (1H, t, J=5.4), 6.59 (1H, d, J=15.7), 7.23 (1H, d, J=7.7), 7.28-7.34 (3H, m), 7.43-7.49 (2H, m), 7.61 (1H, d, J=15.7), 7.71 (1H, d, J=7.1).

$^{13}$C NMR (101 MHZ, $CDCl_3$): 21.80, 21.81, 22.30, 23.28, 26.68, 28.89, 32.11, 36.51, 38.80, 52.29, 53.09, 55.06, 69.44, 120.56, 127.92 (2C), 128.93 (2C), 129.92, 134.73, 141.50, 166.25, 170.67, 171.22, 172.24, 193.97.

IR ($CHCl_3$): 3447, 3412, 3304, 3027, 2110, 1731, 1660, 1629, 1600, 1579, 1528, 1507, 1494, 1450, 1387, 1376, 1370, 1233, 1105, 1082, 1029, 988, 977, 907, 712, 561 $cm^{-1}$.

Optical rotation: $[\alpha]^{20}_D$-5.3° (c 0.285, $CHCl_3$).

ESI MS: 536 ($[M+Na]^+$).

HR ESI MS: calcd for $C_{26}H_{35}O_6N_5Na$ 536.24795; found 536.24797.

Example 6 Isopropyl 2-(6-acetamido-2-octanamido-hexanamido)-6-diazo-5-oxohexanoate (Compound 6)

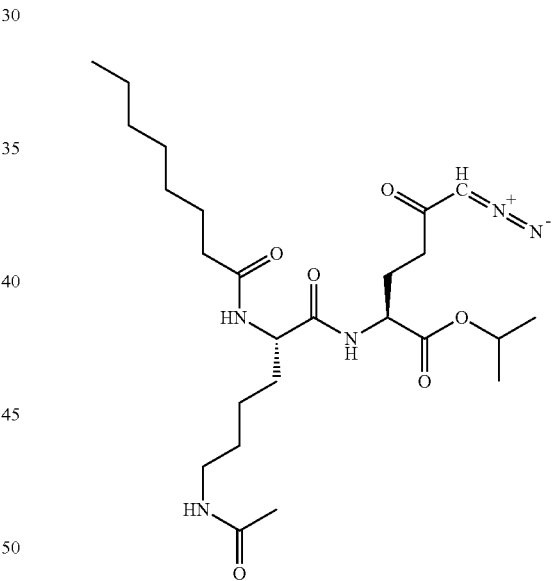

Octanoic acid (103 mg, 0.717 mmol, 1.1 equiv.) and HATU (298 mg, 0.782 mmol, 1.2 equiv.) were suspended in dry DCM (10 mL) and the suspension was cooled to 0° C. DIEA (253 mg, 341 μL, 1.96 mmol, 3 equiv.) was added. The reaction mixture was stirred for 5 min and then the solution of 3 (250 mg, 0.652 mmol, 1 equiv.) in dry DCM (5 mL) was added by syringe over 2 min. The reaction mixture was stirred for 15 min at 0° C. and 45 min at rt under an inert atmosphere. DCM (30 mL) was added and the solution was washed with $H_2O$ (2×50 mL), brine (50 mL) and dried over $MgSO_4$. DCM was evaporated and the residue was chromatographed on silica gel ($CHCl_3$/MeOH, 20:1) to afford the desired product 6 (216 mg, 65%) as an light yellow solid.

¹H NMR (400 MHZ, CDCl₃): 0.87 (3H, t, J=7.0), 1.24 (3H, d, J=6.3), 1.27 (3H, d, J=6.3), 1.26-1.32 (6H, m), 1.35-1.45 (2H, m), 1.49-1.60 (2H, m), 1.60-1.75 (5H, m), 1.80-1.91 (1H, m), 1.97 (3H, s), 1.99-2.07 (1H, m), 2.15-2.21 (1H, m), 2.22 (2H, t, J=6.9), 2.37-2.49 (2H, m), 3.25 (2H, q, J=6.2), 4.44 (2H, m), 5.03 (1H, hept, J=6.3), 5.34 (1H, bs), 5.97 (1H, t, J=6.3), 6.31 (1H, d, J=7.7), 7.17 (1H, d, J=5.5).

¹³C NMR (101 MHz, CDCl₃): 14.12, 21.78 (2C), 22.13, 22.65, 23.21, 25.81, 26.58, 28.74, 29.07, 29.33, 29.74, 31.74, 32.08, 36.60, 38.75, 52.27, 52.67, 55.08, 69.40, 170.56, 171.19, 172.15, 173.56, 194.04.

IR (CHCl₃): 3449, 3417, 3313, 2931, 2858, 2827, 2110, 1731, 1659, 1524, 1508, 1387, 1377, 1370, 1235, 1106 cm⁻¹.

Optical rotation: $[\alpha]^{20}_D$ −4.8° (c 0.227, CHCl₃).

ESI MS: 532 ([M+Na]⁺).

HR ESI MS: calcd for $C_{25}H_{43}O_6N_5Na$ 532.31056, found 532.31063.

Example 7 Isopropyl 2-(6-acetamido-2-adamantane-1-carboxamido)hexanamido)-6-diazo-5-oxohexanoate (Compound 7)

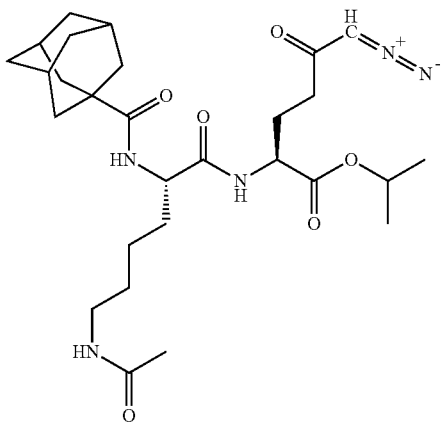

1-Adamantanecarboxylic acid (129 mg, 0.717 mmol, 1.1 equiv.) and HATU (298 mg, 0.782 mmol, 1.2 equiv.) were suspended in dry DCM (10 mL) and the suspension was cooled to 0° C. DIEA (253 mg, 341 μL, 1.96 mmol, 3 equiv.) was added. The reaction mixture was stirred for 5 min and then the solution of 3 (250 mg, 0.652 mmol, 1 equiv.) in dry DCM (10 mL) was added by syringe over 2 min. The reaction mixture was stirred for 15 min at 0° C. and for 45 min at rt under an inert atmosphere. DCM (30 mL) was added and the solution was washed with H₂O (2×50 mL), brine (50 mL) and dried over MgSO₄. DCM was evaporated in vacuo. The residue was chromatographed on silica gel (CHCl₃/MeOH, 20:1) to afford the desired product 7 (292 mg, 82%) as an light yellow solid.

¹H NMR (400 MHZ, CDCl₃): 1.24 (3H, d, J=6.3), 1.27 (3H, d, J=6.3), 1.33-1.44 (2H, m), 1.49-1.61 (2H, m), 1.64-1.79 (7H, m), 1.82-1.89 (7H, m), 1.97 (3H, s), 1.99-2.07 (4H, m), 2.13-2.25 (1H, m), 2.33-2.48 (2H, m), 3.15-3.34 (2H, m), 4.37-4.49 (2H, m), 5.02 (1H, hept, J=6.3), 5.33 (1H, bs), 6.04 (1H, bs), 6.36 (1H, d, J=6.8), 7.18 (1H, bs).

¹³C NMR (101 MHz, CDCl₃): 21.72, 21.74, 22.05, 23.13, 26.47, 28.04 (3C), 28.57, 32.34, 36.42 (3C), 36.58, 38.82, 39.16 (3C), 40.64, 52.15, 52.24, 54.99, 69.30, 170.44, 171.15, 172.21, 178.14, 193.94.

IR (CHCl₃): 3448, 3419, 3316, 2931, 2912, 2853, 2110, 1731, 1658, 1640, 1541, 1518, 1504, 1453, 1387, 1377, 1370, 1347, 1319, 1236, 1105, 976 cm⁻¹.

Optical rotation: $[\alpha]^{20}_D$ −4.1° (c 0.220, CHCl₃).

ESI MS: 568 ([M+Na]⁺).

HR ESI MS: calcd for $C_{28}H_{43}O_6N_5Na$ 568.31056; found 568.31055.

Example 8 Isopropyl 2-(6-acetamido-2-(((benzyloxy)carbonyl)amino)hexanamido)-6-diazo-5-oxohexanoate (Compound 8)

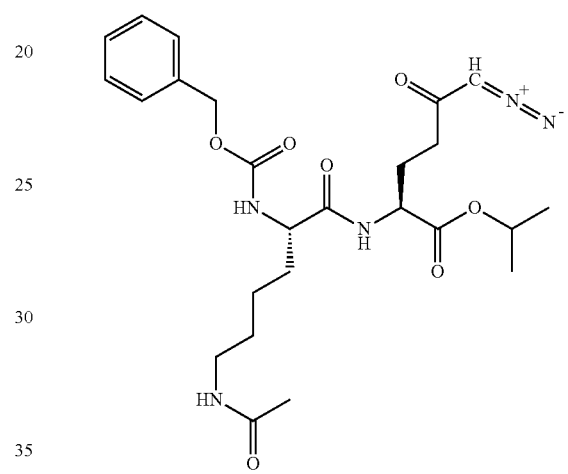

Compound 3 (250 mg, 0.652 mmol, 1 equiv.) was dissolved in dry DCM (10 mL) and reaction mixture was cooled to 0° C. TEA (82 mg, 114 μL, 0.815 mmol, 1.25 equiv.) followed by solution of benzyl carbonochloridate (133 mg, 112 μL, 0.782 mmol, 1.2 equiv.) in dry DCM (2 mL) were added. Resulting mixture was stirred for 15 min at 0° C. and for 45 min at rt. DCM was evaporated and the residue was purified by LC (CHCl₃/MeOH 10:1) to afforded compound 8 (203 mg, 60%) as a light yellow solid.

¹H NMR (400 MHZ, CDCl₃): 1.24 (3H, d, J=6.2), 1.26 (3H, d, J=6.2), 1.37-1.59 (3H, m), 1.63-1.74 (1H, m), 1.74-1.90 (2H, m), 1.94 (3H, s), 1.94-2.06 (1H, m), 2.11-2.26 (1H, m), 2.29-2.50 (2H, m), 3.16-3.32 (2H, m), 4.19 (1H, q, J=7.0), 4.45 (1H, td, J=8.1, 4.5), 5.02 (1H, hept, J=6.2), 5.10 (2H, bs), 5.26 (1H, bs), 5.56 (1H, d, J=7.7), 5.91 (1H, bs), 7.11 (1H, bs), 7.27-7.41 (5H, m).

¹³C NMR (101 MHz, CDCl₃): 21.80, 21.81, 22.20, 23.27, 26.67, 28.79, 29.78, 32.30, 36.50, 38.87, 52.27, 54.59, 55.18, 66.97, 69.53, 128.01 (2C), 128.24, 128.61 (2C), 136.40, 170.48, 171.23, 171.96, 194.16.

IR (CHCl₃): 3450, 3419, 3316, 3116, 3092, 3068, 3026, 2985, 2930, 2873, 2856, 2110, 1727, 1668, 1635, 1587, 1506, 1466, 1455, 1388, 1377, 1349, 1233, 1184, 1146, 1105, 1082, 1063, 1041, 1029, 1004, 698 cm⁻¹.

Optical rotation: $[\alpha]^{20}_D$ +9.3° (c 0.043, CHCl₃).

ESI MS: 540 ([M+Na]⁺).

HR ESI MS: calcd for $C_{25}H_{35}O_7N_5Na$ 540.24287; found 540.24292.

Example 9 Isopropyl 2-(6-acetamido-2-((((adamantan-1-yl)oxy)carbonyl)amino)-hexanamido)-6-diazo-5-oxohexanoate (Compound 9)

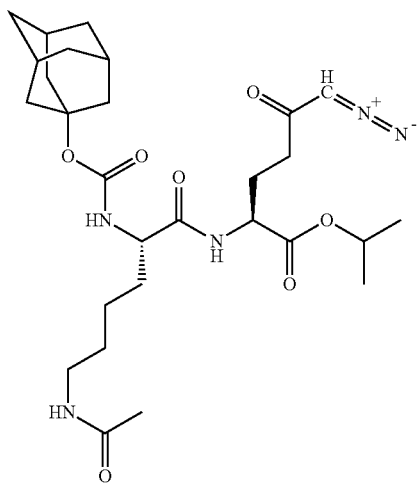

Compound 3 (250 mg, 0.652 mmol, 1 equiv.) was dissolved in dry DCM (10 mL) and reaction mixture was cooled to 0° C. TEA (79 mg, 109 μL, 0.782 mmol, 1.2 eqiv.) followed by solution of adamantanyl carbonochloridate (168 mg, 0.782 mmol, 1.2 equiv.) in dry DCM (3 mL) were added. Resulting mixture was stirred for 15 min at 0° C. and for 45 min at rt. DCM was evaporated and the crude product was purified by LC (CHCl$_3$/MeOH 20:1). The desired compound 9 was obtained in 55% yield (201 mg) as a light yellow solid.

$^1$H NMR (400 MHZ, CDCl$_3$): 1.24 (3H, d, J=6.3), 1.26 (3H, d, J=6.3), 1.37-1.46 (2H, m), 1.49-1.58 (2H, m), 1.59-1.69 (7H, m), 1.76-1.89 (1H, m), 1.97 (3H, s), 2.06-2.11 (6H, m), 2.11-2.18 (4H, m), 2.15-2.26 (1H, m), 2.30-2.52 (2H, m), 3.16-3.32 (2H, m), 4.08 (1H, q, J=6.9), 4.47 (1H, ddd, J=8.5, 7.5, 4.4), 5.03 (1H, hept, J=6.3), 5.16 (1H, d, J=7.2), 5.32 (1H, bs), 5.86 (1H, bs), 6.96 (1H, d, J=6.5).

$^{13}$C NMR (101 MHZ, CDCl$_3$): 21.79 (2C), 22.42, 23.28, 26.88, 28.81, 30.89 (3C), 36.22 (3C), 36.53, 38.93, 41.69 (3C), 45.40, 52.13, 54.15, 55.06, 69.48, 79.84, 155.41, 170.42, 171.25, 172.31, 194.05.

IR (CHCl$_3$): 3598, 3445, 3420, 2933, 2918, 2854, 2110, 1730, 1706, 1669, 1637, 1518, 1494, 1456, 1386, 1377, 1367, 1354, 1318, 1272, 1236, 1111, 1104, 1086, 1057, 968, 551 cm$^{-1}$.

Optical rotation: $[\alpha]^{20}_D$ −2.0° (c 0.151, CHCl$_3$).

ESI MS: 584 ([M+Na]$^+$).

HR ESI MS: calcd for C$_{28}$H$_{43}$O$_7$N$_5$Na 584.30547; found 584.30551.

Example 10 Isopropyl 2-(2-(2-(1H-indol-3-yl)acetamido)-6-acetamidohexan-amido)-6-diazo-5-oxohexanoate (Compound 10)

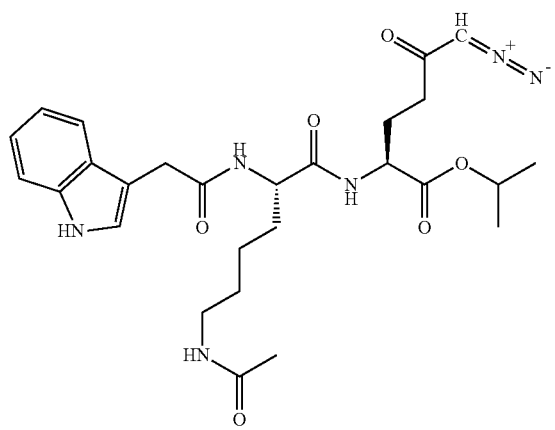

3-Indolylacetic acid (126 mg, 0.717 mmol, 1.1 equiv.) and HATU (298 mg, 0.782 mmol, 1.2 equiv.) were dissolved in anhydrous DCM (8 mL) and the reaction mixture was cooled to 0° C. DIEA (253 mg, 341 μL, 1.96 mmol, 3 eqiv.) was added and reaction mixture was stirred for 15 min at the same temperature. Finally the solution of compound 3 (250 mg, 0.652 mmol, 1 equiv.) in anhydrous DCM (4 mL) was added dropwise. The mixture was stirred at 0° C. for further 30 min and at rt for 3 h. DCM (30 mL) was added and the organic phase was washed with 10% NaHCO$_3$ (50 mL), H$_2$O (50 mL) and brine, dried over MgSO$_4$ and the solvent was evaporated. The crude product was purified by column chromatography (CHCl$_3$/MeOH 20:1). The desired product 10 was obtained as a light yellow solid (189 mg, 53% yield).

$^1$H NMR (400 MHZ, CDCl$_3$): 1.22 (3H, d, J=6.3), 1.24 (3H, d, J=6.3), 1.20-1.26 (2H, m), 1.35-1.47 (2H, m), 1.48-1.61 (1H, m), 1.70-1.81 (1H, m), 1.86-1.95 (1H, m), 1.93 (3H, s), 2.08-2.19 (1H, m), 2.21-2.37 (2H, m), 3.13 (2H, q, J=6.5), 3.75 (2H, bs), 4.33-4.45 (2H, m), 5.00 (1H, hept, J=6.3), 5.14 (1H, bs), 5.82 (1H, bs), 6.37 (1H, d, J=7.6), 7.06 (1H, d, J=6.4), 7.13 (1H, ddd, J=8.0, 7.1, 1.1), 7.17 (1H, d, J=2.1), 7.21 (1H, ddd, J=8.0, 7.1, 1.1), 7.38 (1H, dd, J=8.1, 0.9), 7.58 (1H, dd, J=7.8, 1.0), 8.43 (1H, bs).

$^{13}$C NMR (101 MHz, CDCl$_3$): 21.83 (2C), 22.24, 23.29, 26.64, 28.73, 31.77, 33.50, 36.39, 38.99, 52.24, 52.95, 55.07, 69.53, 108.73, 111.69, 118.66, 119.89, 122.48, 123.94, 127.14, 136.53, 170.61, 171.20, 171.87, 172.10, 194.23.

IR (KBr): 3304, 3081, 3062, 2106, 1732, 1647, 1542, 1458, 1437, 1375, 1215, 1106 cm$^{-1}$.

Optical rotation: $[\alpha]^{20}_D$ −1.9° (c 0.260, CHCl$_3$).

ESI MS: 563 ([M+Na]$^+$).

HR ESI MS: calcd for C$_{27}$H$_{36}$O$_6$N$_6$Na 563.25885; found 563.25890.

Example 11 Isopropyl 2-(6-acetamido-2-(2-amino-3-(1H-indol-3-yl)propanamido)hexanamido)-6-diazo-5-oxohexanoate (Compound 11)

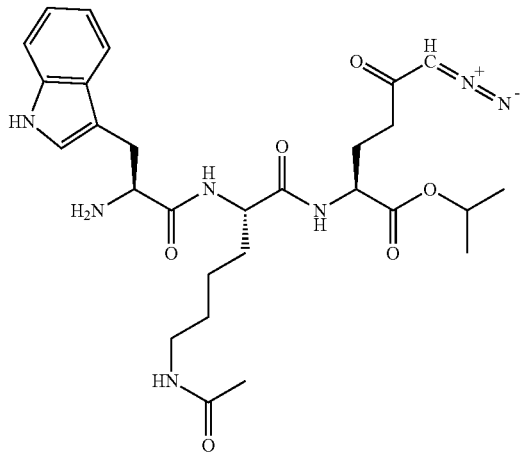

Fmoc-L-Trp-OH (306 mg, 0.717 mmol, 1.1 equiv.) and HATU (298 mg, 0.782 mmol, 1.2 equiv.) were dissolved in anhydrous DMF (8 mL) and the reaction mixture was cooled to 0° C. DIEA (253 mg, 341 µL, 1.96 mmol, 3 eqiv.) was added and reaction mixture was stirred for 15 min at the same temperature. Finally the solution of 3 (250 mg, 0.652 mmol, 1 equiv.) in anhydrous DMF (4 mL) was added dropwise. The mixture was stirred at 0° C. for further 30 min and at rt for 3 h. Diethylamine (477 mg, 674 µL, 6.52 mmol, 10 eqiv.) was added to the mixture to remove Fmoc protecting group and the solution was stirred overnight at rt under an inert atmosphere. DMF was evaporated. DCM (100 mL) was added and the crude product was purified by LC (CHCl$_3$/MeOH 7:1). The desired product 11 (194 mg, 52% yield) was obtained as a light yellow solid.

$^1$H NMR (400 MHZ, d$_6$-DMSO): 1.16 (3H, d, J=6.3), 1.18 (3H, d, J=6.3), 1.18-1.24 (2H, m), 1.29-1.41 (2H, m), 1.42-1.54 (1H, m), 1.55-1.67 (1H, m), 1.78 (3H, s), 1.78-1.86 (1H, m), 1.90-2.03 (1H, m), 2.32-2.45 (2H, m), 2.79 (1H, dd, J=14.4, 8.4), 2.97 (1H, q, J=6.8), 3.11 (1H, dd, J=14.3, 4.2), 2.08 (2H, bs), 3.55 (dd, 1H, J=8.4, 4.3), 4.16 (1H, ddd, J=9.1, 7.2, 5.2), 4.32 (1H, td, J=7.8, 5.2), 4.88 (1H, hept, J=6.3), 6.04 (1H, bs), 6.97 (1H, ddd, J=7.9, 7.0, 1.1), 7.06 (1H, ddd, J=8.1, 6.9, 1.2), 7.18 (1H, d, J=2.4), 7.33 (1H, dt, J=8.1, 0.9), 7.58 (1H, d, J=7.9), 7.79 (1H, t, J=5.6), 8.11 (1H, d, J=8.2), 8.37 (1H, d, J=7.3), 10.87 (1H, d, J=2.4).

$^{13}$C NMR (101 MHz, d$_6$-DMSO): 21.45, 21.50, 22.34, 22.62, 25.76, 28.98, 30.37, 32.36, 38.43, 41.56, 51.52, 51.68, 54.80, 56.03, 68.00, 110.05, 111.33, 118.23, 118.45, 120.90, 123.99, 127.39, 136.24, 168.95, 170.97, 171.71, 173.59, 194.03.

IR (KBr): 3277, 3084, 2105, 1731, 1666, 1643, 1545, 1457, 1439, 1375, 1212, 1106 cm$^{-1}$.

Optical rotation: $[\alpha]^{20}_D$ –37.6° (c 0.226, CHCl$_3$).

ESI MS: 570 ([M+H]$^+$).

HR ESI MS: calcd for C$_{28}$H$_{40}$O$_6$N$_7$ 570.30346; found 570.30349.

Example 12 Isopropyl 2-(6-acetamido-2-(2-acetamido-3-(1H-indol-3-yl)propan-amido) hexanamido)-6-diazo-5-oxohexanoate (Compound 12)

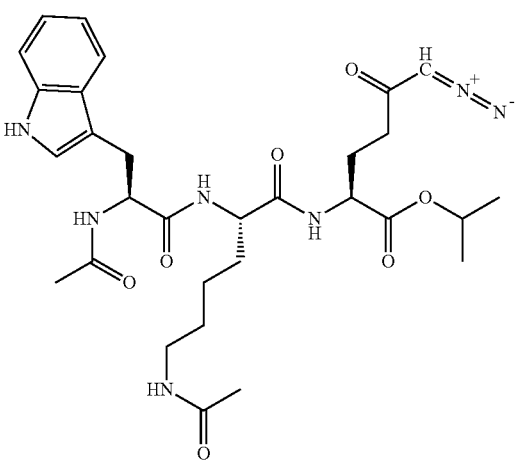

Starting material 11 (150 mg, 0.263 mmol, 1 equiv.) was dissolved in anhydrous DMF (5 mL) and pyridine (42 mg, 42 µL, 0.527 mmol, 2 equiv.) followed by acetic anhydride (32 mg, 30 µL, 0.316 mmol, 1.2 equiv.) were added. Resulting mixture was stirred for 2 h at rt under an inert atmosphere. DMF was evaporated and the residue was purified by LC (CHCl$_3$/MeOH 10:1) to obtained compound 12 (129 mg, 80%) as a light yellow solid.

$^1$H NMR (400 MHZ, d$_4$-MeOD): 1.25 (3H, d, J=6.3), 1.26 (3H, d, J=6.3), 1.30-1.37 (2H, m), 1.42-1.54 (2H, m), 1.55-1.68 (1H, m), 1.72-1.84 (1H, m), 1.85-1.93 (1H, m), 1.93 (3H, s), 1.94 (3H, s), 2.10-2.22 (1H, m), 2.36-2.47 (2H, m), 3.08-3.18 (3H, m), 3.28 (1H, dd, J=9.2, 6.0), 4.27 (1H, dd, J=8.4, 5.7), 4.33 (1H, dd, J=9.5, 4.9), 4.69 (1H, dd, J=7.6, 5.9), 5.01 (1H, hept, J=6.3), 5.72 (1H, bs), 7.02 (1H, t, J=7.4), 7.10 (1H, t, J=7.4), 7.14 (1H, s), 7.34 (1H, d, J=8.0), 7.61 (1H, d, J=7.8).

$^{13}$C NMR (101 MHZ, d$_4$-MeOD): 21.99 (2C), 22.57, 22.60, 23.96, 27.59, 28.73, 29.93, 32.50, 37.25, 40.19, 53.19, 54.62, 55.66, 56.22, 70.34, 110.83, 112.30, 119.34, 119.81, 122.44, 124.53, 128.86, 137.99, 172.42, 173.20, 173.26, 174.07 (2C), 196.98.

IR (KBr): 3295, 3090, 3063, 2107, 1729, 1660, 1644, 1542, 1459, 1437, 1375, 1231, 1106 cm$^{-1}$.

Optical rotation: $[\alpha]^{20}_D$ –18.0° (c 0.260, DMF).

ESI MS: 634 ([M+Na]$^+$).

HR ESI MS: calcd for C$_{30}$H$_{41}$O$_7$N$_7$Na 634.29597; found 634.29598.

Example 13 Isopropyl 2-(6-acetamido-2-(2-amino-3-phenylpropanamido)-hexanamido)-6-diazo-5-oxo-hexanoate (Compound 13)

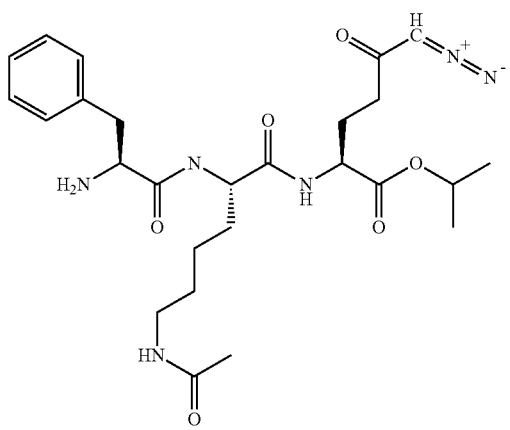

Fmoc-L-Phe-OH (278 mg, 0.717 mmol, 1.1 equiv.) and HATU (298 mg, 0.782 mmol, 1.2 equiv.) were dissolved in anhydrous DMF (8 mL) and the reaction mixture was cooled to 0° C. DIEA (253 mg, 341 µL, 1.96 mmol, 3 eqiv.) was added and reaction mixture was stirred for 15 min at the same temperature. Finally the solution of 3 (250 mg, 0.652 mmol, 1 equiv.) in anhydrous DMF (4 mL) was added dropwise. The mixture was stirred at 0° C. for further 30 min and at rt for 3 h. Diethylamine (477 mg, 674 µL, 6.52 mmol, 10 eqiv.) was added to the mixture to remove Fmoc protecting group and the solution was stirred overnight at rt under an inert atmosphere. DMF was evaporated and the crude product was purified by LC (CHCl$_3$/MeOH 20:1). The desired product 13 (221 mg, 64% yield) was obtained as a light yellow solid.

$^1$H NMR (400 MHZ, CDCl$_3$): 1.23 (3H, d, J=6.3), 1.25 (3H, d, J=6.3), 1.19-1.28 (2H, m), 1.29-1.39 (2H, m), 1.46-1.57 (2H, m), 1.62-1.72 (1H, m), 1.78-1.89 (1H, m), 1.95 (3H, s), 1.95-2.04 (1H, m), 2.09-2.22 (1H, m), 2.32-2.49 (2H, m), 2.72 (1H, ddd, J=13.8, 9.2, 1.5), 3.15-3.29 (3H, m), 3.66 (1H, ddd, J=9.2, 3.9, 1.5), 4.37-4.48 (2H, m), 5.01 (1H, hept, J=6.3), 5.34 (1H, bs), 6.09 (1H, bs), 7.18-7.25 (3H, m), 7.28-7.33 (2H, m), 7.36 (1H, bs), 7.88 (1H, d, J=8.5).

$^{13}$C NMR (101 MHz, CDCl$_3$): 21.86 (2C), 22.36, 23.35, 26.50, 28.80, 31.95, 36.59, 38.99, 40.96, 52.41, 52.55, 55.20, 56.45, 69.52, 127.02, 128.84 (2C), 129.42 (2C), 137.67, 170.44, 171.23, 171.84, 174.64, 194.27.

IR (CHCl$_3$): 3449, 3358, 3334, 2984, 2110, 1731, 1661, 1648, 1632, 1515, 1496, 1467, 1388, 1376, 1349, 1184, 1146, 1105, 1031, 703 cm$^{-1}$.

Optical rotation: $[\alpha]^{20}_D$ –23.3° (c 0.073, CHCl$_3$).

ESI MS: 553 ([M+Na]$^+$).

HR ESI MS: calcd for C$_{26}$H$_{38}$O$_6$N$_6$Na 553.27450; found 553.27490.

Example 14 Isopropyl 2-(6-acetamido-2-(2-acetamido-3-phenylpropanamido)-hexanamido)-6-diazo-5-oxohexanoate (Compound 14)

Starting material 13 (150 mg, 0.283 mmol, 1 equiv.) was dissolved in anhydrous DMF (5 mL) and pyridine (45 mg, 46 µL, 0.565 mmol, 2 equiv.) followed by acetic anhydride (35 mg, 32 µL, 0.339 mmol, 1.2 equiv.) were added. Resulting mixture was stirred for 2 h at rt under an inert atmosphere. DMF was evaporated and the residue was purified by LC (CHCl$_3$/MeOH 20:1) to obtain compound 14 (125 mg, 77%) as a light yellow solid.

$^1$H NMR (400 MHZ, d$_6$-DMSO): 1.17 (3H, d, J=6.3), 1.18 (3H, d, J=6.3), 1.23-1.31 (2H, m), 1.32-1.43 (2H, m), 1.46-1.59 (1H, m), 1.60-1.72 (1H, m), 1.74 (3H, s), 1.78 (3H, s), 1.78-1.85 (1H, m), 1.90-2.01 (1H, m), 2.33-2.44 (2H, m), 2.70 (1H, dd, J=14.0, 10.4), 2.95-3.03 (3H, m). 4.16 (1H, ddd, J=9.3, 7.4, 5.2), 4.23 (1H, td, J=8.3, 5.3), 4.51 (1H, ddd, J=10.2, 8.3, 4.0), 4.88 (1H, hept, J=6.3), 6.04 (1H, bs), 7.14-7.21 (1H, m), 7.22-7.30 (4H, m), 7.79 (1H, t, J=5.6), 8.03 (1H, d, J=7.9), 8.07 (1H, d, J=8.3), 8.25 (1H, d, J=7.4).

$^{13}$C NMR (101 MHZ, d$_6$-DMSO): 21.93, 21.97, 22.92, 23.09, 23.14, 26.31, 29.44, 32.25, 37.88, 38.85, 51.92, 52.74, 54.35, 56.03, 68.45, 126.64, 128.46, 129.56, 138.53, 169.38, 169.70, 171.44, 171.80, 172.18, 194.51.

IR (KBr): 3283, 3082, 3033, 2102, 1725, 1685, 1638, 1547, 1498, 1454, 1388, 1374, 1282, 1224, 1108, 701 cm$^{-1}$.

Optical rotation: $[\alpha]^{20}_D$ –14.7° (c 0.156, DMF).

ESI MS: 595 ([M+Na]$^+$).

HR ESI MS: calcd for C$_{28}$H$_{40}$O$_7$N$_6$Na 595.28507; found 595.28522.

Example 15 Isopropyl 2-(6-acetamido-2-(1,2,3,4-tetrahydroisoquinoline-3-carboxamido)hexanamido)-6-diazo-5-oxohexanoate (Compound 15)

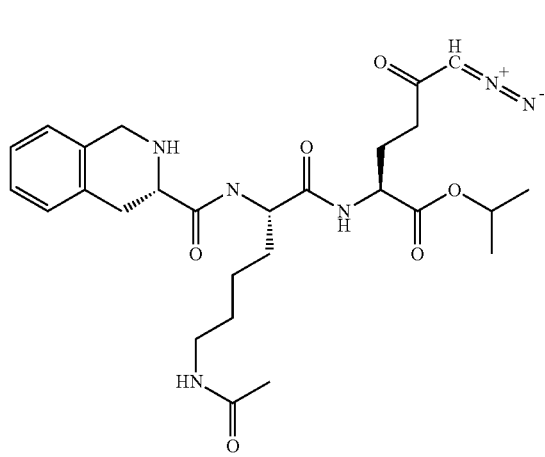

Fmoc-L-Tic-OH (286 mg, 0.717 mmol, 1.1 equiv.) and HATU (298 mg, 0.782 mmol, 1.2 equiv.) were dissolved in anhydrous DMF (8 mL) and the reaction mixture was cooled to 0° C. DIEA (253 mg, 341 µL, 1.96 mmol, 3 eqiv.) was added and reaction mixture was stirred for 15 min at the same temperature. Finally the solution of 3 (250 mg, 0.652 mmol, 1 equiv.) in anhydrous DMF (4 mL) was added dropwise. The mixture was stirred at 0° C. for further 30 min and at rt for 3 h. Diethylamine (477 mg, 674 µL, 6.52 mmol, 10 eqiv.) was added to the mixture to remove Fmoc protecting group and the solution was stirred overnight at rt under an inert atmosphere. DMF was evaporated and the crude product was purified by LC (CHCl$_3$/MeOH 10:1). The desired product 15 (202 mg, 57% yield) was obtained as a light yellow solid.

$^1$H NMR (400 MHZ, d$_6$-DMSO): 1.17 (3H, d, J=6.3), 1.19 (3H, d, J=6.3), 1.20-1.28 (2H, m), 1.29-1.41 (2H, m), 1.46-1.58 (1H, m), 1.59-1.71 (1H, m), 1.77 (3H, s), 1.77-1.86 (1H, m), 1.92-2.03 (1H, m), 2.35-2.47 (2H, m), 2.72 (1H, dd, J=16.3, 10.0), 2.92 (1H, dd, J=16.3, 4.9), 2.98 (2H, q, J=6.9), 3.46 (1H, dd, J=9.7, 4.8), 3.82-3.95 (2H, m), 4.17 (1H, ddd, J=9.3, 7.3, 5.1), 4.33 (1H, dt, J=8.2, 5.1), 4.89 (1H, hept, J=6.3), 6.07 (1H, bs), 7.01-7.08 (1H, m), 7.08-7.16 (4H, m), 7.77 (1H, t, J=5.6), 7.93 (1H, d, J=8.3), 8.38 (1H, d, J=7.4).

$^{13}$C NMR (101 MHZ, d$_6$-DMSO): 21.46, 21.50, 22.43, 22.60, 25.76, 28.92, 30.84, 32.32, 36.20, 38.37, 46.51, 51.49, 51.67, 55.63, 55.71, 68.01, 125.62, 125.70, 125.87, 128.81, 134.44, 136.21, 168.87, 170.97, 171.75, 172.28, 194.04.

IR (KBr): 3302, 3089, 2106, 1735, 1663, 1630, 1543, 1512, 1451, 1434, 1386, 1375, 1214, 1107, 703 cm$^{-1}$.

Optical rotation: $[\alpha]^{20}_D$ –43.2° (c 0.118, CHCl$_3$).

ESI MS: 543 ([M+H]$^+$).

HR ESI MS: calcd for C$_{27}$H$_{39}$O$_6$N$_6$ 543.29256; found 543.29255.

Example 16 Isopropyl 2-(6-acetamido-2-(2-acetyl-1,2,3,4-tetrahydroisoquinoline-3-carboxamido)hexanamido)-6-diazo-5-oxohexanoate (Compound 16)

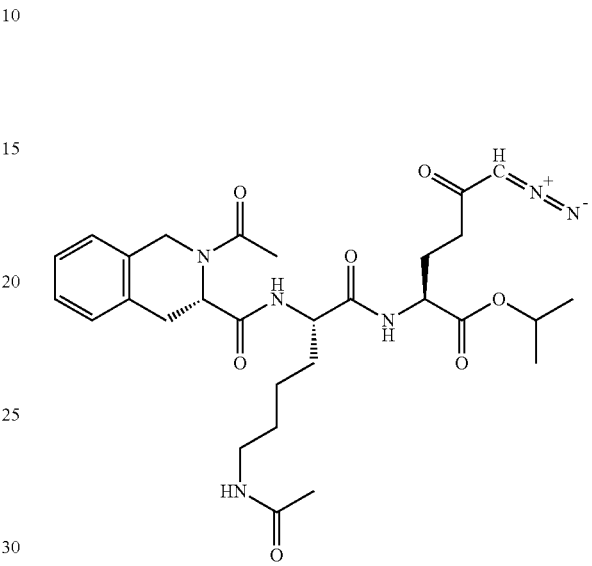

Starting material 15 (150 mg, 0.276 mmol, 1 equiv.) was dissolved in anhydrous DMF (5 mL) and pyridine (44 mg, 45 µL, 0.553 mmol, 2 equiv.) followed by acetic anhydride (34 mg, 31 µL, 0.332 mmol, 1.2 equiv.) were added. Resulting mixture was stirred for 3 h at rt under an inert atmosphere. DMF was evaporated and the residue was purified by LC (CHCl$_3$/MeOH 15:1) to obtain compound 16 (135 mg, 83%) as a light yellow solid (mixture of isomers ~ 5:1).

$^1$H NMR (400 MHZ, CDCl$_3$, major isomer): 1.23 (3H, d, J=6.3), 1.24 (3H, d, J=6.3), 1.28-1.54 (3H, m), 1.64-1.75 (1H, m), 1.95 (3H, s), 1.95-2.03 (2H, m), 2.09-2.18 (2H, m), 2.28 (3H, s), 2.32-2.44 (2H, m), 3.07 (1H, dd, J=9.3, 6.2), 3.12 (2H, q, J=6.2), 3.30 (1H, dd, J=15.4, 4.9), 4.30 (1H, td, J=8.0, 4.6), 4.39 (1H, ddd, J=9.1, 7.7, 4.3), 4.53-4.70 (2H, m), 4.96 (1H, dd, J=5.2, 4.0), 5.00 (1H, hept, J=6.3), 5.38 (1H, bs), 6.23 (1H, t, J=5.7), 6.67 (1H, d, J=7.8), 7.09 (1H, d, J=7.7), 7.13-7.25 (4H, m).

$^{13}$C NMR (101 MHZ, CDCl$_3$, major isomer): 21.75, 21.83, 21.84, 22.51, 23.34, 26.70, 28.60, 31.43, 32.95, 36.71, 38.79, 47.42, 52.33, 52.60, 54.89, 58.00, 69.48, 125.97, 127.17, 128.17, 128.19, 133.10, 134.06, 170.52, 171.03, 171.25, 171.44, 171.67, 194.44.

IR (CHCl$_3$): 3449, 3413, 3337, 3116, 3073, 2109, 1731, 1661, 1636, 1514, 1460, 1437, 1385, 1377, 1365, 1321, 1262, 1235, 1118, 1105, 968, 823 cm$^{-1}$.

Optical rotation: $[\alpha]^{20}_D$ –5.8° (c 0.188, CHCl$_3$).

ESI MS: 607 ([M+Na]$^+$).

HR ESI MS: calcd for C$_{29}$H$_{40}$O$_7$N$_6$Na 607.28507; found 607.28511.

Example 17 Isopropyl 2-(6-acetamido-2-(2-amino-3-methylbutanamido)-hexanamido)-6-diazo-5-oxohexanoate (Compound 17)

Example 18 Isopropyl 2-(6-acetamido-2-(2-acetamido-3-methylbutanamido)-hexanamido)-6-diazo-5-oxohexanoate (Compound 18)

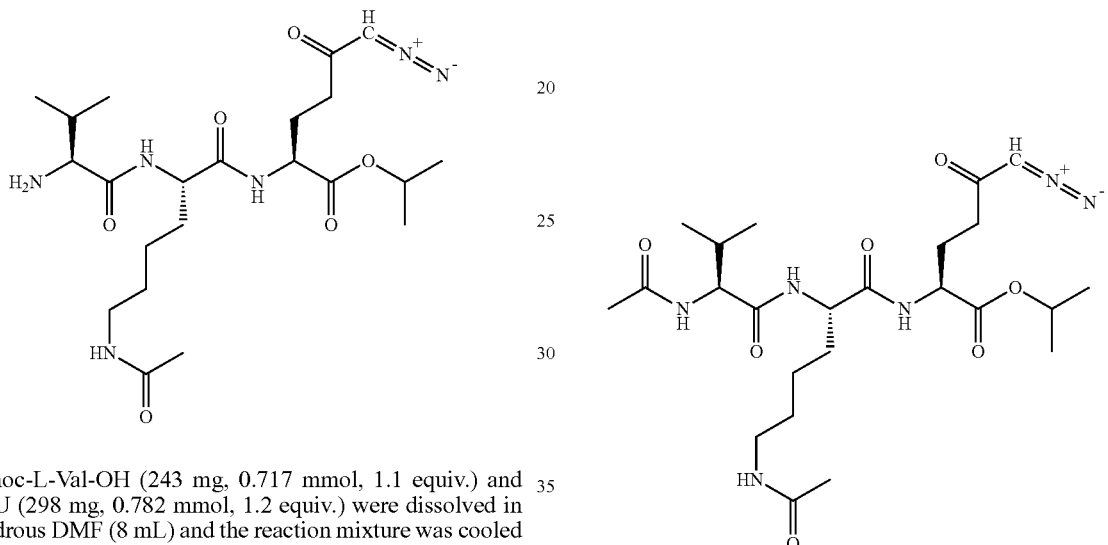

Fmoc-L-Val-OH (243 mg, 0.717 mmol, 1.1 equiv.) and HATU (298 mg, 0.782 mmol, 1.2 equiv.) were dissolved in anhydrous DMF (8 mL) and the reaction mixture was cooled to 0° C. DIEA (253 mg, 341 µL, 1.96 mmol, 3 eqiv.) was added and reaction mixture was stirred for 15 min at the same temperature. Finally the solution of 3 (250 mg, 0.652 mmol, 1 equiv.) in anhydrous DMF (4 mL) was added dropwise. The mixture was stirred at 0° C. for further 30 min and at rt for 3 h. Diethylamine (477 mg, 674 µL, 6.52 mmol, 10 eqiv.) was added to the mixture to remove Fmoc protecting group and the solution was stirred overnight at rt under an inert atmosphere. DMF was evaporated and the crude product was purified by LC (CHCl$_3$/MeOH 5:1). The desired product 17 (173 mg, 55% yield) was obtained as a light yellow solid.

$^1$H NMR (400 MHZ, CDCl$_3$): 0.83 (3H, d, J=6.9), 0.99 (3H, d, J=6.9), 1.24 (3H, d, J=6.3), 1.26 (3H, d, J=6.3), 1.35-1.45 (2H, m), 1.48-1.62 (4H, m), 1.65-1.75 (1H, m), 1.82-1.93 (1H, m), 1.96 (3H, s), 1.96-2.05 (1H, m), 2.13-2.23 (1H, m), 2.24-2.32 (1H, m), 2.33-2.49 (2H, m), 3.16-3.30 (2H, m), 3.27 (1H, d, J=3.8), 4.39-4.47 (2H, m), 5.02 (1H, hept, J=6.3), 5.34 (1H, bs), 6.01 (1H, bs), 7.23 (1H, d, J=7.0), 7.87 (1H, d, J=8.0).

$^{13}$C NMR (101 MHz, CDCl$_3$): 16.27, 19.84, 21.86, 21.88, 22.49, 23.35, 26.62, 28.75, 31.03, 31.98, 36.55, 39.00, 52.40, 52.52, 55.24, 60.28, 69.55, 170.43, 171.23, 171.92, 174.94, 194.23.

IR (CHCl$_3$): 3412, 3339, 3277, 2982, 2872, 2110, 1731, 1662, 1639, 1515, 1466, 1376, 1349, 1182, 1146, 1105, 1042 cm$^{-1}$.

Optical rotation: $[\alpha]^{20}{}_D$ –7.3° (c 0.041, CHCl$_3$).

ESI MS: 505 ([M+Na]$^+$).

HR ESI MS: calcd for C$_{22}$H$_{38}$O$_6$N$_6$Na 505.27450; found 505.27454.

Starting material 17 (150 mg, 0.310 mmol, 1 equiv.) was dissolved in anhydrous DMF (5 mL) and pyridine (49 mg, 50 µL, 0.622 mmol, 2 equiv.) followed by acetic anhydride (38 mg, 35 µL, 0.373 mmol, 1.2 equiv.) were added. Resulting mixture was stirred for 2 h at rt under an inert atmosphere. DMF was evaporated and the residue was purified by LC (CHCl$_3$/MeOH 10:1) to obtain compound 18 (120 mg, 74%) as a light yellow solid.

$^1$H NMR (400 MHZ, d$_4$-MeOD): 0.97 (3H, d, J=6.9), 0.98 (3H, d, J=6.9), 1.26 (3H, d, J=6.3), 1.27 (3H, d, J=6.3), 1.31-1.37 (1H, m), 1.39-1.59 (4H, m), 1.63-1.76 (1H, m), 1.77-1.90 (1H, m), 1.94 (3H, s), 2.02 (3H, s), 2.02-2.11 (1H, m), 2.13-2.25 (1H, m), 2.39-2.55 (2H, m), 3.10-3.26 (2H, m), 4.17 (1H, d, J=7.3), 4.32 (1H, dd, J=8.6, 5.7), 4.37 (1H, dd, J=9.5, 4.7), 5.01 (1H, hept, J=6.3), 5.83 (1H, bs).

$^{13}$C NMR (101 MHz, d$_4$-MeOD): 18.78, 19.77, 21.99 (2C), 22.43, 22.59, 24.10, 27.66, 29.91, 31.77, 32.61, 37.27, 40.17, 53.15, 54.57, 56.22, 60.41, 70.34, 172.45, 173.21, 173.41, 173.85, 174.23, 196.91.

IR (CHCl$_3$): 3426, 3277, 2960, 2875, 2110, 1721, 1660, 1628, 1537, 1465, 1386, 1376, 1348, 1181, 1147, 1106, 1042 cm$^{-1}$.

Optical rotation: $[\alpha]^{20}{}_D$ –38.6° (c 0.189, DMF).

ESI MS: 547 ([M+Na]$^+$).

HR ESI MS: calcd for C$_{24}$H$_{40}$O$_7$N$_6$Na 547.28507; found 547.28516.

Example 19 Isopropyl 2-(6-acetamido-2-(2-amino-3-(4-hydroxyphenyl)-propanamido)hexanamido)-6-diazo-5-oxohexanoate (Compound 19)

Example 20 Isopropyl 2-(6-acetamido-2-(2-acetamido-3-(4-hydroxyphenyl)-propanamido)hexanamido)-6-diazo-5-oxohexanoate (Compound 20)

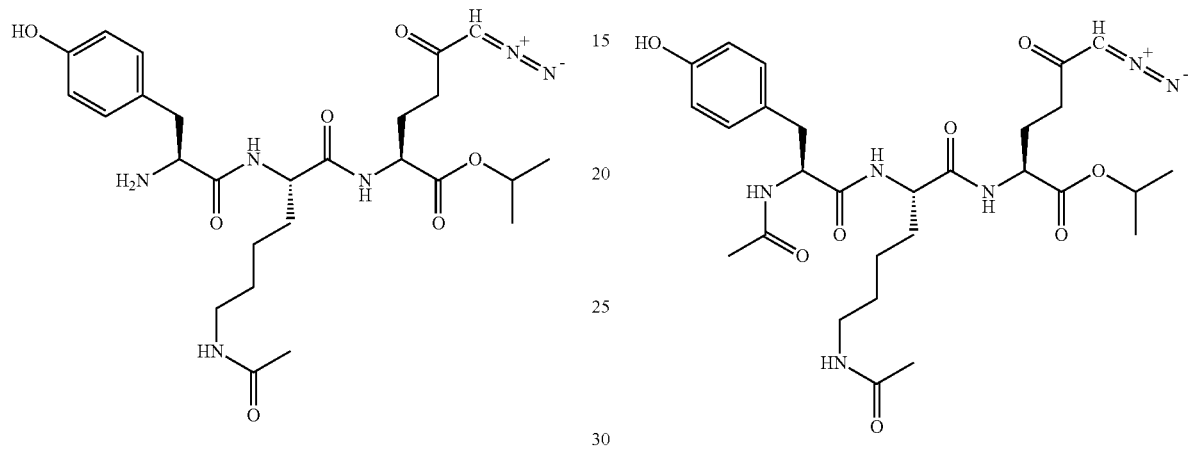

Fmoc-L-Tyr-OH (289 mg, 0.717 mmol, 1.1 equiv.) and HATU (298 mg, 0.782 mmol, 1.2 equiv.) were dissolved in anhydrous DMF (8 mL) and the reaction mixture was cooled to 0° C. DIEA (253 mg, 341 μL, 1.96 mmol, 3 eqiv.) was added and reaction mixture was stirred for 15 min at the same temperature. Finally the solution of 3 (250 mg, 0.652 mmol, 1 equiv.) in anhydrous DMF (4 mL) was added dropwise. The mixture was stirred at 0° C. for further 30 min and at rt for 3 h. Diethylamine (477 mg, 674 μL, 6.52 mmol, 10 eqiv.) was added to the mixture to remove Fmoc protecting group and the solution was stirred overnight at rt under an inert atmosphere. DMF was evaporated and the crude product was purified by LC ($CHCl_3$/MeOH 6:1). The desired product 19 (118 mg, 33% yield) was obtained as a light yellow solid.

$^1$H NMR (400 MHZ, $d_4$-MeOD): 1.26 (3H, d, J=6.3), 1.27 (3H, d, J=6.3), 1.28-1.33 (1H, m), 1.33-1.58 (4H, m), 1.60-1.73 (1H, m), 1.74-1.86 (1H, m), 1.95 (3H, s), 2.14-2.25 (1H, m), 2.41-2.52 (2H, m), 2.76 (1H, dd, J=13.7, 7.4), 2.97 (1H, dd, J=13.8, 5.2), 3.17 (2H, t, J=6.9), 3.60 (1H, t. J=6.3), 4.29-4.40 (2H, m), 5.02 (1H, hept, J=6.3), 5.82 (1H, bs), 6.74 (2H, d, J=8.2), 7.06 (2H, d, J=8.2).

$^{13}$C NMR (101 MHz, $d_4$-MeOD): 21.99 (2C), 22.61, 23.94, 27.51, 29.98, 32.94, 37.27, 40.17, 41.12, 53.25, 53.34, 54.29, 57.33, 70.33, 116.32 (2C), 129.05, 131.51 (2C), 157.33, 172.40, 173.16, 174.15, 176.51, 196.89.

IR (KBr): 3290, 3082, 2984, 2953, 2926, 2856, 2107, 1730, 1651, 1638, 1614, 1594, 1543, 1516, 1466, 1384, 1375, 1349, 1292, 1267, 1227, 1173, 1145, 1106, 1029, 826, 690, 645, 404 $cm^{-1}$.

Optical rotation: $[\alpha]^{20}_D$ −18.6° (c 0.167, MeOH).

ESI MS: 569 ([M+Na]$^+$).

HR ESI MS: calcd for $C_{26}H_{38}O_7N_6Na$ 569.26942; found 569.26948.

Starting material 19 (150 mg, 0.274 mmol, 1 equiv.) was dissolved in anhydrous DMF (5 mL) and pyridine (43 mg, 44 μL, 0.549 mmol, 2 equiv.) followed by acetic anhydride (34 mg, 31 μL, 0.329 mmol, 1.2 equiv.) were added. Resulting mixture was stirred for 2.5 h at rt under an inert atmosphere. DMF was evaporated and the residue was purified by LC ($CHCl_3$/MeOH 10:1) to obtain compound 20 (91 mg, 56%) as a light yellow solid.

$^1$H NMR (400 MHZ, $d_4$-MeOD): 1.26 (3H, d, J=6.3), 1.27 (3H, d, J=6.3), 1.29-1.33 (1H, m), 1.34-1.57 (4H, m), 1.62-1.74 (1H, m), 1.76-1.87 (1H, m), 1.92 (3H, s), 1.94 (3H, s), 2.14-2.24 (1H, m), 2.38-2.52 (2H, m), 2.79 (1H, dd, J=14.0, 9.0), 3.04 (1H, dd, J=14.1, 5.5), 3.17 (2H, td, J=6.9, 2.0), 4.35 (1H, dd, J=9.5, 4.9), 4.29 (1H, dd, J=8.5, 5.6), 4.56 (1H, dd, J=9.0, 5.5), 5.01 (1H, hept, J=6.3), 5.81 (1H, bs), 6.70 (2H, d, J=8.5), 7.07 (2H, d, J=8.5).

$^{13}$C NMR (101 MHZ, $d_4$-MeOD): 21.99 (2C), 22.41, 22.60, 24.04, 27.56, 29.94, 32.68, 37.32, 37.94, 40.20, 50.23, 53.23, 54.55, 56.41, 56.46, 70.37, 116.20 (2C), 129.02, 131.25 (2C), 157.29, 172.44, 173.25, 173.86, 174.09, 196.95.

IR (KBr): 3380, 3284, 3078, 3019, 2978, 2929, 2858, 2108, 1722, 1655, 1635, 1613, 1593, 1543, 1517, 1466, 1449, 1385, 1375, 1350, 1293, 1272, 1234, 1174, 1145, 1106, 1040, 825, 697, 645, 547, 406 $cm^{-1}$.

Optical rotation: $[\alpha]^{20}_D$ −4.0° (c 0.273, MeOH).

ESI MS: 611 ([M+Na]$^+$).

HR ESI MS: calcd for $C_{28}H_{40}O_8N_6Na$ 611.27998; found 611.28000.

Example 21 Isopropyl 2-(2-(3-(1H-indol-3-yl)-2-pivalamidopropanamido)-6-acetamidohexanamido)-6-diazo-5-oxohexanoate (Compound 21)

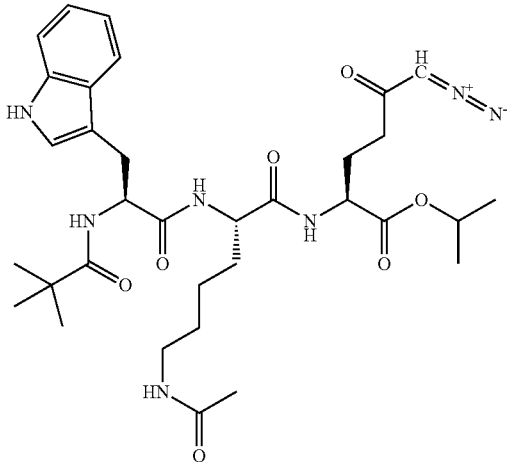 [SMILES: CC(=O)NCCCC[C@H](NC(=O)[C@H](Cc1c[nH]c2ccccc12)NC(=O)C(C)(C)C)C(=O)N[C@@H](CCC(=O)C=[N+]=[N-])C(=O)OC(C)C]

Compound 11 (150 mg, 0.263 mmol) was dissolved in anhydrous DMF (6 mL) and DIEA (68 mg, 92 µL, 0.527 mmol, 2 equiv.) followed by trimethylacetyl chloride (41 mg, 42 L, 0.342 mmol, 1.3 equiv) were added. The resulting mixture was stirred at rt under an inert atmosphere for 5 h. DMF was evaporated and the crude product was purified by LC (CHCl$_3$/MeOH 10:1) to afford 83 mg (48%) of yellowish solid compound 21.

$^1$H NMR (400 MHZ, CDCl$_3$): 1.13 (9H, s), 1.24 (3H, d, J=6.3), 1.26 (3H, d, J=6.3), 1.21-1.30 (2H, m), 1.35-1.50 (2H, m), 1.51-1.62 (1H, m), 1.74-1.85 (1H, m), 1.93-2.04 (1H, m), 2.00 (3H, s), 2.11-2.21 (1H, m), 2.27-2.44 (2H, m), 3.08 (1H, dt, J=13.7, 6.8), 3.21 (1H, dd, J=14.6, 4.8), 3.29 (1H, dt, J=13.7, 6.8), 3.42 (1H, dd, J=14.6, 4.8), 4.25-4.44 (2H, m), 4.73 (1H, td, J=7.1, 4.8), 5.02 (1H, hept, J=6.3), 5.35 (1H, bs), 6.01 (1H, t, J=5.9), 6.41 (1H, d, J=7.3), 6.44 (1H, d, J=7.3), 6.90 (1H, d, J=7.6), 7.09 (1H, d, J=2.4), 7.13 (1H, ddd, J=8.0, 7.1, 1.1), 7.19 (1H, ddd, J=8.2, 7.0, 1.2), 7.41 (1H, d, J=8.0), 7.69 (1H, d, J=7.8), 9.44 (1H, bs).

$^{13}$C NMR (101 MHZ, CDCl$_3$): 21.82 (2C), 21.95, 23.33, 26.98, 27.48 (3C), 29.20, 29.79, 31.64, 36.53, 39.17, 52.14, 53.07, 54.42, 55.32, 69.48, 109.50, 111.84, 118.39, 119.57, 122.09, 123.73, 127.57, 136.49, 170.91, 171.15, 171.34, 171.72, 179.05, 194.43.

IR (CHCl$_3$): 3477, 3447, 3418, 3326, 3117, 3084, 3062, 2967, 2110, 1731, 1660, 1620, 1603, 1548, 1524, 1504, 1495, 1458, 1419, 1398, 1385, 1376, 1368, 1321, 1262, 1236, 1105, 1069, 1011 cm$^{-1}$.

Optical rotation: $[\alpha]^{20}_D$ –18.3° (c 0.104, CHCl$_3$).

ESI MS: 676 ([M+Na]$^+$).

HR ESI MS: calcd for C$_{33}$H$_{47}$O$_7$N$_7$Na 676.34292; found 676.34300.

Example 22 Biological Testing

Materials and Methods

1. Metabolic Stability in Intestinal and Liver Homogenates:

Compounds 1-21 were evaluated ex vivo in swine tissue homogenates for stability and release of DON. Briefly, the tissues (e.g. Liver or intestine; approx. 10 mg) were weighed and added as a 10% w/v with 0.1M potassium phosphate buffer, pH=7.4. The suspended tissue was homogenized while submerged in an ice bath using a tissue sonic dismembrator, with alternating periods of 10 seconds on and off until contents are present as a milky solution. For conductance of experiments, compounds were spiked into solution to a final concentration of 20 µM. At predetermined time points, 100 uL aliquots of the spiked solution were removed into to marked tubes with 300 uL of cold MeOH containing 0.5 uM of internal standard and analyzed for percent compound remaining and DON release via LC/MS/MS (see, Rais et al., 2016; Nedelcovych et al., 2017).

FIG. 1A is a bar graph showing the stability of intact compounds 1-21 after incubation for 60 minutes in the presence of pig intestinal homogenate. FIG. 1B is a bar graph showing the extent of DON release when compounds 1-21 are incubated for 60 minutes in the presence of pig intestinal homogenate.

FIG. 2A is a bar graph showing the stability of intact compounds 1-21 after incubation for 60 minutes in the presence of pig liver homogenate. FIG. 2B is a bar graph showing the extent of DON release when compounds 1-21 are incubated for 60 minutes in the presence of pig liver homogenate. The figures show that most of the compounds remain substantially intact in the presence of the liver homogenate.

2. Human Tumor Cell Versus Plasma Partitioning:

To evaluate the partitioning of compounds into P493 lymphoma tumor cells versus plasma, the compounds were spiked in human plasma containing 10 million P493 cells and incubated at 37° C. for 60 min. The cell plasma mix was centrifuged at 10,000 g for 10 min and parent compound and DON in cells and plasma was then quantified using LC/MS/MS methods (see, Rais et al., 2016; Nedelcovych et al., 2017).

FIG. 3A is a bar graph showing concentrations of DON in P493 tumor cells after compounds 1-21 were incubated in human plasma containing P493 tumor cells. FIG. 3B is a bar graph showing concentrations of DON in plasma after compounds 1-21 were incubated in human plasma containing P493 tumor cells. The figures show that the compounds preferentially partitioned in the P493B cells compared to plasma.

3. Head to Head Single Time-Point Comparison of Compounds 1, 7, 12 and 16 and DON in Tumor Cell-to-Plasma Partition:

Compounds 1, 7, 12 and 16 were evaluated for their ability to be taken up in tumor cells and cleaved to give DON. The experimental conditions are described below.

a. Human Tumor Cell to Plasma Partitioning Assay

Tumor cell to plasma partitioning assay was conducted in P493B lymphoma cells (obtained from Dr. Chi Dang, Abramson Cancer Center, University of Pennsylvania, Philadelphia, PA; (REF, Nature 458, 762-765, 2009). In brief, cells were grown in 150 cm$^2$ cell T-flasks (Falcon™, USA) with RPMI 1640, 1× L-glutamine medium (Corning™ Cellgro™, USA) supplemented with 10% (v/v) FBS (Gibco™, USA), and 1% streptomycin and gentamycin (Gibco™, USA). All cells were incubated at 37° C., in a humidified atmosphere with 5% CO$_2$. The cell confluency was monitored visually using an Axiovert 25 optical microscope equipped with an 3CCD digital camera. Upon confluency, cell suspension was collected and centrifuged at 1000 rpm for 5 min at 25° C. to collect the cell pellet. The supernatant media was decanted, the cell pellet was re-suspended in 20 mL of DPBS (Gibco™, USA), and maintained at 37° C. in order to remove the media traces.

The cell count was determined using an automated cell counter (Bio-Rad, USA) following a 1:1 dilution of an aliquot with 0.4% trypan blue solution (Bio-Rad, USA). The cell suspension in DPBS was centrifuged at 1000 rpm for 5 min at 25° C. to collect the cell pellet. The supernatant DPBS was decanted and the cell pellets were resuspended in human plasma (Innovative Research, USA) to obtain a cell density of 10 million cells/mL of plasma. For analysis of cell partitioning cell-plasma suspension, 1 ml, was pre-incubated at 37° C. for 5 min, following which, compounds were spiked for a final concentration of 20 µM and re-incubated at 37° C. for 1 h. Following incubation, the cell suspension was centrifuged at 10000 rpm for 10 min at 4° C. Supernatant plasma obtained after centrifugation was collected and stored at −80° C. for intact compound and DON analysis. The cell pellet was washed once with ice cold DPBS, followed by centrifugation and stored at −80° C. for intact prodrug and/or DON analysis by LC-MS/MS.

b. Sample Preparation for DON and Intact Compound Bioanalysis in Cell Pellet

For quantification of DON and intact compound, cell pellets were weighed and suspended in 50 µL of water. To the cell suspension, ice cold methanol with internal standards (losartan: 0.5 µM and glutamate D5: 10 µM) were added in a 5:1 ratio of solvent to cell suspension. The cell samples were vortexed, mixed for 30 sec and centrifuged at 10,000 rpm for 10 min at 4° C. For intact compound bioanalysis, 50 µL of the supernatant obtained after centrifugation was diluted with 50 µL water and transferred to a 250 µL polypropylene vial sealed with a Teflon cap. DON bioanalysis was performed following dabsyl chloride derivatization method with minor modifications (see, Rais et al., 2016; Nedelcovych et al., 2017). Briefly, 200 µL of the supernatant was collected in a separate tube and dried at 45° C. under vacuum for 1 h. To each tube, 50 µL of 0.2 M sodium bicarbonate buffer (pH 9.0) and 100 µL dabsyl chloride stock was added. After vortex mixing, samples were incubated at 60° C. for 15 min to derivatize, followed by centrifuging at 15000 rpm for 5 min. One hundred microliter of the supernatant was transferred to a 96-well plate, diluted with 400 µL of water, and injected on the LC-MS/MS for analysis (see, Nedelcovych et al., 2017). The standard curve for DON quantification in the cell pellet was prepared using naïve P493B cells diluted with water to the equivalent ratio as that of sample.

c. Bioanalysis of DON

Briefly, DON was analyzed on a Dionex ultra high-performance system consisting of an analytical pump, and an autosampler coupled with Q Exactive Focus orbitrap mass spectrometer (Thermo Fisher Scientific Inc., Waltham MA). Separation of the analyte from potentially interfering material was achieved at 35° C. using Agilent Eclipse Plus column (100×2.1 mm i.d.) packed with a 1.8 µm $C_{18}$ stationary phase. The mobile phase used was composed of 0.1% formic acid in water and 0.1% formic acid in acetonitrile with gradient elution, starting with 40% organic linearly increasing to 95% at 1.5 min, maintaining at 95% (1.5-2.5 min), re-equilibrating to 40% at 2.5 min and maintaining 40% organic until the end of the run. The total run time was 3.5 min. The mass spectrometer was operated with a HESI ion source in positive ionization mode for the derivatized DON analyte (Dabsyl-DON) and controlled by the Xcalibur software 4.0.27.13 (Thermo Scientific). Samples were introduced to the source through heated ion spray with the capillary temperature setting at 350° C. Quantification was performed in product-reaction monitoring (PRM) mode. Chromatographic peaks for analyte transitions were integrated and quantified to calculate the concentration of each peak based on the calibration curve. Calibration curves for DON quantification in tumor cells and plasma were constructed over the range 0.005-50 nmol/g or nmol/mL and computed using the ratio of the peak area of analyte to the internal standard by using a linear regression with 1/(nominal concentration) weighting. The parameters of each calibration curve were used to back-calculate concentrations and to obtain values for the QC samples and unknown samples by interpolation.

d. Bioanalysis of Compounds

Compounds were analyzed on a Thermo Scientific Accela UPLC system coupled to Accela open autosampler at ambient temperature with an Agilent Eclipse Plus column (100×2.1 mm i.d.) packed with a 1.8 µm C18 stationary phase. The autosampler was temperature controlled and operated at 10° C. The mobile phase used for the chromatographic separation was composed of acetonitrile/water containing 0.1% formic acid and with a flow rate of 0.4 mL/min for 5 min using gradient elution. The column effluent was monitored using TSQ Vantage triple-quadrupole mass-spectrometric detector, equipped with an electrospray probe set in the positive ionization mode. Samples were introduced into the ionization source through a heated nebulized probe (350° C.). Disappearance of compounds was measured from ratio of peak areas of analyte to internal standard. Calibration curves over the range 0.001-50 nmol/g [compound 7] in naïve human plasma were constructed from the peak area ratio of the analyte to the internal standard using linear regression with a weighing factor of 1/(nominal concentration). Correlation coefficient of greater than 0.99 was considered to be acceptable in the analytical runs for all analytes.

e. Results and Analysis

FIGS. 5A-C shows tumor cell to plasma partitioning of DON and compounds 1, 7, 12, and 16. With the exception of compound 16 all compounds showed partitioning into and bioactivation to DON inside the lymphoma cells with concentrations similar to DON (FIG. 5A). Notably all four compounds were stable in human plasma causing minimal DON release (FIG. 5B). When directly compared to DON, it is surprising to find that the DON tumor cell-to-plasma partitioning ratio from 1, 7, 12 and 16 was improved 13-, 27-, 12-, and 46-fold, respectively (FIG. 5C). Although compound 16 afforded the best tumor cell/plasma partitioning ratio, compound 7 delivered enhanced DON tumor levels compared to 16 (8.81±0.02 µM versus 0.12±0.04 µM). As showed above, the tested compounds demonstrated unexpected preference in delivering DON to human tumor cells versus plasma. In addition, compound 7 both achieved unexpected improvement in DON tumor cell-to-plasma partitioning ratio (27 fold) and enhanced delivery of DON to tumor cells. Thus compound 7 was selected for further evaluation in a time course experiment.

4. Time Dependent Tumor Cell to Plasma Partitioning of Compound 7

Compound 7 showed the best tumor cell to plasma partitioning in the initial single time-point screening and was further evaluated in a time-course tumor to cell partitioning study following a similar protocol as that followed for the initial single time-point screening except the samples were incubated for 0.25, 0.5, 1 and 2 h time-points to obtain a time-dependent partitioning profile.

Figure 6A:
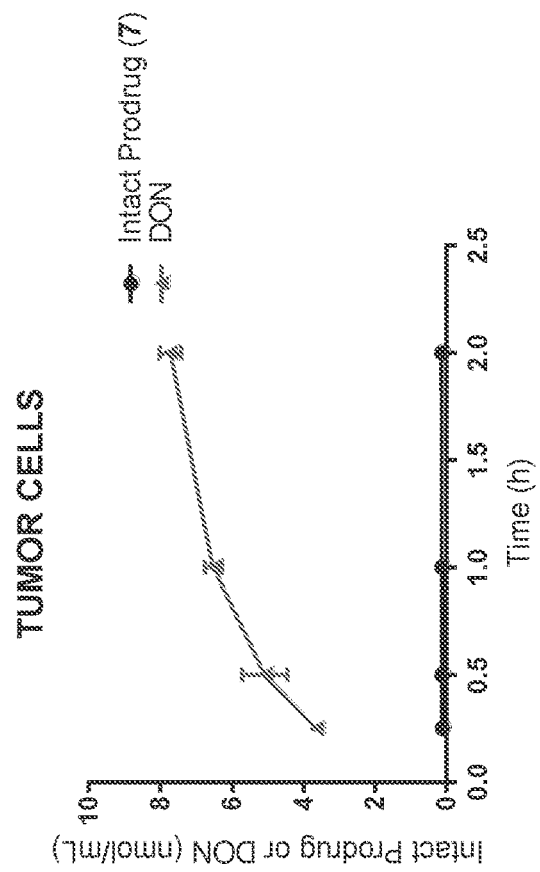
Figure 6B:
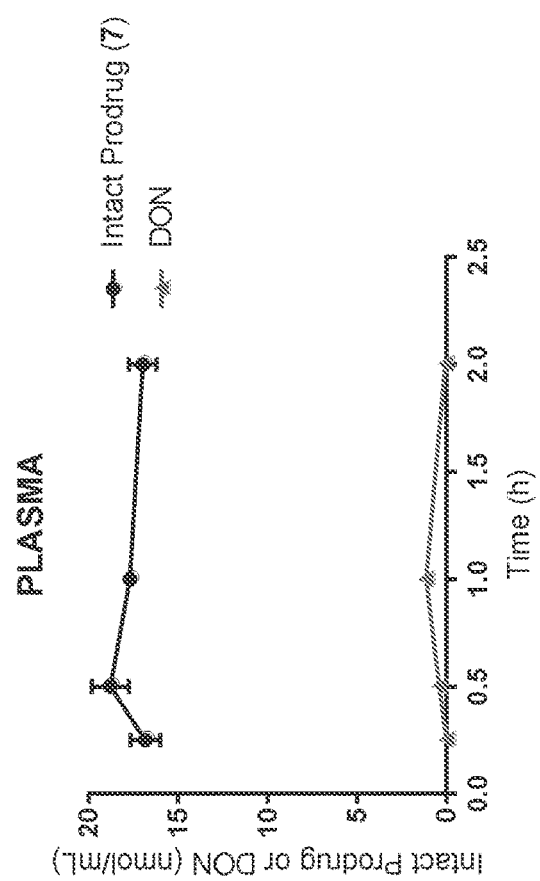
Figure 7:
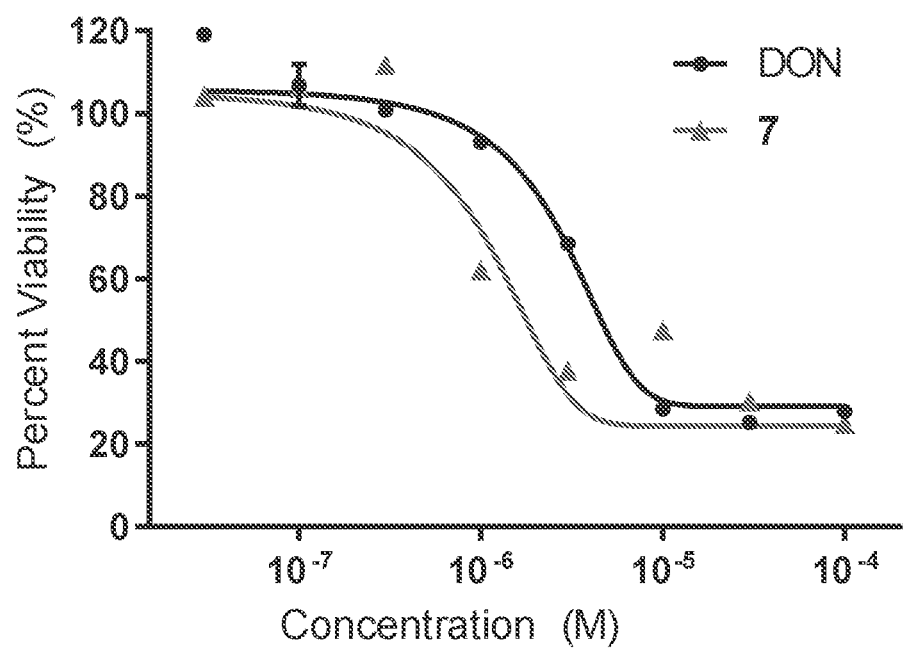

FIG. 6A demonstrated that in swine and human plasma compound 7 showed stability and mostly present as intact compound with <5% DON release suggesting minimal metabolism and conversion to DON in plasma. In contrast, in P493B tumor cells, a time dependent increase in DON release over time was observed (>40% of initial concentrations)(FIG. 6B). <1% intact compound was observed in tumor cells suggesting selective release in tumor cells versus plasma.

5. Dog Pharmacokinetic Study:

The dog pharmacokinetic study was conducted in accordance with the guidelines recommended in Guide for the Care and Use of Laboratory Animals and was approved by the Absorption Systems (San Diego, CA) Institutional Animal Care and Use Committee. Compound #2 was administered to male beagle dogs (n=1/group) as a bolus subcutaneous dose or infused over 1 h at a dose of 0.2 mg/kg DON equivalent. Blood samples were collected from the jugular vein (~1 mL) via direct venipuncture at 0 min, 5 min (IV only), 15 min, 1 h, 2 h, 4 h, 8 h, and 24 h, post dose, placed into sodium heparin tubes, and maintained on wet ice until processing. Blood samples were centrifuged at a temperature of 4° C., at 3000× g, for 5 minutes. Plasma was collected in tubes and flash frozen. Samples were stored in a freezer set to maintain −60° C. to −80° C. until bioanalysis as described previously (see, Rais et al., 2016; Nedelcovych et al., 2017).

FIG. 4A is a graph showing the concentrations of DON and compound 2 over time after intravenous (IV) infusion. FIG. 4B is a graph showing the concentrations of DON and compound 2 over time after subcutaneous (SC) infusion. The pharmacokinetic data was as follows:

DON Pharmacokinetic Parameters Following #2 Administration

| Parameter | Units | IV INFUSION | SC |
|---|---|---|---|
| $T_{max}$ | h | 1 | 8 |
| $C_{max}$ | pmol/ml | 1494 | 864 |
| $AUC_{0-t}$ | h*pmol/ml | 11503 | 11312 |

Intact Compound Pharmacokinetic Parameters Following #2 Administration

| Parameter | Units | IV INFUSION | SC |
|---|---|---|---|
| $T_{max}$ | h | .08 | 4 |
| $C_{max}$ | pmol/ml | 6572 | 470 |
| $AUC_{0-t}$ | h*pmol/ml | 7454 | 2599 |

The data shows that IV and SC administration give very similar AUC of DON. Also, the $C_{max}$ for SC administration was nearly half that for IV infusion. The $T_{max}$ was much longer for SC administration, showing a slow, steady absorption and conversion to DON.

6. Compound 7 Dog Pharmacokinetic Study

Compound 7 was administrated to a beagle dog subcutaneously. FIG. 4C is a line graph showing its plasma pharmacokinetics in the dog. The data was summarized in the following table:

| Cpd | Species/ Ns per cohort | Actual Dose (mg/kg) | DON eq. Dose (mg/kg) | Cmax Cpd 7 (nmol/ml) | AUC Cpd 7 (nmol · h/ml) | Cmax DON (nmol/ml) | AUC DON (nmol · h/ml) |
|---|---|---|---|---|---|---|---|
| 7 | (N = 1) | 2.6 | 0.8 | 0.64 | 2.1 | 0.89 | 8.9 |

7. DON and Compound 7 in Cell Proliferation Assay Using P493 B Lymphoma Cells a. Proliferation Assay The cell proliferation assay was performed using the CellTiter 96® AQueous one solution cell proliferation reagent following the manufacturers' instruction (Promega, USA). Briefly, P493B lymphoma cells were plated in 96 well plates at a density of 20,000 cells/well in a final volume of 100 μL growth media. Test compound stocks were made in DMSO and were added to cells in a 1:10 serial dilution with a final concentration of 0.2% DMSO. Cells were allowed to proliferate for 72 h in the presence of test compounds. Thereafter, 20 μL of CellTiter 96™ AQeous (Promega #3580) was added per well and incubated for 2 h. Absorbance was measured at 490 nM. Live cells showed increased absorbance due to the conversion of a tetrazolium compound into a formazan product by the mitochondria of live cells.

b. Results

DON and compound 7 were incubated with P493B lymphoma cells for 72 h, and cell viability was measured. Both compounds caused a concentration dependent decrease in cell viability. Non-linear regression analysis of the log transformed data gave the $EC_{50}$ values for DON at 10.0±0.11 μM while compound 7 unexpectedly gave a two-fold improvement of tumor cell killing with an $EC_{50}$ value of 5.0±0.12 μM.

Overall, the experiments shown above demonstrated unexpectantly that the compounds disclosed herein deliver the glutamine antagonist DON preferentially to human tumor cells versus plasma, with significantly less glutamine antagonist exposure in liver (enriched in metabolic enzymes) and gut (the presumed toxicity organ). This characteristic enhances the DONS' therapeutic safety window.

REFERENCES

All publications, patent applications, patents, and other references mentioned in the specification are indicative of the level of those skilled in the art to which the presently disclosed subject matter pertains. All publications, patent applications, patents, and other references (e.g., websites, databases, etc.) mentioned in the specification are herein incorporated by reference in their entirety to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

Ahluwalia, G. S.; Grem, J. L.; Hao, Z.; Cooney, D. A. Metabolism and action of amino acid analog anti-cancer agents. *Pharmacol Ther* 1990, 46, 243-271.

Alt, J.; Potter, M. C.; Rojas, C.; Slusher, B. S. Bioanalysis of 6-diazo-5-oxo-1-norleucine in plasma and brain by ultra-performance liquid chromatography mass spectrometry. *Anal Biochem* 2015, 474, 28-34.

Barclay, R. K.; Phillipps, M. A. Effects of 6-diazo-5-oxol-norleucine and other tumor inhibitors on the biosynthesis of nicotinamide adenine dinucleotide in mice. *Cancer Res* 1966, 26, 282-286.

Berge et al., "Pharmaceutical Salts," Journal of Pharmaceutical Science, 1977, 66, 1-19

Cervantes-Madrid, D.; Romero, Y.; Duenas-Gonzalez, A. Reviving Lonidamine and 6-Diazo-5-oxo-L-norleucine to Be Used in Combination for Metabolic Cancer Therapy. *Biomed Res Int* 2015, 2015, 690492.

Cinatl et al., "Antiviral effects of 6-diazo-5-oxo-L-norleucine on replication of herpes simplex virus type 1" *Antiviral Research.* 1997; 33:165-175.

Coffey, G. L.; Ehrlich, J.; Fisher, M. W.; Hillegas, A. B.; Kohberger, D. L.; Machamer, H. E.; Rightsel, W. A.; Roegner, F. R. 6-Diazo-5-oxo-L-norleucine, a new tumor-inhibitory substance. I. Biologic studies. *Antibiot Chemother (Northfield)* 1956, 6, 487-497.

Coggin et al., "6-Diazo-5-Oxo-L-Norleucine Inhibition of *Escherichia coli,*" *Journal of Bacteriology.* 1965; 86.

Cui, F.; Wang, W.; Wu, D.; He, X.; Wu, J.; Wang, M. Overexpression of Cathepsin L is associated with gefitinib resistance in non-small cell lung cancer. *Clinical and Translational Oncology* 2016, 18, 722-727.

D'Andrea, S.; Zheng, Z.; Scola, P. Inhibitors of Hepatitis C Virus, U.S. Pat. Appl. 2008/0107624.

DeBerardinis et al., "Q's next: the diverse functions of glutamine in metabolism, cell biology and cancer" *Oncogene.* 2009; 29 (3): 313-324.

Dion, H. W.; Fusari, S. A.; Jakubowski, Z. L.; Zora, J. G.; Bartz, Q. R. 6-Diazo-5-oxo-L-norleucine, A New Tumor-inhibitory Substance. II.1 Isolation and Characterization. *J. Am. Chem. Soc.,* 1956, 78, 3075-3077.

Dranoff, G.; Elion, G. B.; Friedman, H. S.; Bigner, D. D. Combination chemotherapy in vitro exploiting glutamine metabolism of human glioma and medulloblastoma. *Cancer Res* 1985, 45, 4082-4086.

Dranoff, G.; Elion, G. B.; Friedman, H. S.; Campbell, G. L.; Bigner, D. D. Influence of glutamine on the growth of human glioma and medulloblastoma in culture. *Cancer Res* 1985, 45, 4077-4081.

Eagan, R. T.; Frytak, S.; Nichols, W. C.; Creagan, E. T.; Ingle, J. N. Phase II study on DON in patients with previously treated advanced lung cancer. *Cancer Treat Rep* 1982, 66, 1665-1666.

Earhart, R. H.; Amato, D. J.; Chang, A. Y.; Borden, E. C.; Shiraki, M.; Dowd, M. E.; Comis, R. L.; Davis, T. E.; Smith, T. J. Phase II trial of 6-diazo-5-oxo-L-norleucine versus aclacinomycin-A in advanced sarcomas and mesotheliomas. *Invest New Drugs* 1990, 8, 113-119.

Earhart, R. H.; Koeller, J. M.; Davis, H. L. Phase I trial of 6-diazo-5-oxo-L-norleucine (DON) administered by 5-day courses. *Cancer Treat Rep* 1982, 66, 1215-1217.

Erickson, J. W.; Cerione, R. A. Glutaminase: a hot spot for regulation of cancer cell metabolism? *Oncotarget* 2010, 1, 734-740.

Eshleman, J. S.; Carlson, B. L.; Mladek, A. C.; Kastner, B. D.; Shide, K. L.; Sarkaria, J. N. Inhibition of the mammalian target of rapamycin sensitizes U87 xenografts to fractionated radiation therapy. *Cancer Res* 2002, 62, 7291-7297.

Fogal, V.; Babic, I.; Chao, Y.; Pastorino, S.; Mukthavaram, R.; Jiang, P.; Cho, Y. J.; Pingle, S. C.; Crawford, J. R.; Piccioni, D. E.; Kesari, S. Mitochondrial p32 is upregulated in Myc expressing brain cancers and mediates glutamine addiction. *Oncotarget* 2015, 6, 1157-1170.

Gallop, M. A.; Xu, F.; Phan, T.; Dilip, U.; Peng, G. Acyloxyalkyl carbamate prodrugs, methods of synthesis and use, U.S. Pat. Appl. 2008/0146526.

Grayzel, A. I.; Seegmiller, J. E.; Love, E. Suppression of uric acid synthesis in the gouty human by the use of 6-diazo-5-oxo-L-norleucine. *J Clin Invest* 1960, 39, 447-454.

Gross, M. I.; Demo, S. D.; Dennison, J. B.; Chen, L.; Chernov-Rogan, T.; Goyal, B.; Janes, J. R.; Laidig, G. J.; Lewis, E. R.; Li, J.; Mackinnon, A. L.; Parlati, F.; Rodriguez, M. L. M.; Shwonek, P. J.; Sjogren, E. B.; Stanton, T. F.; Wang, T.; Yang, J.; Zhao, F. Y.; Bennett, M. K. Antitumor Activity of the Glutaminase Inhibitor CB-839 in Triple-Negative Breast Cancer. *Mol Cancer Ther* 2014.

Harding, J. J. T., M. L.; Munster, P. N.; Le, M. H.; Molineaux, C.; Bennett, M. K.; Mittra, E.; Burris, H. A.: Clark, A. S.; Dunphy, M.; Meric-Bernstam, F.; Patel, M. R.; DeMichele, A.; Infante, J. R. Safety and tolerability of increasing doses of CB-839, a first-in-class, orally administered small molecule inhibitor of glutaminase, in solid tumors. *J Clin Oncol* 2015.

Henderson, J. M.; Zhang, H. E.; Polak, N.; Gorrell, M. D. Hepatocellular carcinoma: Mouse models and the potential roles of proteases. *Cancer letters* 2017, 387, 106-113.

Hensley, C. T.; Wasti, A. T.; DeBerardinis, R. J. Glutamine and cancer: cell biology, physiology, and clinical opportunities. *J Clin Invest* 2013, 123, 3678-3684.

Hofer, A.; Steverding, D.; Chabes, A.; Brun, R.; Thelander, L. *Trypanosoma brucei* CTP synthetase: a target for the treatment of African sleeping sickness. *Proc Natl Acad Sci USA* 2001, 98, 6412-6416.

Hu, X.; Stern, H. M.; Ge, L.; O'Brien, C.; Haydu, L.; Honchell, C. D.; Haverty, P. M.; Peters, B. A.; Wu, T. D.; Amler, L. C.; Chant, J.; Stokoe, D.; Lackner, M. R.; Cavet, G. Genetic alterations and oncogenic pathways associated with breast cancer subtypes. *Mol Cancer Res* 2009, 7, 511-522.

Hutchinson, J.; Burholt, S.; Hamley, I. Peptide hormones and lipopeptides: from self-assembly to therapeutic applications. *Journal of Peptide Science* 2017, 23, 82-94.

Keicher, J. D.; Roberts, C. D.; Rajwanshi, V. K.; Griffith, R. C.; Zheng, X.; Liehr, S. J. R.; Prhavc, M.; Kim, C. U.; Ray, A. S. Amino tricyclic-nucleoside compounds, compositions, and methods of use, U.S. Pat. Appl. 2009/0062223.

Konopleva, M. Y.; Flinn, I. W.; Wang, E.; DiNardo, C. D.; Bennett, M.; Molineaux, C.; Le, M.; Maris, M.; Frankfurt, O. In *Phase I study: Safety and tolerability of increasing doses of cb-839, an orally-administered small molecule inhibitor of glutaminase, in acute leukemia*, Haematologica, 2015; Ferrata Storti Foundation Via Giuseppe Belli 4, 27100 Pavia, Italy: 2015; pp 378-379.

Kovach, J. S.; Eagan, R. T.; Powis, G.; Rubin, J.; Creagan, E. T.; Moertel, C. G. Phase I and pharmacokinetic studies of DON. *Cancer Treat Rep* 1981, 65, 1031-6.

Le, A.; Lane, A. N.; Hamaker, M.; Bose, S.; Gouw, A.; Barbi, J.; Tsukamoto, T.; Rojas, C. J.; Slusher, B. S.; Zhang, H.; Zimmerman, L. J.; Liebler, D. C.; Slebos, R. J.; Lorkiewicz, P. K.; Higashi, R. M.; Fan, T. W.; Dang, C.

V. Glucose-independent glutamine metabolism via TCA cycling for proliferation and survival in B cells. *Cell Metab* 2012, 15, 110-121.

Lee, Y. Z.; Yang, C. W.; Chang, H. Y.; Hsu, H. Y.; Chen, I. S.; Chang, H. S.; Lee, C. H.; Lee, J. C.; Kumar, C. R.; Qiu, Y. Q.; Chao, Y. S.; Lee, S. J. Discovery of selective inhibitors of Glutaminase-2, which inhibit mTORC1, activate autophagy and inhibit proliferation in cancer cells. *Oncotarget* 2014, 5, 6087-6101.

Liu, W.; Le, A.; Hancock, C.; Lane, A. N.; Dang, C. V.; Fan, T. W.; Phang, J. M. Reprogramming of proline and glutamine metabolism contributes to the proliferative and metabolic responses regulated by oncogenic transcription factor c-MYC. *Proc Natl Acad Sci USA* 2012, 109, 8983-8.

Lynch, G.; Kemeny, N.; Casper, E. Phase II evaluation of DON (6-diazo-5-oxo-L-norleucine) in patients with advanced colorectal carcinoma. *Am J Clin Oncol* 1982, 5, 541-543.Magill, G. B.; Myers, W. P. Alterations in calcium metabolism in cancer patients treated with 6-diazo-5-oxo-L-norleucine. *Proc Soc Exp Biol Med* 1956, 93, 314-318.

MaGill, G. B.; Myers, W. P.; Reilly, H. C.; Putnam, R. C.; Magill, J. W.; Sykes, M. P.; Escher, G. C.; Karnofsky, D. A.; Burchenal, J. H. Pharmacological and initial therapeutic observations on 6-diazo-5-oxo-1-norleucine (DON) in human neoplastic disease. *Cancer* 1957, 10, 1138-1150.

Medina et al., "Relevance of glutamine metabolism to tumor cell growth" *Mol Cell Biochem.* 1992; 113 (1): 1-15.

McDermott, L. A.; Iyer, P.; Vernetti, L.; Rimer, S.; Sun, J.; Boby, M.; Yang, T.; Fioravanti, M.; O'Neill, J.; Wang, L.; Drakes, D.; Katt, W.; Huang, Q.; Cerione, R. Design and evaluation of novel glutaminase inhibitors. *Bioorg Med Chem* 2016, 24, 1819-1839.

Nedelcovych, M. T.; Tenora, L.; Kim, B. H.; Kelschenbach, J.; Chao, W.; Hadas, E.; Jancarik, A.; Prchalova, F.; Zimmermann, S. C.; Dash, R. P.; Gadiano, A. J.; Garrett, C.; Furtmuller, G.; Oh, B.; Brandacher, G.; Alt, J.; Majer, P.; Volsky, D. J.; Rais, R.; Slusher, B. S. N-(Pivaloyloxy) alkoxy-carbonyl Prodrugs of the Glutamine Antagonist 6-Diazo-5-oxo-1-norleucine (DON) as a Potential Treatment for HIV Associated Neurocognitive Disorders. *J Med Chem* 2017, 60, 7186-7198.

Nishio et al., "Antiviral effect of 6-diazo-5-oxo-L-norleucine, antagonist of γ-glutamyl transpeptidase, on replication of human parainfluenza virus type 2," *Journal of General Virology.* 1990; 71:61-67.

Ostrom, Q. T.; Gittleman, H.; Fulop, J.; Liu, M.; Blanda, R.; Kromer, C.; Wolinsky, Y.; Kruchko, C.; Barnholtz-Sloan, J. S. CBTRUS Statistical Report: Primary Brain and Central Nervous System Tumors Diagnosed in the United States in 2008-2012. *Neuro Oncol* 2015, 17 Suppl 4, iv1-iv62.

Ovejera, A. A.; Houchens, D. P.; Catane, R.; Sheridan, M. A.; Muggia, F. M. Efficacy of 6-diazo-5-oxo-L-norleucine and N-[N-gamma-glutamyl-6-diazo-5-oxo-norleucinyl]-6-diazo-5-oxo-norleucine against experimental tumors in conventional and nude mice. *Cancer Res* 1979, 39, 3220-4.

Potter, M. C.; Baxter, V. K.; Mathey, R. W.; Alt, J.; Rojas, C.; Griffin, D. E.; Slusher, B. S. Neurological sequelae induced by alphavirus infection of the CNS are attenuated by treatment with the glutamine antagonist 6-diazo-5-oxo-1-norleucine. *J Neurovirol* 2015, 21, 159-173.

Rahman, A.; Smith, F. P.; Luc, P. T.; Woolley, P. V. Phase I study and clinical pharmacology of 6-diazo-5-oxo-L-norleucine (DON). *Invest New Drugs* 1985, 3, 369-374.

Rais, R.; Jancarik, A.; Tenora, L.; Nedelcovych, M.; Alt, J.; Englert, J.; Rojas, C.; Le, A.; Elgogary, A.; Tan, J.; Monincova, L.; Pate, K.; Adams, R.; Ferraris, D.; Powell, J.; Majer, P.; Slusher, B. S. Discovery of 6-Diazo-5-oxo-1-norleucine (DON) Prodrugs with Enhanced CSF Delivery in Monkeys: A Potential Treatment for Glioblastoma. *J Med Chem* 2016, 59, 8621-33.

Rautio, J.; Kumpulainen, H.; Heimbach, T.; Oliyai, R.; Oh, D.; Jarvinen, T.; Savolainen, J. Prodrugs: design and clinical applications. *Nat Rev Drug Discov* 2008, 7, 255-270.

Reitzer, L. J.; Wice, B. M.; Kennell, D. Evidence that glutamine, not sugar, is the major energy source for cultured HeLa cells. *J Biol Chem* 1979, 254, 2669-76.

Ru, P.; Williams, T. M.; Chakravarti, A.; Guo, D. Tumor metabolism of malignant gliomas. *Cancers (Basel)* 2013, 5, 1469-1484.

Rubin, J.; Sorensen, S.; Schutt, A. J.; van Hazel, G. A.; O'Connell, M. J.; Moertel, C. G. A phase II study of 6-diazo-5-oxo-L-norleucine (DON, NSC-7365) in advanced large bowel carcinoma. *Am J Clin Oncol* 1983, 6, 325-6.

Schulze, A.; Harris, A. L. How cancer metabolism is tuned for proliferation and vulnerable to disruption. *Nature* 2012, 491, 364-373.

Shelton, L. M.; Huysentruyt, L. C.; Seyfried, T. N. Glutamine targeting inhibits systemic metastasis in the VM-M3 murine tumor model. *Int J Cancer* 2010, 127, 2478-85.

Shukla, K.; Ferraris, D. V.; Thomas, A. G.; Stathis, M.; Duvall, B.; Delahanty, G.; Alt, J.; Rais, R.; Rojas, C.; Gao, P.; Xiang, Y.; Dang, C. V.; Slusher, B. S.; Tsukamoto, T. Design, synthesis, and pharmacological evaluation of bis-2-(5-phenylacetamido-1,2,4-thiadiazol-2-yl)ethyl sulfide 3 (BPTES) analogs as glutaminase inhibitors. *J Med Chem* 2012, 55, 10551-10563.

Sklaroff, R. B.; Casper, E. S.; Magill, G. B.; Young, C. W. Phase I study of 6-diazo-5-oxo-L-norleucine (DON). *Cancer Treat Rep* 1980, 64, 1247-1251.

Stupp, R.; Hegi, M. E.; Mason, W. P.; van den Bent, M. J.; Taphoorn, M. J.; Janzer, R. C.; Ludwin, S. K.; Allgeier, A.; Fisher, B.; Belanger, K.; Hau, P.; Brandes, A. A.; Gijtenbeck, J.; Marosi, C.; Vecht, C. J.; Mokhtari, K.; Wesseling, P.; Villa, S.; Eisenhauer, E.; Gorlia, T.; Weller, M.; Lacombe, D.; Cairncross, J. G.; Mirimanoff, R. O. Effects of radiotherapy with concomitant and adjuvant temozolomide versus radiotherapy alone on survival in glioblastoma in a randomised phase III study: 5-year analysis of the EORTC-NCIC trial. *Lancet Oncol* 2009, 10, 459-466.

Shijie, et al., "Blockade of glutamate release from microglia attenuates experimental autoimmune encephalomyelitis in mice," *Tohoku J. Exp. Med.* 2009; 217:87-92).

Stupp, R.; Mason, W. P.; van den Bent, M. J.; Weller, M.; Fisher, B.; Taphoorn, M. J.; Belanger, K.; Brandes, A. A.; Marosi, C.; Bogdahn, U.; Curschmann, J.; Janzer, R. C.; Ludwin, S. K.; Gorlia, T.; Allgeier, A.; Lacombe, D.; Cairncross, J. G.; Eisenhauer, E.; Mirimanoff, R. O. Radiotherapy plus concomitant and adjuvant temozolomide for glioblastoma. *N Engl J Med* 2005, 352, 987-996.

Sullivan, M. P.; Beatty, E. C., Jr.; Hyman, C. B.; Murphy, M. L.; Pierce, M. I.; Severo, N. C. A comparison of the effectiveness of standard dose 6-mercaptopurine, combination 6-mercaptopurine and DON, and high-loading 6-mercaptopurine therapies in treatment of the acute leukemias of childhood: results of a cooperative study. *Cancer Chemother Rep* 1962, 18, 83-95.

Sullivan, M. P.; Nelson, J. A.; Feldman, S.; Van Nguyen, B. Pharmacokinetic and phase I study of intravenous DON (6-diazo-5-oxo-L-norleucine) in children. *Cancer Chemother Pharmacol* 1988, 21, 78-84.

Tanaka, K.; Sasayama, T.; Irino, Y.; Takata, K.; Nagashima, H.; Satoh, N.; Kyotani, K.; Mizowaki, T.; Imahori, T.; Ejima, Y.; Masui, K.; Gini, B.; Yang, H.; Hosoda, K.; Sasaki, R.; Mischel, P. S.; Kohmura, E. Compensatory glutamine metabolism promotes glioblastoma resistance to mTOR inhibitor treatment. *J Clin Invest* 2015, 125, 1591-1602.

Tarnowski, G. S.; Stock, C. C. Effects of combinations of azaserine and of 6-diazo-5-oxo-L-norleucine with purine analogs and other antimetabolites on the growth of two mouse mammary carcinomas. *Cancer Res* 1957, 17, 1033-9.

Thangavelu, K.: Chong, Q. Y.; Low, B. C.; Sivaraman, J. Structural basis for the active site inhibition mechanism of human kidney-type glutaminase (KGA). *Sci Rep* 2014, 4, 3827.

Tran, T. Q.; Ishak Gabra, M. B.; Lowman, X. H.; Yang, Y.; Reid, M. A.; Pan, M.; O'Connor, T. R.; Kong. M. Glutamine deficiency induces DNA alkylation damage and sensitizes cancer cells to alkylating agents through inhibition of ALKBH enzymes. *PLOS Biol* 2017, 15, e2002810.

Ueki, N.; Wang, W.; Swenson, C.; McNaughton, C.; Sampson, N. S.; Hayman, M. J. Synthesis and Preclinical Evaluation of a Highly Improved Anticancer Prodrug Activated by Histone Deacetylases and Cathepsin L. *Theranostics* 2016, 6, 808-16.

Upadhyay, R. K. Drug delivery systems, CNS protection, and the blood brain barrier. *Biomed Res Int* 2014, 2014, 869269.

Weller, M.; van den Bent, M.; Hopkins, K.; Tonn, J. C.; Stupp, R.; Falini, A.; Cohen-Jonathan-Moyal, E.; Frappaz, D.; Henriksson, R.; Balana, C.; Chinot, O.; Ram, Z.; Reifenberger, G.; Soffietti, R.; Wick, W. EANO guideline for the diagnosis and treatment of anaplastic gliomas and glioblastoma. *Lancet Oncol* 2014, 15, e395-403.

Willis, R. C.; Seegmiller, J. E. The inhibition by 6-diazo-5-oxo-1-norleucine of glutamine catabolism of the cultured human lymphoblast. *J Cell Physiol* 1977, 93, 375-382.

Windmueller, H. G.; Spaeth, A. E. Uptake and metabolism of plasma glutamine by the small intestine. *J Biol Chem* 1974, 249, 5070-5079.

Wise, D. R.; DeBerardinis, R. J.; Mancuso, A.; Sayed, N.; Zhang, X. Y.; Pfeiffer, H. K.; Nissim, I.; Daikhin, E.; Yudkoff, M.; McMahon, S. B.; Thompson, C. B. Myc regulates a transcriptional program that stimulates mitochondrial glutaminolysis and leads to glutamine addiction. *Proc Natl Acad Sci USA* 2008, 105, 18782-7.

Wise, D. R.; Thompson, C. B. Glutamine addiction: a new therapeutic target in cancer. *Trends Biochem Sci* 2010, 35, 427-433.

Zhang, W.; Wang, S.; Wang, Q.; Yang, Z.; Pan, Z.; Li, L. Overexpression of cysteine cathepsin L is a marker of invasion and metastasis in ovarian cancer. *Oncology reports* 2014, 31, 1334-1342.

Zimmermann, S. C.; Tichý, T. s.; Vávra, J.; Dash, R. P.; Slusher, C. E.; Gadiano, A. J.; Wu, Y.; Jančařík, A.; Tenora, L. s.; Monincova, L. N-substituted prodrugs of mebendazole provide improved aqueous solubility and oral bioavailability in mice and dogs. *Journal of medicinal chemistry* 2018, 61, 3918-3929.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A compound having a structure of formula (Ih):

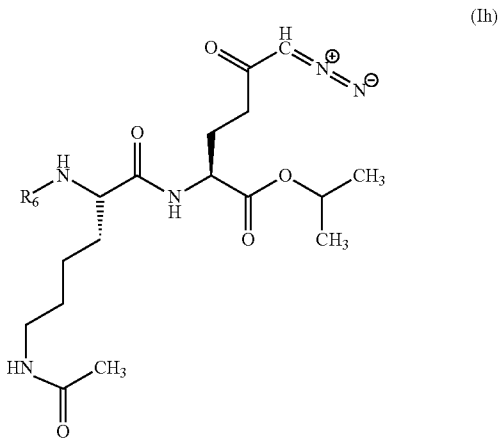

(Ih)

wherein:
$R_6$ is selected from the group consisting of H, —$(CH_2)_t$—CH(NH—C($CH_3$)(=O))—$(CH_2)_t$—$R_9$, —C(=O)—$X_2$—$R_{10}$, and one or more substituted or unsubstituted amino acids, wherein the one or more substituted or unsubstituted amino acids is bound to the nitrogen atom adjacent to $R_6$ through a carboxyl moiety of the one or more substituted or unsubstituted amino acids, wherein $X_2$ is present or absent and, when present, is selected from the group consisting of —O—, —O—$(CH_2)_q$—, —$(CH_2)_t$—, and —$(CH_2)_v$—CH=CH—$(CH_2)_v$—, wherein q and t are each independently selected from the group consisting of 1, 2, 3, 4, 5, 6, 7, and 8, each v is independently selected from the group consisting of 0, 1, 2, 3, 4, 5, 6, 7, and 8, and $R_9$ and $R_{10}$ are each independently selected from the group consisting of straight chain or branched alkyl, heteroalkyl, cycloalkyl, heterocycloalkyl, aryl, and heteroaryl;

or an ester or pharmaceutically acceptable salt thereof.

2. The compound of claim 1, wherein $R_6$ is H.

3. The compound of claim 2, wherein the compound is:

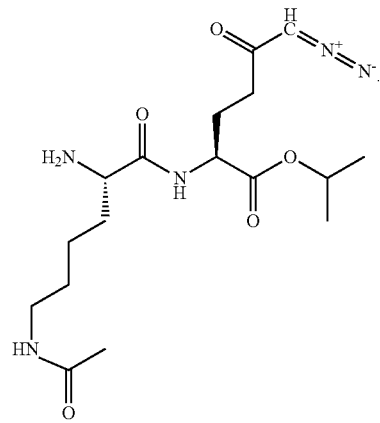

4. The compound of claim 1, wherein $R_6$ is —$(CH_2)_t$—CH(NH—C($CH_3$)(=O))—$(CH_2)_t$—$R_9$.

5. The compound of claim 4, wherein each t is 1 and $R_9$ is aryl.

6. The compound of claim 5, wherein the compound is:

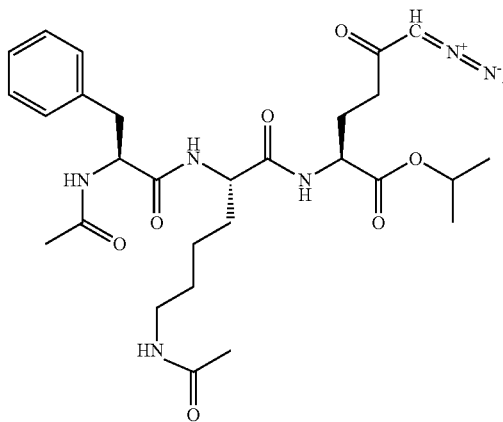

7. The compound of claim 1, wherein $R_6$ is —C(=O)—$X_2$—$R_{10}$.

8. The compound of claim 7, wherein $X_2$ is present and is —O—.

9. The compound of claim 8, wherein $R_{10}$ is selected from the group consisting of t-butyl and adamantanyl.

10. The compound of claim 9, wherein the compound is:

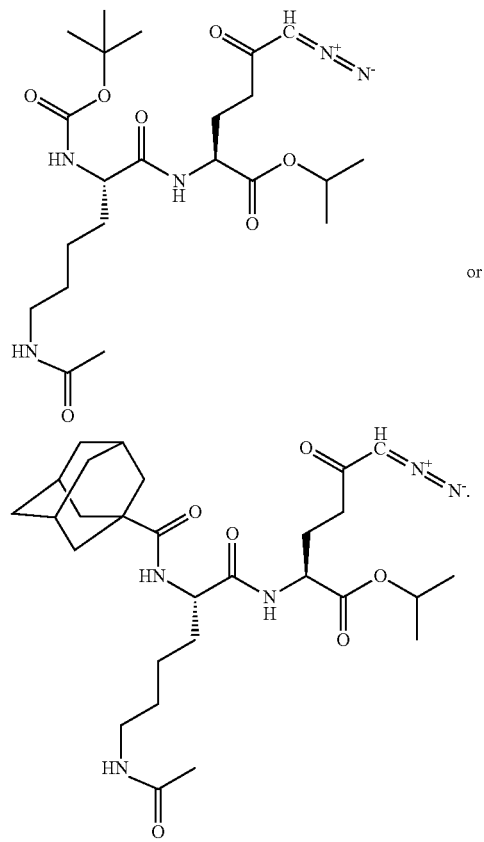

or

11. The compound of claim 7, wherein $X_2$ is present and is —O—$(CH_2)_q$—.

12. The compound of claim 11, wherein q is 1 and $R_{10}$ is selected from the group consisting of 9H-fluoren-9-yl and phenyl.

13. The compound of claim 12, wherein the compound is:

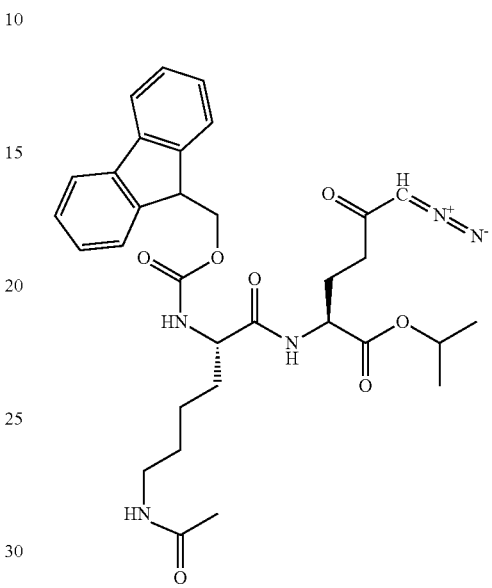

or

14. The compound of claim 7, wherein $X_2$ is absent and $R_{10}$ is selected from the group consisting of $C_2$-$C_{20}$ alkyl, adamantanyl, 1,2,3,4-tetrahydroisoquinolinyl, pyridinyl, and substituted decahydrophenanthrenyl.

15. The compound of claim 14, wherein the compound is:

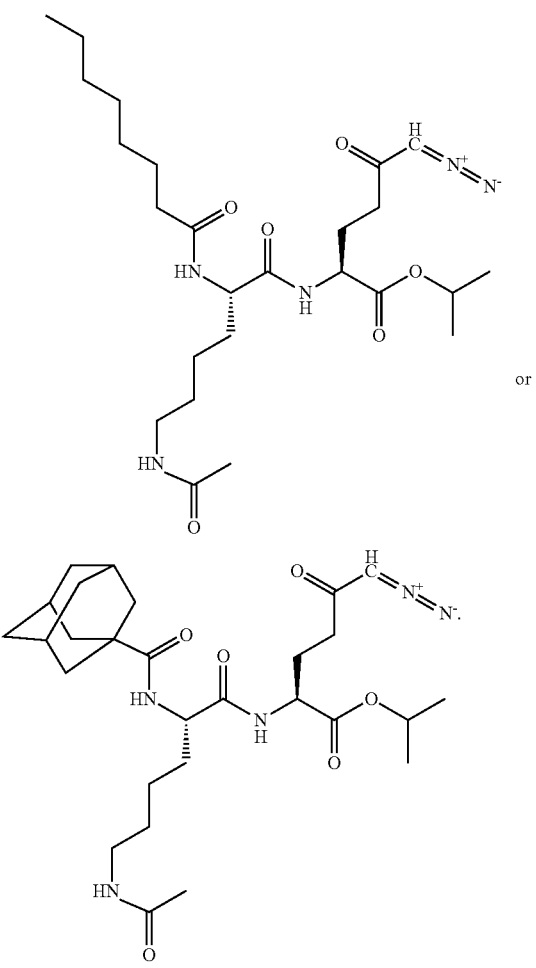

or

16. The compound of claim 7, wherein $X_2$ is —$(CH_2)_t$— and $R_{10}$ is 1H-indol-3-yl.

17. The compound of claim 16, wherein the compound is:

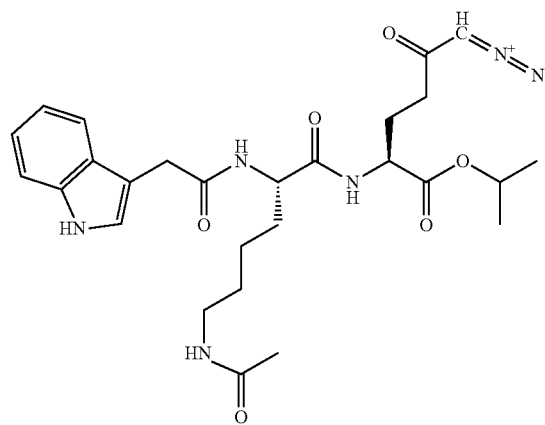

18. The compound of claim 7, wherein $X_2$ is —$(CH_2)_v$—CH=CH—$(CH_2)_{v'}$— and $R_{10}$ is aryl.

19. The compound of claim 18, wherein the compound is:

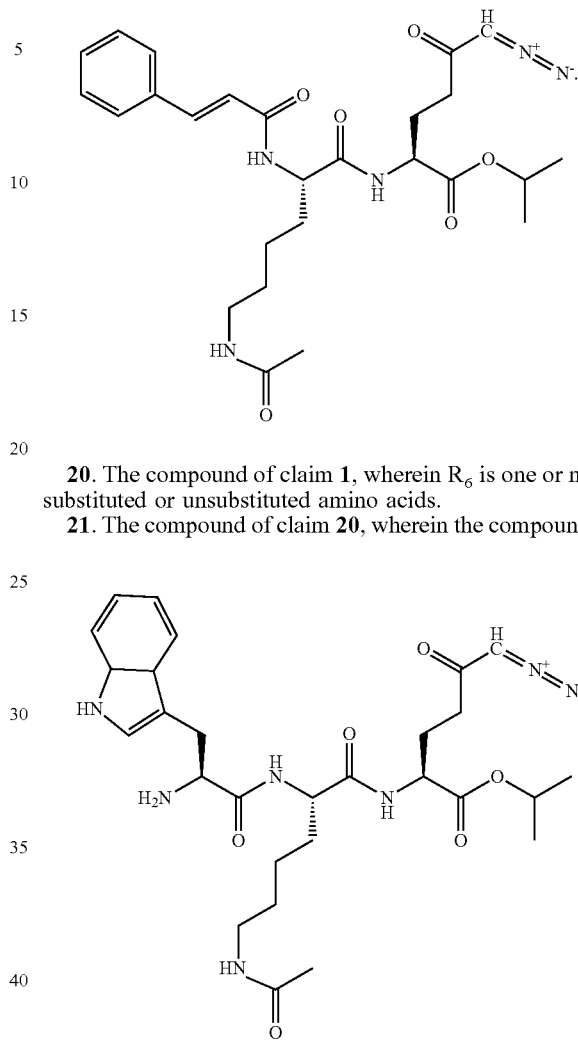

20. The compound of claim 1, wherein $R_6$ is one or more substituted or unsubstituted amino acids.

21. The compound of claim 20, wherein the compound is:

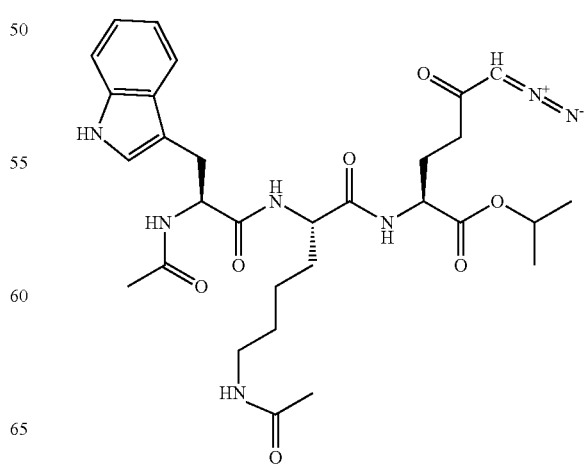

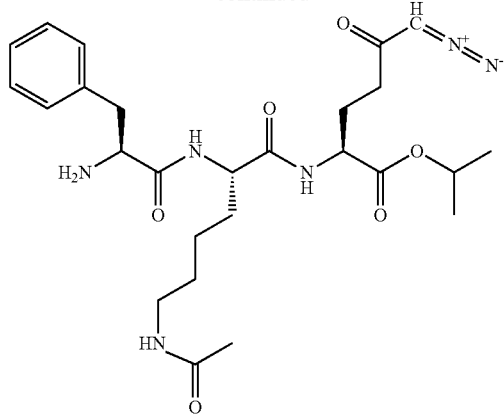

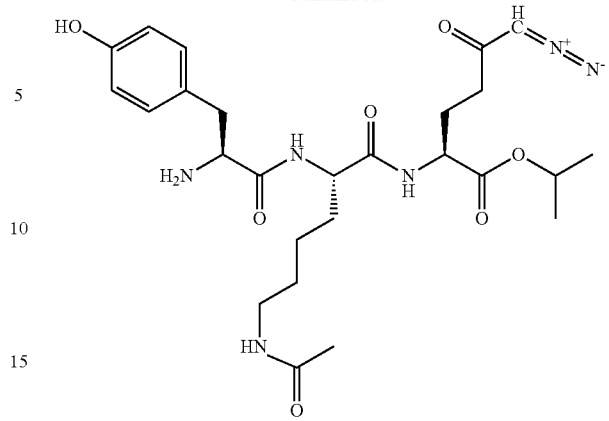

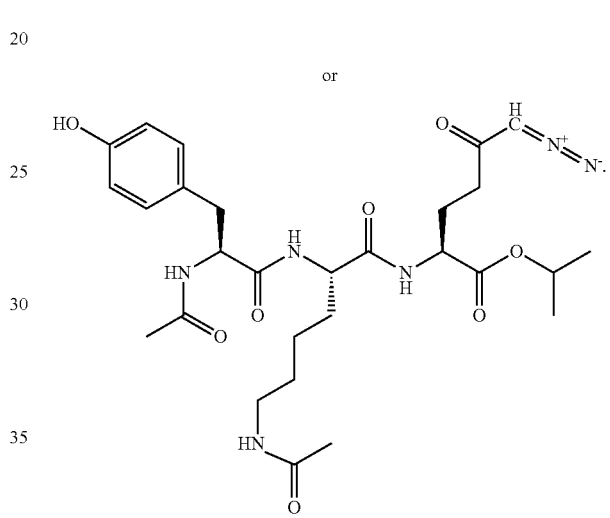

22. The compound of claim 20, wherein the one or more amino acids are valine-leucine.

23. A pharmaceutical composition comprising the compound of any one of claim 1 or 2-22 and a pharmaceutically acceptable carrier, diluent or excipient.

24. The pharmaceutical composition of claim 23, further comprising at least one oncological, immunological, anti-infectious, or neurological agent.

* * * * *